(12) United States Patent
Jiang

(10) Patent No.: US 11,390,874 B2
(45) Date of Patent: Jul. 19, 2022

(54) METHODS FOR GENOMIC INTEGRATION IN PICHIA AND OTHER HOST CELLS

(71) Applicant: Amyris, Inc., Emeryville, CA (US)

(72) Inventor: Hanxiao Jiang, Fremont, CA (US)

(73) Assignee: Amyris, Inc., Emeryville, CA (US)

( * ) Notice: Subject to any disclaimer, the term of this patent is extended or adjusted under 35 U.S.C. 154(b) by 74 days.

(21) Appl. No.: 16/646,001

(22) PCT Filed: Sep. 12, 2018

(86) PCT No.: PCT/US2018/050613
§ 371 (c)(1),
(2) Date: Mar. 10, 2020

(87) PCT Pub. No.: WO2019/055481
PCT Pub. Date: Mar. 21, 2019

(65) Prior Publication Data
US 2020/0208163 A1 Jul. 2, 2020

Related U.S. Application Data

(60) Provisional application No. 62/560,026, filed on Sep. 18, 2017, provisional application No. 62/666,923, filed on May 4, 2018.

(51) Int. Cl.
*C12N 15/90* (2006.01)
*C12N 15/81* (2006.01)

(52) U.S. Cl.
CPC ......... *C12N 15/815* (2013.01); *C12N 15/905* (2013.01)

(58) Field of Classification Search
None
See application file for complete search history.

(56) References Cited

PUBLICATIONS

Arruda et al., Biotechnol Lett, vol. 38, pp. 509-517, 2016.*
Cho et al., ACS Synthetic Biology, 7, pp. 1085-1094, Mar. 15, 2018.*
Chakraborty, S. (Dec. 1, 2019), Prime-editors (nickases), hRad51-Cas9 nickase fusions and dCas9 have the same problem as conventional CRISPR-Cas9 of plasmid/Cas9 integration after making a double stranded break, https://doi.org/10.31219/osf.io/jf6pe.*
International Search Report and Written Opinion in PCT Application PCT/US2018/050613 dated Jan. 4, 2019; 14 pages.
Gao, S. et al.; "Multiplex gene editing of the *Yarrowia lipolytica* genome using the CRISPR-Cas9 system"; Journal of Industrial Microbiology and Biotechnology; vol. 43, No. 8; Jun. 27, 2016; pp. 1085-1093.
Goncalves, A.M., et al.; "*Pichia pastoris*: A Recombinant Microfactory for Antibodies and Human Membrane Proteins"; *Journal of Microbiology and Biotechnology*; vol. 23, No. 5; May 1, 2013; pp. 587-601.
Horwitz, A.A. et al.; "Efficient Multiplexed Integration of Synergistic Alleles and Metabolic Pathways in Yeasts via CRISPR-Cas"; *Cell Systems*: vol. 1, No. 1; Jul. 1, 2015; pp. 88-96.
Naatsaari, L. et al.; "Deletion of the Pichia pastoris KU70 Homologue Facilitates Platform Straing Generation for Gene Expression and Synthetic Biology"; *PLOS One*; Jul. 29, 2012; 14 pages.
Vogl, T. et al.; "New opportunities by synthetic biology for biopharmaceutical production in Pichia pastoris"; *Current Opinion in Biotechnology*; vol. 24, No. Dec. 6, 24, 2013; pp. 1094-1101.
Weninger, A. et al.; "Combinatorial optimization of CRISPR/Cas9 expression enables precision genome engineering in the methylotrophic yeast *Pichia pastoris*" *Journal of Biotechnology*: vol. 235; Mar. 22, 2016; pp. 139-149.

* cited by examiner

*Primary Examiner* — Richard G Hutson
(74) *Attorney, Agent, or Firm* — Kilpatrick Townsend & Stockton LLP

(57) ABSTRACT

The present invention provides high efficiency targeted and marker-less single, double, triple, quadruple, and quintuple integrations by using CRISPR in host cells, including Pichia.

8 Claims, 2 Drawing Sheets

Specification includes a Sequence Listing.

METHODS FOR GENOMIC INTEGRATION IN PICHIA AND OTHER HOST CELLS

CROSS REFERENCES TO RELATED APPLICATIONS

The present application is a US National Phase Application Under 371 of PCT/US2018/050613 filed Sep. 12, 2018, which claims priority to U.S. Provisional Patent Application No. 62/560,026, filed on Sep. 18, 2017 and U.S. Provisional Patent Application No. 62/666,923 filed on May 4, 2018, each of which is incorporated herein by reference in its entirety.

REFERENCE TO SUBMISSION OF A SEQUENCE LISTING AS A TEXT FILE

The Sequence Listing written in file 101928-1100559 SL.txt created on Mar. 5, 2020, 68,581 bytes, machine format IBM-PC, MS-Windows operating system, is hereby incorporated by reference in its entirety for all purposes.

BACKGROUND OF THE INVENTION

Typically *P. pastoris* is transformed using vectors or linear constructs with drug or auxotrophic markers. To improve protein production from integrated constructs, clones are passaged on increasing concentrations of a drug, selecting for amplification of the construct in a random fashion. Targeted integration is possible, and greatly improved when YKU70 is deleted in yeast cells to reduce NHEJ (non-homologous end joining) repair mechanisms. However, available markers are limited, and marker recycling (i.e., reusing of the same marker) is necessary for more ambitious engineering efforts. For rapid strain engineering, for example, in *P. pastoris*, a highly efficient, marker-less and targeted homologous integration transformation method is desired. Recently, Weninger et al. (*Journal of Biotechnology* 235:139-149 2016) reported a CRISPR protocol in *P. pastoris* using a strong constitutive promoter for Cas9 expression, and an RNA polymerase II promoter driving expression of the gRNA, with all components contained on a large plasmid. The study reported high efficiency of insertion and deletion (indel) introduction by NHEJ into a single gene, or multiple genes, which usually results in loss of function, equivalent to a knockout. However, when marker-less donor DNA was provided for targeted integration, a rate of only 2.4% was observed.

Thus, current known methods are in need of improvement. The present invention addresses these and other needs.

BRIEF SUMMARY OF THE INVENTION

The present invention provides methods of disrupting or inserting a desired donor DNA molecule into one or more target sites in a host cell genome.

In some embodiments, the methods comprise (a) contacting a host cell, which comprises a nucleic acid encoding an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site. A transformed host cell expressing the selectable marker is then selected. In some embodiments, NHEJ is reduced in the host cell. In some embodiments, the nucleic acid encoding an RNA-guided DNA endonuclease is integrated into the host cell genome.

In some embodiments, the method further comprises contacting the host cell with a donor DNA molecule capable of homologous recombination with the target site, whereby homologous recombination in the host cell results in integration of the donor DNA molecule at the target site. In some embodiments, the donor DNA molecule comprises a nucleic acid sequence encoding an antibody. In some cases, the step of contacting includes contacting the cell with two or more donor DNA molecules capable of homologous recombination with different target sites, whereby homologous recombination in the host cell results in integration of the donor DNA molecules at the different target sites.

The host cell used in any of the methods provided herein may be, for example, a non-conventional yeast cell. In some embodiments, the host cell is *Pichia*, in particular, *Pichia pastoris*.

In some embodiments, the step of contacting includes contacting the cell with two or more second linear nucleic acid molecules, wherein each second linear nucleic acid molecule comprises a nucleic acid encoding a different guide RNA, which guides the DNA nuclease to a different target site. The methods according to the present invention result in high efficiency for single, double, or multiple efficiency for targeted integration of donor nucleic acids into the host cell genome. As used herein, the targeting efficiency refers to a percentage of transformed cells comprising a successful integrated donor nucleic acids among screened cells.

In some embodiments, the nucleic acid encoding the RNA-guided DNA endonuclease can be operably linked to a *Pichia* pPGK1 promoter. In addition, the nucleic acid encoding the RNA-guided DNA endonuclease can be integrated in a YKU70 gene, thereby reducing NHEJ activity in the host cell. In certain embodiments, the nucleic acid encoding the RNA-guided DNA endonuclease can be integrated at another genomic locus to reduce NHEJ, such as in a YKU80 gene. In other embodiments, the nucleic acid encoding the RNA-guided DNA endonuclease can be integrated at a different genomic locus, and one or more genes involved in the NHEJ process can be functionally disrupted separately. The RNA-guided DNA endonuclease can be Cas9. In some embodiments, the nucleic acid sequence encoding the Cas9 is codon optimized for expression in *Saccharomyces*.

The invention also provides host cells made by the methods of the invention. The host cell may comprise a donor DNA molecule comprising a nucleic acid sequence encoding an antibody. Thus, the invention also provides methods of producing an antibody. The methods comprise culturing the host cell under conditions suitable for production of the antibody and recovering the antibody produced by the host cell. The host cell can be *Pichia*.

DEFINITIONS

Figure 1A:
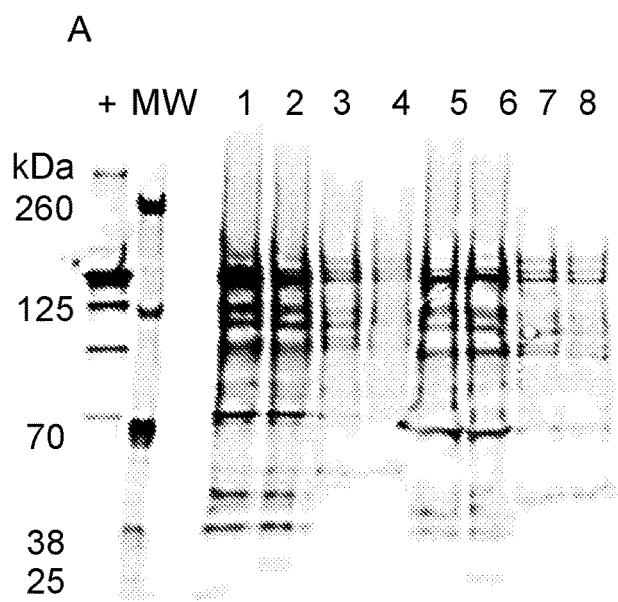
FIGS. 1A and 1B illustrate secretion of full-length Herceptin and Rituxan by engineered *P. pastoris* strains. Protein A purified samples were assayed by Western Blot under non-reducing (A) and reducing (B) conditions. Lanes 1-4, Protein A purified samples; lanes 5-8, Protein A purified and Endo $H_f$ treated samples. Lanes 1 and 5, Herceptin with pre-alpha secretion leader sequence; lanes 2 and 6, Herceptin with pre-alpha secretion leader sequence and KR mutated to TR in LC; lanes 3 and 7, Rituxan with Kar2 leader sequence; lanes 4 and 8, Rituxan with Kar2 sequence and KR mutated to TR in LC. MW, molecular weight marker, with quantities on the left of each gel. +, BIIB antibody standard.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA, or micro RNA A "promoter" is defined as one or more a nucleic acid control sequences that direct transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

As used herein, the term "marker-less" refers to integration of a donor DNA into a target site within a host cell genome without accompanying integration of a selectable marker. The term also refers to instances where a selectable marker gene is not integrated into the host cell genome for the recovery of a host cell in which a donor DNA is integrated into the host cell genome. In some embodiments, the term also refers to the recovery of such a host cell without utilizing a selection scheme that relies on integration of selectable marker into the host cell genome. For example, in certain embodiments, a selection marker that is episomal or extrachromasomal may be used to select for cells comprising a plasmid comprising a gRNA. Such use would be considered marker-less, as long as the selectable marker is not integrated into the host cell genome.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

As used herein, the term "transformation" refers to a genetic alteration of a host cell resulting from the introduction of exogenous genetic material into the host cell.

As used herein, the term "selecting a host cell expressing a selectable marker" also encompasses enriching for host cells expressing a selectable marker from a population of transformed cells.

As used herein, the term "selectable marker" refers to a gene which functions as guidance for selecting a host cell comprising a marker, for example, a marker expressed by a circular, extrachromosomal nucleic acid in the host cell, as described herein. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. Drug selectable markers suitable for use with the methods and compositions provided herein include, but are not limited to, resistance genes to antibiotics, such as ampicillin, streptomycin, gentamicin, kanamycin, hygromycin, tetracycline, chloramphenicol, and neomycin. In some embodiments, the selection may be positive selection; that is, the cells expressing the marker are isolated from a population, e.g. to create an enriched population of cells comprising the selectable marker. In other instances, the selection may be negative selection; that is, the population is isolated away from the cells, e.g. to create an enriched population of cells that do not comprise the selectable marker. Separation can be by any convenient separation technique appropriate for the selectable marker used. For example, if a fluorescent marker is used, cells can be separated by fluorescence activated cell sorting, whereas if a cell surface marker has been inserted, cells can be separated from the heterogeneous population by affinity separation techniques, e.g. magnetic separation, affinity chromatography, "panning" with an affinity reagent attached to a solid matrix, or other convenient technique.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. In some embodiments, for example, and not to be limiting, base pairing between a guide RNA and a target site or region in the genome of a host cell is described. Complementary nucleotides are, generally, A and T (or A and U), and G and C. The guide RNAs described herein can comprise sequences, for example, a DNA targeting sequence that is perfectly complementary or substantially complementary (e.g., having 1-4 mismatches) to a genomic sequence in a host cell.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-guided DNA endonuclease, Cas9, in complex with a guide RNA to recognize and cleave foreign nucleic acid.

As used herein, the terms "cleave," "cleavage" and/or "cleaving" with respect to an RNA-guided endonuclease, for example, Cas9, refers to the act of creating a break in a particular nucleic acid. The break can leave a blunt end or sticky end (i.e., 5' or 3' overhang), as understood by those of skill in the art. The terms also encompass single strand DNA breaks ("nicks") and double strand DNA breaks.

As used herein, the term "Cas9" refers to an RNA-guided nuclease (e.g., of bacterial or archeal orgin, or derived therefrom). RNA-guided nucleases include the foregoing Cas9 proteins and homologs thereof, and include but are not limited to, Cpf1 (See, e.g., Zetsche et al., Cell, Volume 163, Issue 3, p759-771, 22 Oct. 2015).

Cas9 homologs are found in a wide variety of eubacteria, including, but not limited to bacteria of the following taxonomic groups: *Actinobacteria, Aquificae, Bacteroidetes-Chlorobi, Chlamydiae-Verrucomicrobia, Chlroflexi, Cyanobacteria, Firmicutes, Proteobacteria, Spirochaetes,* and *Thermotogae*. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737 ; Nat. Rev. Microbiol. 2011 June; 9(6): 467-477; Hou, et al., Proc Natl Acad Sci USA. 2013 Sep. 24;110(39):15644-9; Sampson et al., Nature. 2013 May 9;497(7448):254-7; and Jinek, et al., Science. 2012 Aug. 17;337(6096):816-21. Variants of any of the Cas9 nucleases provided herein can be optimized for efficient activity or enhanced stability in the host cell. Thus, engineered Cas9 nucleases, for example, codon optimized Cas9 nucleases for expression in *Pichia* or *Saccharomyces* are also contemplated.

As used herein, the phrase "disrupting" or "disruption" in the context of disrupting a target site in a host cell genome refers to inducing a nucleic acid break in the target site. A disruption can be used to edit the genome. As used herein the term "editing" refers to a structural change in the sequence of the genome at a target site. For example, the host cell genome may be edited by deleting or inserting a nucleotide sequence into the genome of the cell. The nucleotide sequence can encode a polypeptide or a fragment thereof. Such editing can be performed, for example, by inducing a double stranded break within a target site in the genome of a host cell, or a pair of single stranded nicks on opposite strands and flanking the target site in the genome of a host cell. Methods for inducing single or double stranded breaks at or within a target site include the use of an RNA-guided DNA endonuclease, or a derivative thereof, and a guide RNA directed to the target site in the genome of a host cell.

As used herein the phrase "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein the term "homologous recombination" refers to a cellular process in which nucleotide sequences are exchanged between two similar or identical molecules of DNA.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid, for example a donor DNA molecule. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid, for example, a donor DNA molecule can be introduced to obtain a specific HDR-induced change of the sequence at the target site. In this way, specific sequences can be introduced at the cut site.

As used herein, the phrases "introducing" or "contacting" in the context of introducing a nucleic acid or protein into a host cell refers to any process that results in the presence of a heterologous nucleic acid or polypeptide inside the host cell. For example, the terms encompass introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The terms also encompass integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein, the term "full-length antibody" refers to an antibody having a structure substantially similar to a native antibody structure. A full-length antibody includes four polypeptides—two light chains and two heavy chains joined by disulfide bonds to form a "Y" shaped molecule. Each heavy chain includes a constant region and a variable region join by a hinge region. The two constant regions of the two heavy chains form an Fc domain. A full-length antibody may be of any isotype (e.g., IgA, IgD, IgE, IgG, and IgM), which is defined by the heavy chain of the antibody.

DETAILED DESCRIPTION OF THE INVENTION

Methods of Disrupting a Target Site in a Host Cell Genome

Provided herein are methods of disrupting one or more target sites in a host cell genome. These methods allow efficient, simultaneous integration of one or more donor DNA molecules into a host cell genome. In some of the methods the one or more donor DNA molecules are integrated into the host cell genome without concomitant integration of a selectable marker into the host cell genome.

In some embodiments, disruption of one or more target sites comprises (a) contacting a host cell, which expresses an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site. A transformed host cell expressing the selectable marker is then selected.

In some embodiments, disruption of one or more target sites comprises (a) contacting a host cell, which expresses an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site, wherein the host cell has reduced NHEJ activity. A transformed host cell expressing the selectable marker is then selected.

In some embodiments, the method further comprises contacting the host cell with a donor DNA molecule capable of homologous recombination with the target site, whereby homologous recombination in the host cell results in integration of the donor DNA molecule at the target site. In some embodiments, the donor DNA molecule is a heterologous donor DNA molecule. In some embodiments, the donor DNA molecule is flanked by nucleotide sequences that are homologous to genomic sequences flanking the target site. In some embodiments, the donor DNA molecule comprises a homologous sequence at the 5' terminus that is about 70%, 75%, 80%, 85%, 90%, 95% or 100% homologous to a 5' region of a selected genomic target site In some embodiments, the donor DNA molecule comprises a homologous sequence at the 3' terminus that is about 70%, 75%, 80%, 85%, 90%, 95% or 100% homologous to a 3' region of a selected genomic target site. In some cases, each of the homologous sequences flanking the donor DNA molecule comprises from about 50 to about 5,000 nucleotides, from about 100 to 2500 nucleotides, from about 200 to 1500 nucleotides, from about 500 to about 1000 nucleotides, or any number of nucleotides within these ranges. See, for example, U.S. Pat. No. 9,476,065.

In some embodiments, NHEJ is reduced in the host cell prior to contacting the host cell with the first linear nucleic acid, the second linear nucleic acid and/or the donor DNA molecule. In some embodiments, NHEJ is reduced in the host cell simultaneously with contacting the host cell with the first linear nucleic acid, the single linear nucleic acid and/or the donor DNA molecule. In some embodiments, NHEJ is reduced in the host cell after contacting the host cell with the first linear nucleic acid, the single linear nucleic acid and/or the donor DNA molecule.

In some embodiments, the donor DNA molecule comprises a nucleic acid of interest. For example, the donor DNA molecule may comprise a gene of interest that can be knocked in to a host genome. In other embodiments, the donor DNA molecule functions as a knockout construct that is capable of specifically disrupting a target gene upon integration of the construct into the target site of the host cell genome, thereby rendering the disrupted gene non-functional. Examples of nucleic acids of interest include, but are not limited to, a protein-coding sequence, a promoter, an enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In specific embodiments, the nucleic acid of interest does not comprise a nucleic acid encoding a selectable marker.

In some embodiments the nucleic acid of interest encodes an antibody, for example, and not to be limiting, a monoclonal antibody, a Fab fragment, a single-chain variable fragment (scFv), a dimeric single-chain variable fragment (di-ScFv), or a single-domain antibody (sdAb). In some embodiments, the nucleic acid of interest encodes the full-length antibody Herceptin (trastuzumab). In some embodiments, the nucleic acid of interest encodes the full-length antibody Rituxan (rituximab). In some embodiments, the nucleic acid of interest excludes the nucleic acid that encodes the full-length antibody Herceptin (trastuzumab), the full-length antibody Rituxan (rituximab), or the full-length antibody BIIB. In other embodiments, the nucleic acid of interest encodes an enzyme, a hormone, a growth factor, an anticoagulant, blood factors, an engineered protein, an interferon, an interleukin, a thrombolytic, a viral protein or a bacterial protein.

In the methods and compositions provided herein, the host cell can be a prokaryotic cell or a eukaryotic cell. In some embodiments, the host cell is selected from the group consisting of a fungal cell, a bacterial cell, a plant cell, an insect cell, an avian cell, a fish cell and a mammalian cell. In some embodiments, the mammalian cell is selected from the group consisting a rodent cell, a primate cell and a human cell. In some embodiments, the fungal cell is a yeast cell. In some embodiments, the yeast cell is a non-conventional yeast cell. A non-conventional yeast cell refers to yeast species which utilizes non-homologous end joining as a predominant mechanism for a DNA repair system, in contrast a conventional yeast cell (e.g., *Saccharomyces* or *Schizomyces*), which utilizes homologous recombination as a dominant mechanism for DNA repair system. Examples of non-conventional yeast cells include *Pichia* (e.g., *P. pastoria*), *Kluyveromyces* (*K. marxianus*, or *K. lactis*), *Hansenula* (e.g., *H. polymorpha*), or *Arxula* (*A. adninivorans*). In some embodiments, the yeast cell is a *Pichia* cell. In specific embodiments, the yeast cell is a *Pichia pastoris* cell. Examples of host cells that can be used in the methods described herein are described in International Application Publication No. WO2015/095804. In some embodiments, the host cell does not comprise a nucleic acid that encodes the full-length antibody Herceptin (trastuzumab), the full-length antibody Rituxan (rituximab), or the full-length antibody BIIB. In some embodiments, the host cell does not express a the full-length antibody Herceptin (trastuzumab), the full-length antibody Rituxan (rituximab), or the full-length antibody BIIB.

In some embodiments, a host cell with reduced NHEJ activity is a cell that has a disruption in a gene locus that is involved in NHEJ activity of the cell (i.e., a disruption in one or more genes that encode proteins that drives the NHEJ pathway or contribute to NHEJ Examples of NHEJ pathway genes for *Pichia* include, but are not limited to, YKU70, YKU 80, DNL4, Rad50, Rad 27, MRE11, and POL4. The names of genes may be different for different host cells. Suitable NHEJ pathway genes for disruption can be found in, e.g., KEGG Non-homologous end-joining pathway at http://www.genome.jp/kegg-bin/show_pathway?map=ko03450&show_description=show. In some embodiments, the host cell with reduced NHEJ activity is a yeast cell, for example, a *Pichia* cell, with a disruption in the YKU70 gene locus, such that NHEJ activity is reduced in the cell. In some cases, the YKU70 gene locus is disrupted by inserting or integrating a nucleic acid encoding an RNA-guided endonuclease in the YKU70 gene locus. The reduction in NHEJ activity can be a reduction of NHEJ events in the host cell, for example, a reduction of at least 20%, 30%, 40%, 50%, 60%, 70%, 80%, 90%, 100% or any percent reduction in between these percentages, as compared to a host cell that does not have a disruption in a gene controlling NHEJ in the cell, for example, a yeast cell with a disruption in the YKU70 gene locus of a *Pichia s* cell.

In some embodiments, the RNA-guided DNA endonuclease is provided by introducing a nucleic acid encoding the endonuclease into the host cell. For example, a plasmid or vector comprising a nucleic acid encoding the RNA-guided DNA endonuclease can be introduced into the cell. In some embodiments, the plasmid can further comprise a nucleic acid sequence encoding a selectable marker for maintenance of the plasmid in the host cell. In some embodiments the nucleic acid encoding the endonuclease further comprises a promoter sequence. In some embodiments, the nucleic acid encoding the RNA-guided DNA endonuclease is integrated into genome of the host cell. In certain embodiments, the RNA-guided DNA endonuclease, for example, Cas9, is integrated into the YKU70 gene of a yeast cell, thereby reducing NHEJ activity in the yeast cell. In some embodiments, the nucleic acid encoding the RNA-guided DNA endonuclease is under the control of a constitutive promoter. In specific embodiments, the nucleic acid encoding the RNA-guided DNA endonuclease is under the control of a medium-strength *Pichia* pPGK1 promoter. Examples of suitable promoters include, but are not limited to, pYPT1, pTEF1, pSSA3, pGPM1, pENO1. In some embodiments, the RNA-guided DNA endonuclease can be introduced into the host cell prior to, simultaneously with, or after introduction of the first and second linear nucleic acids. In other embodiments, the RNA-guided DNA endonuclease can be introduced into the host cell prior to, simultaneously with, or after introduction of the first linear nucleic acids, the second linear nucleic acid and the donor DNA molecule. In some embodiments, an RNA encoding the RNA-guided DNA endonuclease can be introduced into the host cell. In other embodiments, the RNA-guided DNA endonuclease protein or a functional fragment thereof can be introduced into the host cell.

In some embodiments, the first linear nucleic acid comprises two internal homologous sequences that are capable of homologously recombining with each other, whereby homologous recombination of the internal homologous sequences results in formation of the circular extrachromosomal nucleic acid expressing the selectable marker. In some embodiments, the first linear nucleic acid is capable of recombining with the second linear nucleic acid. In some embodiments, the first linear nucleic acid comprises a selectable marker, such that, after introduction of the first and second linear nucleic acids, the first and second linear nucleic acids undergo homologous recombination to form a circular, episomal or extrachromosomal nucleic acid comprising the coding sequence for the selectable marker and the guide RNA, for example, via, gap repair,. Once circularized, the extrachromosomal nucleic acid includes a coding sequence for a selectable marker, and suitable regulatory sequences such as a promoter and/or a terminator that enables expression of the marker in the host cell. Providing the selectable marker on a circular, extrachromosomal nucleic acid, allows marker-less integration of one or more donor DNA molecules into a host cell genome, while avoiding the integration of extraneous sequences (i.e., a selectable marker) into the genome and any deleterious effects associated with prolonged marker expression. See, for example, U.S. Pat. No. 9,476,065 for gap repair mechanisms that can be used in the methods described herein.

Subsequent to formation of the extrachromosomal nucleic acid comprising the coding sequence for the selectable marker and the guide RNA, the guide RNA is transcribed from the extrachromosomal nucleic acid and guides the RNA-guided DNA endonuclease expressed in the host cell to a target site in the genome of the host cell, where the endonuclease creates a break at the target site. In some embodiments, once the endonuclease creates a break at the target site, the donor DNA molecule is integrated into the host cell genome via homologous recombination.

In some embodiments, the method comprises integrating a plurality (i.e., two or more) donor DNA molecules into a plurality of target sites of the host cell genome. In some embodiments, the host cell is contacted with a first linear nucleic acid and two or more second linear nucleic acid molecules, wherein each second linear nucleic acid molecule comprises a nucleic acid encoding a different guide RNA which targets a different site in the host cell genome. Each different second linear nucleic acid can recombine with the first linear nucleic acid to form two or more different, circular, extrachromosomal nucleic acids in the host cell. It is understood that the term "first linear nucleic acid" and "second linear nucleic acid" includes multiple copies of the same nucleic acid molecule. For example, the host cell can be contacted with two or more second linear nucleic acid molecules, wherein each second linear nucleic acid molecule comprises a nucleic acid encoding a different guide RNA to target two, three, four, five, six, seven or more different sites in the host cell genome. In some embodiments, once the guide RNA guides the RNA-guided endonuclease to two or more target sites, the endonuclease creates a break at the two or more target sites and two or more donor DNA molecules are integrated into the host cell genome via homologous recombination.

In some embodiments, the circular extrachromosomal nucleic acid comprises the coding sequence for the selectable marker and a guide RNA cassette comprising, from 5' to 3', the RNA polymerase II promoter, the first nucleic acid encoding a first ribozyme, the nucleic acid encoding a guide RNA, the second nucleic acid encoding a second ribozyme, and the terminator.

Examples of promoters that can be used in any of the methods provided herein to control expression of a guide RNA include, but are not limited to, a *Pichia* Pol II promoter (pHTA1), *Saccharomyces* promoterpPGK/, *Saccharomyces* promoterpTDH3, and *Saccharomyces* promoterpACT1. In some embodiments, the promoter, for example, an RNA polymerase II promoter, is from the same species as the host cell. In other embodiments, the promoter, for example, an RNA polymerase II promoter, is from a different species than the host cell.

By flanking the guide RNA with a first and second ribozyme, upon transcription of the gRNA cassette, under the control of the RNA polymerase II promoter, the ribozymes self-cleave the transcript to produce the desired guide RNA sequence. See, for example, Gao and Zhao (*J. Integr. Plant Biol.* 56(4): 343-349 (2014)). In some embodiments, the guide RNA is flanked by a hammerhead (HH) and hepatitis delta virus (HDV) ribozyme sequences. In specific embodiments, one or both of the ribozymes are flanked by linker sequences to facilitate release of the guide RNA after cleavage. In some embodiments, the linker sequence is at least 5, 6, 7, or 8 nucleotides in length. Exemplary linker sequences are provided in the Examples.

In some embodiments, the first linear nucleic acid comprising a selectable marker is a gapped vector comprising a pair of homologous flanking sequences that recombine with a pair of homologous sequences flanking the gRNA cassette in the second linear nucleic acid to form a larger circular vector where the gap has been repaired by inserting the second linear nucleic acid into the gapped vector. In some embodiments each homologous flanking sequence of the pair of homologous flanking sequences in the first nucleic acid contains a recombination region comprising a nucleotide sequence of sufficient length and sequence identity that allows for homologous recombination with the pair of homologous flanking sequences in the second linear nucleic acid, but not with other regions of the first or second linear nucleic acid participating in the in vivo assembly, nor with any genomic regions of the host cell. For in vivo assembly of marker/gRNA vectors via gap repair and for selection of cells capable of homologous recombination and gap repair, see, for example, Horwitz et al. (*Cell Systems* 1:88-96 (2015)) and International Application Publication No. WO2015/095804, both of which are incorporated herein in their entireties by this reference.

In some embodiments, "sufficient sequence identity" refers to sequences with at least 70%, at least 75%>, at least 80%>, at least 85%>, at least 90%>, at least 95%>, at least 99%>, or 100%, identity between recombination regions, over a length of, for example, at least 15 base pairs, at least 20 base pairs, at least 50 base pairs, at least 100 base pairs, at least 250 base pairs, at least 500 base pairs, or more than 500 base pairs. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, *J. Mol. Biol.* 48: 443 (1970). For a discussion of effective lengths of homology between recombination regions, see Hasty et al. (*Mol Cell Biol* 11:5586-91 (1991)).

Using the methods provided herein, one or more target sites in a host cell genome can be modified with surprisingly high efficiency compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% 80%, 85%, 90%, 95%, or higher, or any percentage in between these percentages.

In some embodiments, the methods of the invention provide for markerless recovery of a transformed host cell comprising a successfully integrated donor nucleic acid. Such a cell occurs within a frequency of about one every 1000, 900, 800, 700, 600, 500, 400, 300, 200 or 100 contacted host cells, or clonal populations thereof, screened. In particular embodiments, markerless recovery of a transformed host cell comprising a successfully integrated donor nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated donor nucleic acid occurs within a frequency of about one every 9, 8, 7, 6, 5, 4, 3, or 2 contacted host cells, or clonal populations thereof, screened.

In certain embodiments, markerless recovery of a transformed cell comprising a successfully integrated donor nucleic acid at a single locus occurs within a frequency of at least 10%, 20%, 30%, 50%, 60%, 70%, 80%, 90%, or 100% of contacted host cells or clonal population thereof, screened. In certain embodiments, markerless recovery of a transformed cell comprising successfully integrated donor nucleic acids at two, three, four, or five loci occurs at least 10%, 20%, 30%, 40%, 50%, 60%, 70%, 80%, 90%, or 100% of contacted host cells or clonal population thereof, screened. In certain embodiments, any suitable number of donor nucleic acids (e.g., n=1 to 20) can be successfully integrated at n loci in the host cell genome.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof Phenotypic readouts, for example, a predicted gain or loss of function, can also be used as a proxy for effecting the intended genomic modification(s).

Cell Culture

In some embodiments of the methods described herein, host cells are cultured for a period of time sufficient for expression of the selectable marker from the circularized extrachromosomal vector. In some embodiments where the selectable marker is a drug resistance marker, the culturing is carried out for a period of time sufficient to produce an amount of the marker protein that can support the survival of cells expressing the marker in selectable media. In certain embodiments, these conditions also select against the survival of cells not expressing the selectable marker. Selective pressure can be applied to cells using a variety of compounds or treatments that would be known to one of skill in the art. For example, selective pressure can be applied by exposing host cells to conditions that are suboptimal for or deleterious to growth, progression of the cell cycle or viability, such that cells that are tolerant or resistant to these conditions are selected for compared to cells that are not tolerant or resistant to these conditions. Conditions that can be used to exert or apply selective pressure include, but are not limited to, antibiotics, drugs, mutagens, compounds that slow or halt cell growth or the synthesis of biological building blocks, compounds that disrupt RNA, DNA or protein synthesis, deprivation or limitation of nutrients, amino acids, carbohydrates or compounds required for cell growth and viability from cell growth or culture media, treatments such as growth or maintenance of cells under conditions that are suboptimal for cell growth, for instance at suboptimal temperatures, atmospheric conditions (e.g., % carbon dioxide, oxygen or nitrogen or humidity) or in deprived media conditions. The level of selective pressure that is used can be determined by one of skill in the art. This can be done, for example, by performing a kill curve experiment, where control cells and cells that comprise resistance markers or genes are tested with increasing levels, doses, concentrations or treatments of the selective pressure and the ranges that selected against the negative cells only or preferentially over a desired range of time (e.g., from 1 to 24 hours, 1 to 3 days, 3 to 5 days, 4 to 7 days, 5 to 14 days, 1 to 3 weeks, 2 to 6 weeks). The exact levels, concentrations, doses, or treatments of selective pressure that can be used depends on the cells that are used, the desired properties themselves, the markers, factors or genes that confer resistance or tolerance to the selective pressure as well as the levels of the desired properties that are desired in the cells that are selected and one of skill in the art would readily appreciate how to determine appropriate ranges based on these considerations.

The culturing can be performed in a suitable culture medium in a suitable container, including but not limited to a cell culture plate, a flask, or a fermentor. In some embodiments, the culture medium is an aqueous medium comprising assimilable carbon, nitrogen and phosphate sources. Such a medium can also include appropriate salts, minerals, metals and other nutrients. In some embodiments, in addition to the selection agent, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter). Materials and methods for the maintenance and growth of cell cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process. In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density ($OD_{600}$) of between 0.01 and 400 in the fermentation vessel or container in which the culturing is being carried out. In other embodiments, the culturing is carried for a period of at least 12, 24, 36, 48, 60, 72, 84, 96 or more than 96 hours. In some embodiments, the culturing is carried out for a period of between 3 and 20 days. In some embodiments, the culturing is carried out for a period of 1, 2, 3, 4, 5, 6, 7, 8, 9, 10, 11, 12, 13, 14, 15, 16, 17, 18, 19, 20 or more than 20 days.

In some embodiments of the methods described herein, the methods further comprise the step of eliminating the circularized extrachromosomal vector from the host cell, for example, once a selected host cell has been identified as comprising the desired genomic integration(s). Plasmid-based systems generally require selective pressure on the plasmids to maintain the foreign DNA in the cell. In some embodiments, elimination of a plasmid encoding the selective marker from a selected cell can be achieved by allowing the selected cells to undergo sufficient mitotic divisions such that the plasmid is effectively diluted from the population. Alternatively, plasmid-free cells can be selected by selecting for the absence of the plasmid, e.g., by selecting against a counter-selectable marker (such as, for example, URA3) or by plating identical colonies on both selective media and non-selective media and then selecting a colony that does not grow on the selective media but does grow on the non-selective media.

In any of the methods described herein, disruption of a target site in a host cell genome occurs when the RNA-guided DNA endonuclease cleaves the target site in the genome of a host cell. The amount of time required for integration of a donor DNA molecule once the RNA-guided DNA endonuclease as cleaved the target site will vary. For example, the period of time encompassed can be at least 6, 12, 24, 36, 48, 60, 72, 96 or more than 96 hours of cell culture, beginning at the point at which the host cell is contacted with the first linear nucleic acid, the second linear nucleic acid and the donor DNA molecule, whether the nucleic acid encoding the RNA-guided DNA endonuclease is integrated into the host cell genome or simultaneously introduced into the host cell with the first linear nucleic acid, the second linear nucleic acid and the donor DNA molecule.

Guide RNAs

As used throughout, a guide RNA (gRNA) sequence is a sequence that interacts with an RNA-guided DNA endonuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. Each gRNA contains a gRNA scaffold sequence that binds to the RNA-guided DNA endonuclease that does not comprise the DNA targeting sequence. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%).

RNA-guided DNA Endonucleases

Any RNA-guided DNA endonuclease can be used in the methods provided herein. In some embodiments, the RNA-guided DNA endonuclease is an active Cas9 endonuclease such that when bound to a target nucleic acid as part of a complex with a guide RNA, a double strand break is introduced into the target nucleic acid. In some embodiments, the double strand break is repaired by HDR to insert a donor DNA molecule into the genome of the host cell. Various Cas9 endonucleases can be used in the methods described herein. For example, a Cas9 nuclease that requires an NGG protospacer adjacent motif (PAM) immediately 3' of the region targeted by the guide RNA can be utilized. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to, those described in Esvelt et al. (*Nature Methods* 10: 1116-1121 (2013)).

In some cases, the Cas9 protein is a nickase, such that when bound to target nucleic acid as part of a complex with a guide RNA, a single strand break or nick is introduced into the target nucleic acid. A pair of Cas9 nickases, each bound to a different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," Cell 154(6): 1380-1389 (2013)).

Host Cells

In another embodiment, provided herein is a modified host cell generated by any of the methods of disrupting a target site in a host cell genome or genomically integrating one or more exogenous nucleic acids described herein. Populations of modified host cells generated by any of the methods provided herein are also provide. In a specific embodiment, a population of host cells wherein at least 5%, 10%, 15%, 20%, 25%, 30%, 35%, 40%, 45%, 50%, 55%, 60%, 65%, 70%, 75%, 80%, 85%, 90% or higher or any percentage in between are altered using any of the methods provided herein is also provided.

Suitable host cells include any cell in which integration of a donor DNA molecule of interest into target site in the host cell genome is desired. In some embodiments, the host cell is a cell that is capable of performing homologous recombination. In other embodiments, the host cell is a cell that is capable of performing gap repair. In some embodiments, the host cell is a yeast cell. In some embodiments, the yeast cell is a Pichia cell. In specific embodiments, the Pichia cell is a Pichia pastoris cell. In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment. For a list of cell type suitable for integration of one or more donor DNA molecules using the methods described herein, see International Application Publication No. WO2015095804.

Methods of Producing a Protein of Interest

In another embodiment, provided herein are methods of producing a protein of interest. The methods comprising culturing a host cell comprising one or more integrated donor DNA molecules of interest encoding one or more proteins of interest under conditions suitable for production of the protein and recovering the protein produced by the host cell. In some embodiments, the protein of interest is a protein selected from the group consisting of an antibody, an enzyme, a hormone, a growth factor, an anticoagulant, blood factors, an engineered protein, an interferon, an interleukin, a thrombolytic, a viral protein or a bacterial protein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

This example provides results which demonstrate the use of CRISPR for simultaneous deletion and/or integration of one or multiple loci selected from the group consisting of BMT1, BMT2, BMT4, BMT4, PNO1, MNN4-1, MNN4-2, MNN4-3, PRB1, PEP4, AOX1, and DNL4, in *Pichia*. In brief, chimeric gRNAs were generated targeting unique sequences contained in the open reading frame (ORF) of BMT1, BMT2, BMT4, BMT4, PNO1, MNN4-1, MNN4-2, MNN4-3, PRB1, PEP4, AOX1, and DNL4. The gRNAs were transformed in various configurations into host cells expressing the Cas9 protein from the type II bacterial CRISPR system of *Streptococcus pyogenes*. Transformed colonies were screened by colony PCR (cPCR) for the replacement of one or multiple ORFs with a short linker sequence, or Herceptin antibody sequence.

Materials and Methods

Host Strain

A wild type NRRL Y-48124 *Komagataella pastoris* (*Pichia pastoris*) strain was used in this study. Cas9 was constitutively expressed under a *Pichia* pPGK1 promoter and integrated into the YKU70 locus to disable NHEJ. The resulting strain was Y486. AOX1 was deleted from Y486 resulting in Y651, which was Mut$^s$ on methanol. The anti-Her2 antibody Herceptin sequence was integrated at the PEP4 locus in Y651 under the control of the pAOX1 promoter. The strain was Y324. Deleting AOX1 and integrating Herceptin sequence at the PEP4 locus were achieved by targeted integration using CRISPR. The quintuplex engineering was done in the Herceptin strain background.

Loci Deleted and Guide RNA Sequences

Candidate CRISPR targets inside the targeted ORFs were identified based on the presence of a PAM sequence N$_{(19)}$NGG. The NGG sequence is referred to as a PAM sequence and the 8 base pairs of DNA proceeding the PAM sequence are especially important for enforcing specificity (See, for example, International Application Publication No. WO2015/095804). The guide RNA sequences are set forth in Table 1.

TABLE 1 guide RNA sequences

| Locus | gRNA sequence (NGG omitted) | SEQ ID NO: |
|---|---|---|
| BMT1/BMT2 | AAAGCTAGAGTTACCGTAA | 1 |
| BMT3 | TCAACTGCAGTCTTGATAA | 2 |
| BMT4 | GTGTGAACAGAGCCATGTA | 3 |
| MNN4-1/PNO1 | ATTTGGAGATTTTGCGCTA | 4 |
| MNN4-2 | TTCTGGAGAGCACTATGAC | 5 |
| MNN4-3 | AACCCTAAGAATCTGGCTC | 6 |

TABLE 1-continued guide RNA sequences

| Locus | gRNA sequence (NGG omitted) | SEQ ID NO: |
|---|---|---|
| PRB1 | TCAACAAGTACTTATATGA | 7 |
| PEP4 | ATTTTATGTCTCAGCAAGA | 8 |
| AOX1 | GACATGGCTCCTATGGTTT | 9 |
| DNL4 | TGGCTGAAATTAGGTAAAG | 10 |
| Upstream of VTH1 | AGAAAATAAAGAGTTTCTA | 11 |
| Upstream of CNE1 | TAGATGCAGTAGGATAGGG | 12 |
| Upstream of ECM10 | GTCCACTAACTACCTTTCG | 13 |
| Upstream of ERO1 | AAAGATAGGGAAAAGGAAA | 14 |

Guide RNA Delivery Modes gRNA Cassette

The guide RNA cassette used in these studies contains an RNA polymerase II promoterpHTA1 from *Pichia* (Weninger et al., 2016), a 19 mer guide RNA sequence, a structural guide RNA sequence, and an ADH1 terminator from *Saccharomyces*. The guide RNA is flanked by hammerhead (HH) and hepatitis delta virus (HDV) ribozyme sequences. The HH ribozyme is also flanked with a short 6 bp linker "TCAGAT" (SEQ ID NO: 15) to facilitate removal of the HH ribozyme (Weninger et al., 2016). Sequences of each element are listed below.

Generation of gRNA Vector for Pichia

Standard pRS4XX-series 2µ, vectors (Sikorski and Hieter, *Genetics* 12291): 19-27 (1989)) were used as the starting material. 2 µ region was replaced with Pichia ARS1 region (See the sequence listing). gRNA expression cassette targeting *Saccharomyces* ADH4 was cloned into the resulting vector between SalI and BamHI. The resulting plasmid is named pAM1114_PPARS1_pHTA1_ScADH4. The primers used in this work is listed in Table 2. The new vector was linearized with EcoRV for gap repair with gRNA cassette in transformation.

TABLE 2

Primers used in generating gRNA delivery components

| Primer name | Description | Sequence |
|---|---|---|
| HJ2299 | Linear pRS4XX REV | CGCGAATGTTCCCCCAGCTTATCTCGACAGGTGGCACTTTTCGGGGAAATGTGCG (SEQ ID NO: 16) |
| HJ2301 | Linear pRS4XX FOR | GACCAAAATAAGTAAATATTAATTGTCGAATACTTTCTAGAGAATAGGAACTTCGG (SEQ ID NO: 17) |
| HJ2300 | *Pichia* ARS1 FOR | CGCACATTTCCCCGAAAAGTGCCACCTGTCGAGATAAGCTGGGGGAACATTCGCG (SEQ ID NO: 18) |
| HJ2302 | *Pichia* ARS1 REV | CCGAAGTTCCTATTCTCTAGAAAGTATTCGACAATTAATATTTACTTATTTTGGTC (SEQ ID NO: 19) |
| HJ2353 | gRNA ScADH4 no tADH1 FOR | CCCCTCGAGGTCGACGGTATC (SEQ ID NO: 16) |
| HJ2357 | gRNA ScADH4 no tADH1 REV | AAAATCATAAATCATAAGAAATTCGCGTCCCATTCGCCATGCCGAAGCATGTTGCC (SEQ ID NO: 20) |

TABLE 2-continued

Primers used in generating gRNA delivery components

| Primer name | Description | Sequence |
|---|---|---|
| HJ2358 | tADH1 FOR | GGCAACATGCTTCGGCATGGCGAATGGGACGCGAATTTCTTATGATTTATG ATTTT (SEQ ID NO: 21) |
| HJ2359 | tADH1 REV | CTAGAACTAGTGGATCCCCCGGGCGCTGGAGTTAGCATATCTACAATTGGG TG (SEQ ID NO: 22) |
| HJ2477 | Linear pAM1114_PPARS1_pHTA1_ScADH4 REV | GGGAGGACTCTCGTTTCCTATG (SEQ ID NO: 23) |
| HJ2442 | Linear pAM1114_PPARS1_pHTA1_ScADH4 FOR | TTTTAGAGCTAGAAATAGCAAG (SEQ ID NO: 24) |

FOR = a forward primer; REV = a reverse primer

Generation of linear gRNAs for targeted integrations

Targeted PEP4 deletion
Stitched linear gRNA cassette

Template pAM1114_PPARS1pHTA1_ScADH4 plasmid was used in the following PCR reactions. HJ2353 and HJ2463 primers (Table 3) were used to generate the first part of the PEP4 gRNA expression cassette. HJ2455 and HJ2354 primers (Table 3) were used to generate the 2nd part of the PEP4 gRNA expression cassette. The two PCR products were gel extracted and stitched together using PCR. The stitched product was gel extracted and used as linear gRNA cassette in transformations.

Amplification from Cloned gRNA Vector

Two parts of the gRNA cassette were amplified using the same primers as above. The PCR fragments were cleaned and cloned into pAM1114_PPARS1_pHTA1_ScADH4 (generated using the method described above) in *Saccharomyces* according to methods described in U.S. Pat. Nos. 8,110,360, 8,221,982, and 8,332,160. Plasmid was extracted from yeast and transformed into *E. coli*. Clones were sequence verified. The linear gRNA fragment was amplified from the clones using HJ2353 and HJ2354 primers (Table 3). The PCR product was gel extracted or cleaned using the Zymo DNA Clean & Concentrator™ kit (Zymo Research (Irvine, Calif.).

Generation of Linear Donor DNA

Linear donor DNAs comprise about 1 kb upstream and downstream homology regions targeting each ORF, flanking a central linker (CGCTCGTCCAACGCCGGCGGACCT), (SEQ ID NO: 29) and were generated by the methods of polynucleotide assembly described in U.S Pat. No. 8,221, 982. Donor DNA sequences for integration into the loci listed in the above are listed in the sequence listing.

Simultaneous Deletion of ORF and Integration of a Short Linker Sequence Using CRISPR For each loci or ORF of interest, a linear donor DNA, a linear gRNA, and a linear gRNA vector backbone (~200ng each) were co-transformed into each Cas9 expressing strain using an electroporation method (See, *Pichia* Protocols, Chapter 3. by D. R. Higgins and J. Cregg, eds. In Methods in Molecular Biology, vol. 103, The Humana Press, Totowa, N.J., 1998). Cells were recovered overnight before plating to selective, antibiotic-containing (nourseothricin, 50 mg/L) media to maintain the gRNA or marker plasmid. Marker-less integrations were scored as positive if colony PCR (cPCR) using primers binding upstream of the 5′ integration flank and to the integrated linker sequence (Table 4) produced the correct amplicon, a result indicative of a targeted integration event. The 3′ integration and disappearance of open reading frame (ORF) sequences were also checked with cPCR.

TABLE 3

Primers for PEP4 gRNAs

| Primer name | Description | Sequence |
|---|---|---|
| HJ2353 | 1$^{st}$ part gRNA FOR | CCCCTCGAGGTCGACGGTATC (SEQ ID NO: 25) |
| HJ2463 | 1$^{st}$ part gRNA REV | TCTTGCTGAGACATAAAATCATCTGAGACGAGCTTACTCGTTTCGTCCTCAC (SEQ ID NO: 26) |
| HJ2455 | 2$^{nd}$ part gRNA FOR | ATTTTATGTCTCAGCAAGAGTTTTAGAGCTAGAAATAGCAAGTTAAAATAAG (SEQ ID NO: 27) |
| HJ2354 | 2$^{nd}$ part gRNA REV | CTAGAACTAGTGGATCCCCCG (SEQ ID NO: 28) |

TABLE 4

Primer sequences for confirming integration into ORFs

| Primer name | Decription | Sequence | SEQ ID NO: |
|---|---|---|---|
| HJ2338 | AOX1 locus US FOR | TAACAGTTATTATTCGAGATCTA | 30 |
| HJ2674 | DNL4 locus US FOR | GGTACCATACTTCTCCACCG | 31 |
| HJ2417 | PEP4 locus US FOR | TTCGAAACTGCAGCTAGCAA | 32 |
| HJ2425 | BMT1/BMT2 locus US FOR | CCATTGTTGCCGATAACTGTTG | 33 |
| HJ2575 | BMT3 locus US FOR | CGGTATCGCTGCTTTCTTTA | 34 |
| HJ2581 | BMT4 locus US FOR | CAATAATCAATGCAGCCCAG | 35 |
| HJ2605 | MNN4-1/PNO1 locus US FOR | GAAAAGGGTAGTGAAAGGAAAG | 36 |
| HJ2593 | MNN4-2 locus US FOR | GCTAATTACGTACCAGAACC | 37 |
| HJ2411 | MNN4-3 locus US FOR | TTGACACCTTGGATAAAAGGG | 38 |
| HJ2599 | PRB1 locus US FOR | CAGAATAACTTCATGACTGC | 39 |
| HJ2794 | VTH1 locus US FOR | AGTGACGCCAACAATACCCATGA | 40 |
| HJ2778 | CNE1 locus US FOR | TTGTCCCACTTTGAATAATCG | 41 |
| HJ2862 | ECM10 locus US FOR | GGAGTTTTTGGGCTAGGGGTTTG | 42 |
| HJ2782 | ERO1 locus US FOR | GCTGAGCACTTCAGTCTTACG | 43 |

"US" = upstream; "FOR" = a forward primer

Results

Up to 100% targeting efficiency was obtained from single, double, and triple integrations. Very high efficiencies were achieved from quadruple (47%) and quintuple (31%) integrations (see Table 5 below). This is a great improvement from the currently known *Pichia* CRISPR technology.

As shown in Table 5, using the methods provided herein, high efficiency, targeted and marker-less single, double, triple, quadruple, and quintuple integrations in a host cell genome were achieved by using CRISPR in host cells, including *Pichia*. To summarize, in this example, one or more targeted integrations were achieved by transforming host cells (e.g., *Pichia* cells) containing a nucleic acid encoding Cas9 under the control of a medium strength promoter pPGK1 from *Pichia* with linear Nat-marked vector backbone, guide RNAs under a constitutive promoter, and donor DNAs. The guide RNA cassette contains an RNA polymerase II promoterpHTA1 from *Pichia*, a 19mer guide RNA sequence specific for a gene or loci of interest, a structural guide RNA sequence that binds to Cas9, and an ADH1 terminator from *Saccharomyces*. The guide RNA is flanked by hammerhead (HH) and hepatitis delta virus (HDV) ribozyme sequences. The HH ribozyme is also flanked with a short 6 bp linker (TCAGAT) to facilitate releasing of the gRNA.

TABLE 5

Summary of CRISPR targeting efficiency

| Starting Host strain | Targeting loci and integration | MS# | Multiplexing | Efficiency |
|---|---|---|---|---|
| Y486 | AOX1 deletion resulting in Y651 | MS530 | Single | 90% |
| Y486 | DNL4 deletion | | Single | 100% |
| Y486 | PEP4 deletion | | Single | 100% |
| Y551 | PEP4 deletion with Herceptin integration at PEP4 resulting in Y324 | MS841 | Single | 100% |
| Y324 | BMT1/BMT2/BMT3 deletion | MS061, MS648 | Double | 100% |
| Y324 | MNN4-1/PN01/MNN4-2 deletion resulting in Y136 | MS056, MS652 | Double | 100% |
| Y324 | BMT1/BMT2/BMT3/BMT4 deletion | MS061, MS648, MS649 | Triple | 73% |
| Y324 | MNN4-1/PNO1/MNN4-2/MNN4-3 deletion | MS056, MS652, MS653 | Triple | 100% |
| Y136 | BMT1/BMT2/BMT3 deletion | MS061, MS648 | Double | 100% |
| Y136 | PRB1/MNN4-3 deletion | MS655, MS653 | Double | 100% |
| Y136 | BMT1/BMT2/BMT3/BMT4 deletion | MS061, MS648, MS649 | Triple | 100% |
| Y136 | BMT1/BMT2/BMT3/MNN4-3 deletion | MS061, MS648, MS653 | Triple | 100% |

TABLE 5-continued

Summary of CRISPR targeting efficiency

| Starting Host strain | Targeting loci and integration | MS# | Multiplexing | Efficiency |
|---|---|---|---|---|
| Y136 | BMT1/BMT2/BMT3/MNN4-3/PRB1 deletion | MS061, MS648, MS653, MS655 | Quadruple | 47% |
| Y136 | BMT1/BMT2/BMT3/BMT4/MNN4-3/PRB1 deletion | MS061, MS648, MS649, MS653, MS655 | Quintuple | 31% |
| Y324 | pTDH3>VTH1/pTDH3>CNE1/pTDH3>ECM10/pTDH3>ERO1 | MS637, MS628, MS766, MS632 | Quadruple | 20% |

Using the methods provided herein, high efficiency, targeted and marker-less single, double, triple, quadruple, and quintuple integrations in a host cell genome were achieved by using CRISPR in host cells, including *Pichia*. This was achieved by transforming host cells (e.g., *Pichia* cells) containing a nucleic acid encoding Cas9 under the control of a medium strength promoter pPGK1 from *Pichia* with linear Nat-marked vector backbone, guide RNAs under a constitutive promoter, and donor DNAs. The guide RNA cassette contains an RNA polymerase II promoter pHTA1 from *Pichia* (Weninger et al., 2016), a 19mer guide RNA sequence, a structural guide RNA sequence, and ADH1 terminator from *Saccharomyces*. The guide RNA is flanked by hammerhead (HH) and hepatitis delta virus (HDV) ribozyme sequences. The HH ribozyme is also flanked with a short 6 bp linker "TCAGAT" to facilitate releasing of the gRNA (Weninger et al., 2016).

Production of Antibodies

Construction of Antibody Expression Cassettes

The BIIB antibody sequences include heavy chain (HC) and light chain (LC) polypeptides. To drive secretion of the construct from the yeasts, the full length, 89 amino acid pre-pro-alpha factor secretion leader from *Saccharomyces cerevisiae* (Waters et al., 1988, *J. Biol. Chem.* 1988 263(13): 6209-14) was added to the amino termini of both HC and LC. The amino acid sequences of BIIB, Herceptin, and Rituxan were codon-optimized according to host species preference using a codon optimization algorithm, and chemically synthesized by Gen9 (now Ginkgo Bioworks, Boston, Mass., USA), Twist (San Francisco, Calif., USA), or Integrated DNA technologies (IDT, San Diego, Calif., USA). DNA expression constructs were cloned in a variety of configurations under strong constitutive native and/or inducible promoters in each host: as a single 2A peptide linked "operon" (Chng et al., 2015, MAbs. 7(2):403-12), as convergent split cassettes at the same locus, or as cassettes at different loci. Various other secretion tags, like those from *S. cerevisiae* pre-pro-alpha factor or invertase, *Pichia* Kar2, or *K. marxianus* inulin were also tested for their ability to direct antibody secretion in yeasts.

DNA assembly and Transformations

Multi-component DNA constructs were generated using DNA assembly methods as previously described (De Kok et al. (2014) *ACS Synth. Biol.* 21;3(2):97-106. doi: 10.1021/sb4001992; Serber et al., U.S. Pat. No. 8,221,982), and transformed into each host using methods described below.

For *Pichia pastoris* host cells, linear fragments of donor DNA cassettes containing ~1.0 kb of upstream and downstream homology of targeting loci to *Pichia* genome, guide RNA (gRNA), and vector containing *Pichia* ARS1 sequence and homology regions with gRNA were transformed into *Pichia* host strains expressing Cas9 (Weninger et al., *J. Biotech.* 235:139-149 (2016); Horwitz et al. *Cell Syst.* Jul 29;1(1):88-96 (2015)). The transformation protocol was adapted from Higgins and Cregg's electroporation method (Higgins and Cregg, *Methods Mol Biol.* 103:1-15 (1998)).

Media and strain cultivation

Production of antibodies from four yeast hosts was conducted in cultures in 96-well microtiter plates (1.1 or 2.2 mL) at 1,000 rpm shaking with 80% relative humidity in the media described below. Cells were typically grown for 1-2 days (pre-culture phase) before being diluted or spun down and resuspended in fresh media, and re-grown for 2-3 days (production phase). Cells were separated by centrifugation and supernatant samples were collected for future analyses. To produce large volume of cultures, cells were grown in 50 mL of media in 250 mL of flasks and shaken at 200 rpm. Culturing conditions for each species are listed below.

Protein A Purification

Supernatant samples from antibody production cultures were purified and concentrated using Protein A tip columns (PhyNexus, San Jose, Calif., USA).

Semi-quantitative Antibody Titer Measurement by Dot Blot

Dot blot analysis was carried out using the Minifold I 96-Well System (GE Healthcare, Little Chalfont, UK) according to the manufacturer protocol. Supernatants were collected from cultures grown under production conditions. Detection was performed using IRDye® 800CW goat anti-human IgG (H +L) antibody (LI-COR, Lincoln, Nebr., USA) as both the primary and secondary antibody and imaged on the Odyssey Infrared Imaging System (LI-COR, Lincoln, Nebr., USA).

EndoH Treatment

Endoglycosidases treatment was done using Endo $H_f$ (New England Biolabs, Cat. No. P0703S) according to the manufacturer's instructions. For non-reducing samples, 1× Glycoprotein Denaturing Buffer was replaced with 5% SDS solution.

Western Blot

All monoclonal antibody samples were mixed with NuPAGE LDS Sample Buffer (Thermofisher, Cat. No. NP008) and denatured at 70° C. for 10 min before running non-reduced samples on 3-8% Tris-Acetate precast protein gels (Thermofisher, Cat. No. EA0375). For reduced samples, NuPAGE Sample reducing Buffer (Thermofisher, Cat. No. NP009) was used as reducing agent. Reduced samples were denatured at 70° C. for 10 minutes and then run on 4-12% Bis-Tris precast protein gels (Thermofisher, Cat. No. NP0321). For investigation BIIB degradation by intracellular cell lysate, samples were run on a 48-well E-PAGE gel using the iBlot system (Thermofisher). For Western Blot analysis, Goat anti-human IgG (H+L) (LiCor, Cat. No. 925-32232) was used at a 1:10,000 dilution to detect heavy chain, light chain or full length antibody.

*P. pastoris*. Pichia colonies were inoculated in 360 µL of BMGY 1% glycerol (2% Bacto peptone, 1% Bacto yeast extract, 100 mM potassium phosphate pH 6.0, 1.34% yeast nitrogen base without amino acids, 0.4 µg/mL Biotin, and 1% Glycerol) and grown in 1.1 mL 96-well plates for 24 hours at 30° C. Cells were then spun down and resuspended in 360 µL BMMY (2% Bacto peptone, 1% Bacto yeast extract, 100 mM potassium phosphate, pH 6.0, 1.34% yeast nitrogen base without amino acids, 0.4 µg/mL Biotin, 0.5% v/v methanol) and grown at 30° C. for 72 hours. 1% v/v methanol was added to production plates after 24 and 48 hours in BMMY.

We cloned expression constructs for Herceptin and Rituxan for *Pichia*. Constructs were designed as convergent, split expression cassettes using the shorter pre-alpha leader in place of the pre-pro-alpha leader previously used. We chose this shorter leader to match constructs used in successful published efforts (Zha, 2013), though the longer leader has also been used successfully as well (Kozlov and Yagudin, 2008). We have also used the same secretion tag Kar2 for Rituxan as published by Glycofi (Li et al., 2006) in *Pichia*. All sequences were codon optimized for each host using codon optimization algorithms. Using these new constructs, we were able to detect full-length IgG expression in *Pichia*.

We also cloned expression constructs for BIIB antibody (CD23 binding antibody) for *Pichia*. The heavy chain (HC) and light chain (LC) sequences of the BIIB antibody can be found as SEQ ID NO: 18 in PCT publication WO2009043051 as SEQ ID NO: 18 and SEQ ID NO:4, respectively. However, for this construct, the full-length IgG expression was not detected, although antibody fragments were detected.

Table 6 below provides a summary of *Pichia pastoris* (PP) producing BIIB, Herceptin and Rituxan antibodies in a shake plate. HC/LC, HC and LC sequences are split in two DNA constructs and integrated at the same locus by homology recombination. All BIIB and Herceptin/Rituxan sequences were fused to *S. cerevisiae* pre-pro-alpha and pre-alpha secretion tag, respectively, unless noted. NA, not available. BDL, below detection limit of Octet.

In some strains, various strain engineering strategies were attempted to increase full-length antibody secretion, e.g., overexpressing genes responsible for protein folding and secretion (CNE1, HAC1, ERO1, KAR2, etc.) or deleting proteases (pep4 and/or prb1). In some instances, the methods described herein were used for simultaneous deletion and/or integration of an antibody construct, one or more overexpression constructs, and/or one or more deletion constructs at multiple loci.

TABLE 6

| Species | Antibody | Strain | Engineering | Octet Titer (pg/mL) | Full-length antibody secreted |
|---|---|---|---|---|---|
| PP | None | Y486pp | yku70Δ; Prepared for multiplexing | 0.00 ± 0.00 | No |
| PP | BIIB | Y242 | aox1Δ::pAOX1>HC_2A_LC, yku70Δ | 5.40 ± 1.14 | No |
| PP | BIIB | Y800 | aox1Δ::pAOX1>HC_2A_LC, yku70Δ, dnl4Δ | 5.56 ± 0.98 | No |
| PP | BIIB | Y126 | aox1Δ::pAOX1>HC_2A_LC; yku70Δ, dnl4Δ, pTDH3>VTH1 | 9.77 ± 0.41 | No |
| PP | BIIB | Y829 | aox1Δ::pAOX1>HC_2A_LC, dnl4Δ, pTDH3>VTH1, pTDH3>CNE1, pTDH3>ECM10, pTDH3>ERO1 | 11.17 ± 0.06 | No |
| PP | Herceptin | Y324 | pep4Δ::pAOX1>HC/LC, aox1Δ, yku70Δ | 8.67 ± 0.68 | Yes |
| PP | Herceptin | Y676 | pep4Δ::pAOX1>HC/LC, aox1Δ, yku70Δ, pTDH3>CNE1, pTDH3>ECM10, pTDH3>ERO1, pTDH3>VTH1 | 11.95 ± 0.84 | Yes |
| PP | Rittman | Y328 | pep4Δ::pAOX1>HC/LC, yku70Δ | BDL | Yes |

Figure 1B:
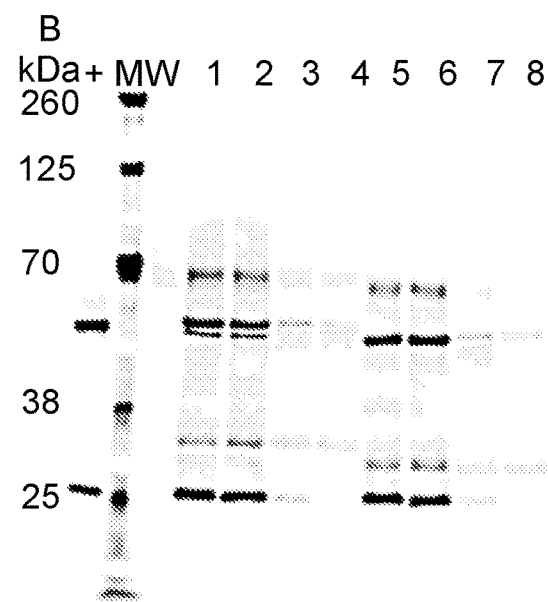

Protease-deleted (pep4Δ) *P. pastoris* strains expressed both Herceptin and Rituxan in full-length (FIGS. 1A and 1B). Under non-reducing conditions, a diffuse 150 kDa+ band matching the standard is observed for both constructs cloned with either the pre-alpha leader, or alternatively, the Kar2 leader (FIG. 1A). In addition, a potential kexin protease site in the LC construct was mutated ("KR to TR"), but had no effect (lanes 2, 4, 6 and 8), and we conclude that LC kexin degradation is not a major factor in *P. pastoris*. Pre-treatment of samples with Endo $H_f$ to remove glycosylation chains (lanes 5-8) sharpens the full-length band. It is clear that Herceptin titers are much higher than Rituxan titers. This is likely due to the different in secretion tags and antibody sequences. When the samples were run under reducing conditions, the proper HC and LC bands are observed (FIG. 1B). Without treatment, a doublet is visible for the HC band, which potentially represents aglycone and glycosylated forms. Endo $H_f$ treatment shifts the higher molecular weight band downward into a single lower molecular weight band, confirming glycosylation (FIG. 1B, Lanes 1 and 2 versus 5 and 6).

FIGS. 1A and 1B illustrate secretion of full-length Herceptin and Rituxan by engineered *P. pastoris* strains. Protein A purified samples were assayed by Western Blot under non-reducing (A) and reducing (B) conditions. 1-4, Protein A purified samples; 5-8, Protein A purified and Endo $H_f$ treated samples. 1 and 5, Herceptin with pre-alpha secretion leader sequence; 2 and 6, Herceptin with pre-alpha secretion leader sequence and KR mutated to TR in LC; 3 and 7, Rituxan with Kar2 leader sequence; 4 and 8, Rituxan with Kar2 sequence and KR mutated to TR in LC. MW, molecular weight marker, with quantities on the left of each gel. +, BIIB antibody standard.

Overexpression constructs of VTH1, CNE1, ECM13, and ERO1 were consolidated in a Herceptin expressing strain to determine whether they improved antibody expression as they had with the BIIB expressing strains (Table 6). The resulting strain Y676 has shown about 40% higher titer than Y324 (Table 6), which demonstrated that the genetic tricks to improve BIIB expression can also improve Herceptin expression.

Figure 2:
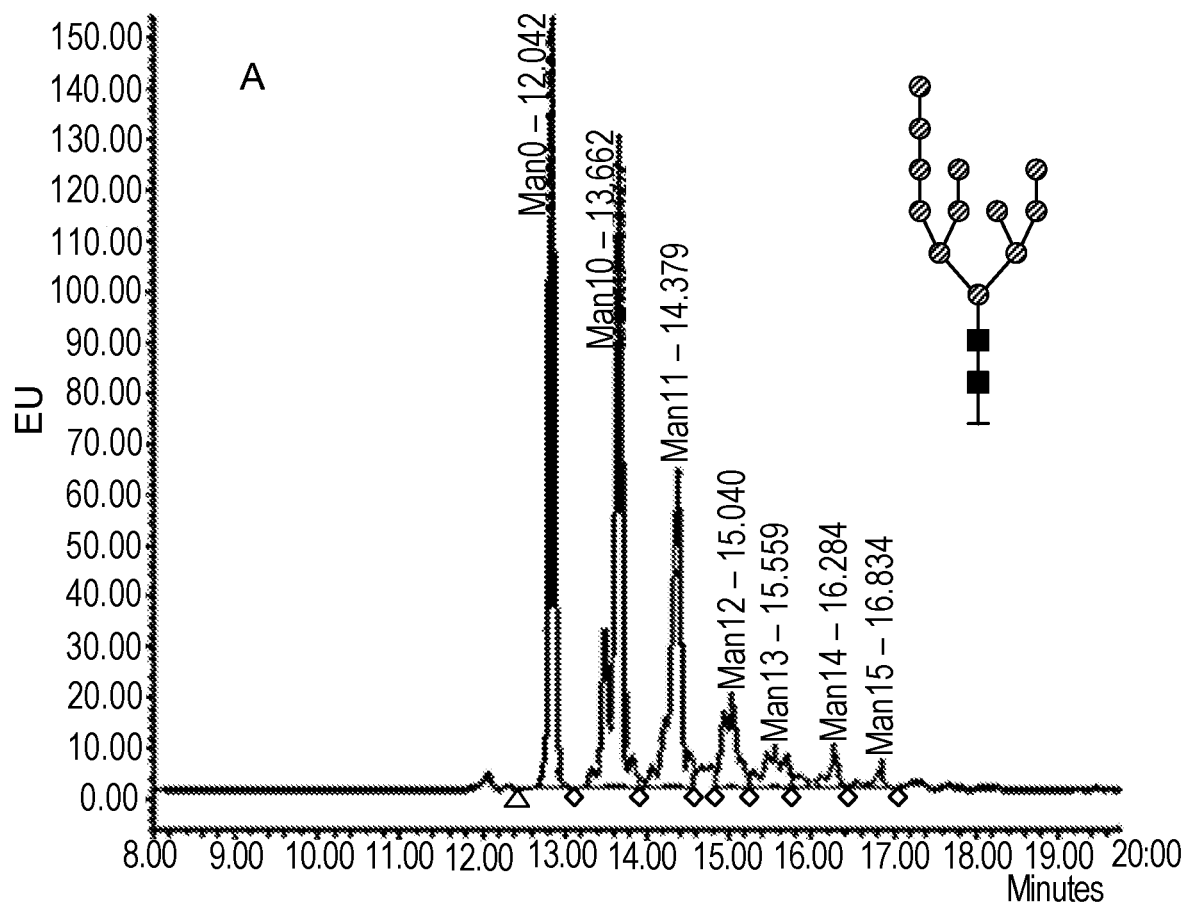
FIG. 2 shows the results of mass spectrometry analysis of samples from Herceptin producing *P. pastoris*. The samples were analyzed to determine the N-glycan profile of Herceptin produced by *P. pastoris*. Mass spectrometry results were as expected, with the Herceptin produced by *P. pastoris* having a glycosylation pattern with high mannose content.

Samples from Herceptin producing *P. pastoris* was analyzed by mass spectrometer for N-glycan profile. Mass spectrometer result was expected for glycosylation pattern with high mannose in *P. pastoris*. N-Glycan analysis of Herceptin producing *P. pastoris* is shown in FIG. 2.

The results shown in the Examples section illustrate that *Pichia* is highly engineerable, allowing multiple genomic integration of heterologous nucleic acids simultaneously. Compared to CHO cells which have a doubling time of about 19-24 hours and a total genetic engineering cycling time (from one transformation to the next transformation) of about three months, *Pichia* has a cell population doubling time of about 2 hours and a total cycling time of about two weeks with the compositions and methods provided in the present invention. The compositions and methods provided herein provide a large step forward in our ability to engineer *Pichia* for the production of new biomolecules.

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

INFORMAL SEQUENCE LISTING

```
ARS1 (SEQ ID NO: 44)
TCGAGATAAGCTGGGGGAACATTCGCGAAAATGAAACAAGTCGGCTGTTATAGTATATTT
ATTATAATATTGAAAGATCTCAAAAGACTACTTATTTTTGAATGAACCAAGTATGAAATC
AACCTATTTGGGGTTGACCAAAATAAGTAAATATTAATTGTCGA pHTA1 (SEQ ID NO: 45)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAA

HH (SEQ ID NO: 46)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAA

HDV (SEQ ID NO: 47)
GGCCGGCATGGTCCCAGCCTCCTCGCTGGCGCCGGCTGGGCAACATGCTTCGGCATGGCG
AATGGGAC 6 bp linker flanking 5' and 3' of HH (reverse complimentary sequence) (SEQ
ID NO: 48)
ATCTGA and TCAGAT Structural gRNA (SEQ ID NO: 49)
TTTTAGAGCTAGAAATAGCAAGTTAAAATAAGGCTAGTCCGTTATCAACTTGAAAAAGTG
GCACCGAGTCGGTGGTGC tADH1 (SEQ ID NO: 50)
GCGAATTTCTTATGATTTATGATTTTTATTATTAAATAAGTTATAAAAAAAATAAGTGTA
TACAAATTTTAAAGTGACTCTTAGGTTTTAAAACGAAAATTCTTATTCTTGAGTAACTCT
TTCCTGTAGGTCAGGTTGCTTTCTCAGGTATAGCATGAGGTCGCTCTTATTGACCACACC
TCTACCGGCATGCCGAGCAAATGCCTGCAAATCGCTCCCCATTTCACCCAATTGTAGATA
TGCTAACTCCAGC
``` gRNA expression cassette targeting *Saccharomyces* ADH4 used to construct
gRNA vector backbone for *Pichia* SEQ ID NO: 51)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAAATCTGACTGATGAGTCCGTGAGGACGAAACGAGTAAGCTCGTCTCAGATG
GATTTGATCAATGAAAGCTGTTTTAGAGCTAGAAATAGCAAGTTAAAATAAGGCTAGTCC
GTTATCAACTTGAAAAAGTGGCACCGAGTCGGTGGTGCGGCCGGCATGGTCCCAGCCTCC
TCGCTGGCGCCGGCTGGGCAACATGCTTCGGCATGGCGAATGGGACGCGAATTTCTTATG
ATTTATGATTTTTATTATTAAATAAGTTATAAAAAAAATAAGTGTATACAAATTTTAAAG
TGACTCTTAGGTTTTAAAACGAAAATTCTTATTCTTGAGTAACTCTTTCCTGTAGGTCAG
GTTGCTTTCTCAGGTATAGCATGAGGTCGCTCTTATTGACCACACCTCTACCGGCATGCC
GAGCAAATGCCTGCAAATCGCTCCCCATTTCACCCAATTGTAGATATGCTAACTCCAGC gRNA expression cassette targeting *Saccharomyces* ADH4 exclud-
ing tADH1 ordered
from IDT (SEQ ID NO: 52)
CCCCTCGAGGTCGACGGTATCGATTGTTGTAGTTTTAATATAGTTTGAGTATGAGATGGA
ACTCAGAACGAAGGAATTATCACCAGTTTATATATTCTGAGGAAAGGGTGTGTCCTAAAT
TGGACAGTCACGATGGCAATAAACGCTCAGCCAATCAGAATGCAGGAGCCATAAATTGTT
GTATTATTGCTGCAAGATTTATGTGGGTTCACATTCCACTGAATGGTTTTCACTGTAGAA
TTGGTGTCCTAGTTGTTATGTTTCGAGATGTTTTCAAGAAAAACTAAAATGCACAAACTG
ACCAATAATGTGCCGTCGCGCTTGGTACAAACGTCAGGATTGCCACCACTTTTTTCGCAC
TCTGGTACAAAAGTTCGCACTTCCCACTCGTATGTAACGAAAAACAGAGCAGTCTATCCA
GAACGAGACAAATTAGCGCGTACTGTCCCATTCCATAAGGTATCATAGGAAACGAGAGTC
CTCCCCCCATCACGTATATATAAACACACTGATATCCCACATCCGCTTGTCACCAAACTA
ATACATCCAGTTCAAGTTACCTAAACAAATCAAAATCTGACTGATGAGTCCGTGAGGACG
AAACGAGTAAGCTCGTCTCAGATGGATTTGATCAATGAAAGCTGTTTTAGAGCTAGAAAT
AGCAAGTTAAAATAAGGCTAGTCCGTTATCAACTTGAAAAAGTGGCACCGAGTCGGTGGT
GCGGCCGGCATGGTCCCAGCCTCCTCGCTGGCGCCGGCTGGGCAACATGCTTCGGCATGG
CGAATGGGACTTTTTTTGTTTTTTATGTCTGCCCGGGGGATCCACTAGTTCTAG BMT1/BMT2 DELETION MS061 (SEQ ID NO: 53)
GACGGCACGGCCACGCGTTTAAACCGCCAAGATGGTGATTTCCAGCGTTCGAAAAGCCTGTAGTACCCAGAATTT
TGATCAAAGTGTCCTCTTAGCCGTGGCATCCGCGGCTGTCATCTTGATCCTTCTTCGCATGAGCACTTACGTGAT
GCTGATAAGATGGGCACGCCACAACACTAGGGCCAAGACCTCGCCTAGTGGTGGCGACTATCTAAAGGGCTCACC
TAACACCTCTTTAGCGGGGATTGAAGACATTCATACACGAAGTCTGCTGTATGGGTCAGACGAGAAAATGCCGCA
ATCTAAAGAAGAACAAAGGTCCCACAATGCGAATCGTGATGGTGATAAATCATTGGCTCAGGTCAGTAGATTTGA
AATGCATGATAAACGCATATGGTGAGAGCCGTTCTGCACAACTAGATGTTTTCGAGCTTCGCATTGTTTCCTGCA
GCTCGACTATTGAATTAAGATTTCCGGATATCTCCAATCTCACAAAAACTTATGTTGACCACGTGCTTTCCTGAG
GCGAGGTGTTTTATATGCAAGCTGCCAAAAATGGAAAACGAATGGCCATTTTTCGCCCAGGCAAATTATTCGATT
ACTGCTGTCATAAAGACAGTGTTGCAAGGCTCACATTTTTTTTAGGATCCGAGATAAAGTGAATACAGGACAGC
TTATCTCTATATCTTGTACCATTCGTGAATCTTAAGAGTTCGGTTAGGGGGACTCTAGTTGAGGGTTGGCACTCA
CGTATGGCTGGGCGCAGAAATAAAATTCAGGCGCAGCAGCACTTATCGATGCATGCAAGGCGAGAAAAATAAAGA
ACAAAAACACACCTTGCTAAGACCACAACCTTTCAAATTTTGAGATTGTTATTCTTTCATCCTAAAACACCACCG
TCCTATCTCTTGGGAACGTACATATCATTGAGCTTGGTTCATTGATACATCACTGTATCTAACTCTCCTTTTTCG
CTCGTCCAACGCCGGCGGACCTCAAAAAGGATCTAAAAATAAGACAGTAGTGGACTTATATTCATACCATATGAT
GGGTGTTTGCTCACTCGTATGGATCAAAATTCCATGGTTTCTTCTGTACAACTTGTACACTTATTTGGACTTTTC
TAACGGTTTTTCTGGTGATTTGAGAAGTCCTTATTTTGGTGTTCGCAGCTTATCCGTGATTGAACCATCAGAAAT
ACTGCAGCTCGTTATCTAGTTTCAGAATGTGTTGTAGAATACAATCAATTCTGAGTCTAGTTTGGGTGGGTCTTG
GCGACGGGACCGTTATATGCATCTATGCAGTGTTAAGGTACATAGAATGAAAATGTAGGGGTTAATCGAAAGCAT
CGTTAATTTCAGTAGAACGTAGTTCTATTCCCTACCCAAATAATTTGCATAGAACTGCTTCGTATCCACATACGCA
GTGGACGTAGCAAATTTCACTTTGGACTGTGACCTCAAGTCGTTATCTTCTACTTGGACATTGATGGTCATTACG
TAATCCACAAAGAATTGGATAGCCTCTCGTTTTATCTAGTGCACAGCCTAATAGCACTTAAGTAAGAGCAATGGA
CAAATTTGCATAGACATTGAGCTAGATACGTAACTCAGATCTTGTTCACTCATGGTGTACTCGAAGTACTGCTGG
AACCGTTACCTCTTATCATTTCGCTACTGGCTCGTGAAACTACTGGATGAAAAAAAAAAAGAGCTGAAAGCGAGA
TCATCCCATTTTGTCATCATACAAATTCACGCTTGCAGTTTTGCTTCGTTAACAAGACAAGATGTCTTTATCCGG
TGTTTAAACCCCAGCGCCTGGCGGG BMT3 DELETION MS648 (SEQ ID NO: 54)
GACGGCACGGCCACGCGTTTAAACCGCCGCAGGGTCCCACACAGACCAAATCCAAGTTATTCCCTAAGGGATGGT
TTTCAGAGAGAAGAAACTATAATGGTAAACCGGTTGTTGCGGGATGACCCCTCTAAGAGTGATATGCACAATA
GACAGTCTGTTACGCCAAAAGAACTGTGGAAAGTGTTGGGAGACTACGATCTATGGCCTATATACGCATTGGCCA
TGGTATTTTCCATTCCCCAGATACCGATAAAGAGATACCTTACTCTTACTTTGAGGGCATTAGAGTTCACTACCA
CTGAGATCAATCTCTTAACAATCCCTGCTTCGTTTCTGGCGGGAATCATGTCAATTGCTATTTCATTAGTCAGTG
AGTTCTTCAATGAAGGTTTGATTATCGGTATATTGTGTCAATTCTGGTTGCTTATTATGGTTATCATTGAATACA
CCTCTGTGGAAAGATATCTCCCTGGGGACAATATGTGTTGCAACTGTTCGTTGTTGGTGCCCCAGTCCCCCAAC
CGGTACTAATCGGTCTATGTTCCCGTAACTCATATTCGGTTAGAACTAGAACAATAAGTGCATCATTGTCAACA
TTGTGGTTCAATTGTCGAACATTGCTGGTGCTTATATCTACAGGGAAGACGATAAGCCTTTGTACAAGAGAGGTA
ACAGACAGTTAATTGGTATTTCTTTGGGAGTCGTTGCCCTCTACGTTGTCTCCAAGACATACTACATTCTGAGAA
ACAGATGGAAGACTCAAAAATGGGAGAAGCTTAGTGAAGAAGAGAAAGTTGCCTACTTGGACAGAGCTGAGAAGG
AGAACCTGGGTTCTAAGAGGCTGGACTTTTTGTTCGAGAGTTAAACTGCATAATTTTTTCTAAGTAAATTTCATA
GTTATGAAATTTCTGCAGCTTAGTGTTTACTGCATCGTTTACTGCATCACCCTGTAAATAATGTGAGCTTTTTTC

```
CTTCCATTGCTTGGTATCTTCCTTGCTGCTGTTTCGCTCGTCCAACGCCGGCGGACCTGAGACGGAAAACGGAGA
AAGGAGAACGGAGAACGAAGAACGAAGGGAGAGAGAAGCAAAGGGAAGAGCAAGGTATTCTGGAGAGATTAAGAA
AATAGTAGAATAGATTTAACGAAACTGAAACTGAAAGACCGAAAAAGAATGCAGAAATTAAACACCATAGGGCA
GATTGATTCCGTAATCGGTTTCTTGCTACTATATCTTTCTAGGCTGTCTATAATCCTTTTATAATTTAATCTGCT
AATATCGCTGTCACGATTATTGACATCGACTGTATTTCAACACACAGGTCTTACAGATAGCATGGGGTTTCCAGT
ATTTGATTGACATTTCCGTTTTTGCATAGTCCATAATATAAGGATCAAAAACATGAGATGTCGCAAGGCCTCTTA
AACATGAAATCTCCGTTTACCTTCCGCCATACAACCTTACGCATACAGCAGCTCGGTTTCTACATAGAGTCTTTT
CAAGAACCGGGGTAAAAACCGTTTTACATAGAAAGAGGTAAAACGTTGTGATCATGTGACCGCTGAACATCTCCG
GAACCAACACTTCGCGATCTTTTTTCGTCTGTCACATACTCAAGGTAAACTAAGTTTCACAACACGAAGGCTCCG
TATCATAAATCCTCAGAGTTGAAGCACTGGCCCCCATCTAATAAATACTCCGAAATGAGTCAAATCCAGTCAAGC
CAAGTGGGGGCGAAAAATATGCAAACCGCACAGCCTCAGGCTCAACAAAGACCAATCAATGGGTCTGTGACCCTG
AGCAATGGCCAGAGGATAAACCCTCAGAACTTGACTCCGGTGTTTAAACCCCAGCGCCTGGCGGG

BMT4 DELETION MS649 (SEQ ID NO: 55)
GACGGCACGGCCACGCGTTTAAACCGCCCGTTCTGATGGCTTGATGACCGTTGTATTGCCTGTCACTATAGCCAG
GGGTAGGGTCCATAAAGGAATCATAGCAGGGAAATTAAAAGGGCATATTGATGCAATCACTCCCAATGGCTCTCT
TGCCATTGAAGTCTCCATATCAGCACTAACTTCCAAGAAGGACCCCTTCAAGTCTGACGTGATAGAGCACGCTTG
CTCTGCCACCTGTAGTCCTCTCAAAACGTCACCTTGTGCATCAGCAAAGACTTTACCTTGCTCCAATACTATGAC
GGAGGCAATTCTGTCAAAATTCTCTCTCAGCAATTCAACCAACTTGAAAGCAAATTGCTGTCTCTTGATGATGGA
GACTTTTTTCCAAGATTGAAATGCAATGTGGGACGACTCAATTGCTTCTTCCAGCTCCTCTTCGGTTGATTGAGG
AACTTTTGAAACCACAAAATTGGTCGTTGGGTCATGTACATCAAACCATTCTGTAGATTTAGATTCGACGAAAGC
GTTGTTGATGAAGGAAAAGGTTGGATACGGTTTGTCGGTCTCTTTGGTATGGCCGGTGGGTATGCAATTGCAGT
AGAAGATAATTGGACAGCCATTGTTGAAGGTAGAGAAAAGGTCAGGGAACTTGGGGGTTATTTATACCATTTTAC
CCCACAAATAACAACTGAAAAGTACCCATTCCATAGTGAGAGGTAACCGACGGAAAAAGACGGGCCCATGTTCTG
GGACCAATAGAACTGTGTAATCCATTGGGACTAATCAACAGACGATTGGCAATATAATGAAATAGTTCGTTGAAA
AGCCACGTCAGCTGTCTTTTCATTAACTTTGGTCGGACACAACATTTTCTACTGTTGTATCTGTCCTACTTTGCT
TATCATCTGCCACAGGGCAAGTGGATTTCCTTCTCGCGGCTGGGTGAAAACGGTTAACGTGAACGCTCGTCCA
ACGCCGGCGGACCTGCCTTGGGGGACTTCAAGTCTTTGCTAGAAACTAGATGAGGTCAGGCCCTCTTATGGTTGT
GTCCCAATTGGGCAATTTCACTCACCTAAAAAGCATGACAATTATTTAGCGAAATAGGTAGTATATTTTCCCTCA
TCTCCCAAGCAGTTTCGTTTTTGCATCCATATCTCTCAAATGAGCAGCTACGACTCATTAGAACCAGAGTCAAGT
AGGGGTGAGCTCAGTCATCAGCCTTCGTTTCTAAAACGATTGAGTTCTTTTGTTGCTACAGGAAGCGCCCTAGGG
AACTTTCGCACTTTGGAAATAGATTTTGATGACCAAGAGCGGGAGTTGATATTAGAGAGGCTGTCCAAAGTACAT
GGGATCAGGCCGGCCAAATTGATTGGTGTGACTAAACCATTGTGTACTTGGACACTCTATTACAAAAGCGAAGAT
GATTTGAAGTATTACAAGTCCCGAAGTGTTAGAGGATTCTATCGAGCCCAGAATGAAATCATCAACCGTTATCAG
CAGATTGATAAACTCTTGGAAAGCGGTATCCCATTTTCATTATTGAAGAACTACGATAATGAAGATGTGAGAGAC
GGCGACCCTCTGAACGTAGACGAAGAAACAAATCTTACTTTTGGGGTACAATAGAGAAAGTGAATCAAGGGAGGTA
TTTGTGGCCATAATACTCAACTCTATCATTAATGTGGTTCTTTTGGTAGCAAAAATCTTTGTTGTTTTGTTCAGT
TCCTCACTTCATTGATGGCTTCGTTAGTTGACTCCGTGATGGATTTCTTATCTACTTTGATCATATATGTTTCT
AACTCTTTTGCTGGGAAAAGAGACAAGAATGAGTATCCAGTTGGAAGGTCAAGGTTGGAGCCCTTAGGAGTTCTT
GTCTTTTCCGTAATCATAATTGTCTCGGTGTTTAAACCCCAGCGCCTGGCGGG

MNN4-1/PNO1 DELETION MS056 (SEQ ID NO: 56)
GACGGCACGGCCACGCGTTTAAACCGCCAAGGCATATAGGCGAGGGAGAGTTAGCTAGCATACAAGATAATGAAG
GATCAATAGCGGTAGTTAAAGTGCACAAGAAAAGAGCACCTGTTGAGGCTGATGATAAAGCTCCAATTACATTGC
CACAGAGAAACACAGTAACAGAAATAGGAGGGGATGCACCACGAGAAGAGCATTCAGTGAACAACTTTGCCAAAT
TCATAACCCCAAGCGCTAATAAGCCAATGTCAAAGTCGGCTACTAACATTAATAGTACAACAACTATCGATTTTC
AACCAGATGTTTGCAAGGACTACAAACAGACAGGTTACTGCGGATATGGTGCACTTGTAAGTTTTTGCACCTGA
GGGATGATTTCAAACAGGGATGGAAATTAGATAGGGAGTGGGAAAATGTCCAAAGAAGAAGCATAATACTCTCA
AAGGGGTTAAGGAGATCCAAATGTTTAATGAAGATGAGCTCAAAGATATCCCGTTTAAATGCATTATATGCAAAG
GAGATTACAAATCACCCGTGAAAACTTCTTGCAATCATTATTTTTGCGAACAATGTTTCCTGCAACGGTCAAGAA
GAAAACCAAATTGTATTATATGTGGCAGAGACATTTAGGAGTTGCTTTACCAGCAAAGAAGTTGTCCCAATTTC
TGGCTAAGATACATAATAATGAAAGTAATAAAGTTTAGTAATTGCATTGCGTTGACTATTGATTGCATTGATGTC
GTGTGATACTTTCACCGAAAAAAAAACACGAAGCGCAATAGGAGCGGTTGCATATTAGTCCCCAAAGCTATTTAAT
TGTGCCTGAAACTGTTTTTTAAGCTCATCAAGCATAATTGTATGCATTGCGACGTAACCAACGTTTAGGCGCAGT
TTAATCATAGCCCACTGCTAAGCCAGAATTCTAATATGTAACTACGTACCTTTCCTTTTAATAAATGATCTGTAT
TTTCCACCTAGTAGCAGATCAAATTGTTCAACTTTAAGTCTTTGGTCCCTCAAGCTGAGAGAACTTGCGCGCTCGT
CCAACGCCGGCGGACCTCGGAGGAATGCAAATAATAATCTCCTTAATTACCCACTGATAAGCTCAAGAGACGCGG
TTTGAAAACGATATAATGAATCATTTGGATTTATAATAAACCCTGACAGTTTTTCCACTGTATTGTTTAACAC
TCATTGGAAGCTGTATTGATTCTAAGAAGCTAGAAATCAATACGGCGTAACATGGATGACATTGAATAAGCACC
GGCTTTTTTGATTAGCATATACCTTAAAGCATGCATTCATGCGTACATAGTTGTTAAAGGGCTTCTTCCATTATC
AGTATAATGAATTACATAATCATGCACTTATATTTGCCCATCTCTGTTCTCTCACTCTTGCCTGGGTATATTCTA
TGAAATTGCGTATAGCGTGTCTCCAGTTGAACCCCAAGCTTGGCGAGTTTGAAGAGAATGCTAACCTTGCGTATT
CCTTGCTTCAGGAAACATTCAAGGAGAAACAGGTCAAGAAGCCAAACATTTTGATCCTTCCCGAGTTAGCATTGA
CTGGCTACAATTTTCAAAGCCAGCAGCGGATAGAGCCTTTTTTGGAGGAAACAACCAAGGGAGCTAGTACCCAAT
GGGCTCAAAAAGTATCCAAGACGTGGGATTGCTTTACTTTAATAGGATACCCAGAAAAAAGTTTAGAGAGCCCTC
CCCCGTATTTACAACAGTGCGGTACTTGTATCGCCTCAGGGAAAAGTAATGAACAACTACAGAAAGTCCTTCTTGT
ATGAAGCTGATGAACATTGGGGATGTTCGGAATCTTCTGATGGGTTTCAAACAGTAGATTTATTAATTGAAGGAA
AGACTGTAAAGACATCATTTGGAATTTGCATGGATTTGAATCCTTATAAATTTGAAGCTCCGGTGTTTAAACCCC
AGCGCCTGGCGGG

MNN4-2 DELETION MS652 (SEQ ID NO: 57)
GACGGCACGGCCACGCGTTTAAACCGCCCTGTGGACTCAGGACCAGCTCAGCTTGACAAACCAAGACTTGCACTC
CAATGTGCACAACCCAGTGATTGAGCAGATCGAAACCTCACAAGGATCAGATTGTAGTATGGAAAACTTTGTAT
TCTCTATGTACTTAAACACTGGTTTATTTTTTTATTGATCGTTATATTGAACAGTTTACACTGGAACATCTTCAG
GGTCGATGTCCTTAATCCAGTGTTGACCAAAGATTGGGATCTTCTCGAAGAAAGTCTTTTGGAACAAAGGCCAGT
TTTCAGTGAAAGTGAAGACGGCAAACAGACCGGCACCTCCCCAGAAAGCCAAAATTGGAAAGTAGTTTAATTT
GGGTTGGAGTCAATCCAGCAATTTTCTTGACGGTGGTATACTTGGGACCTTTAACGTACTGAAATGTTAGAACAT
GTTTGTAAAAATCAAATCATCACTGCAGAAACGGTTTGTGTGCCTGCACCGGAGGGTTATCATAATGCCACTTAC
GTTGACCATTTTGGAGGTGTTTGACTAAGTTCAAATATGAATCTCTAAGAAAACTAATAATCAATATGGTGCGAG
```

-continued

CATTGATTGGTTGGACAGCTAGTTTGGAGAAGTACACGACTTAGATGAATCTGCAATAAGGAATAGTCCAATCTG
ATTATGTAAGCTCTCCTTTTTGGTTTTCATTTCCATCAGCTCAAGCTTATCATAGCTCAGGTCCCCTCCAGCTTA
TGATGGAATAGGCCATTATTTTTTGCCCTAAAAAGTGGAAGTCCACAAGAAGAAATACAAATACTCAAAATTCAA
AAGTCTTCCTTTGAGTGGATGCAATTTTACGTAGTTTACTGTATGACGTAACTAATGAACCCTTCCGACACAAAG
ATTGAGGTGCCTCACTTAACGTCATTCTTCTATACCCACGAGTGCAACTGACTAGGTCTTATTTTGTTAATTGCC
TCAGTTTCTCCGAACGCTCGTCCAACGCCGGCGGACCTTTATGCATATACTGAAACAACAGAAGGAACTACAGTA
AATTCATAAAAAGCTTAATTCTTACTTTCATCTCGGCACTGTAAATTAACTCAAGTTGGGGCAACATTGTGTGTA
TACTCTTACTGGCATCTTTTCATCTGAAGTCATCTTCTACTACTCTTCTCTTCTGTATGACGTAATCAGCTCGGC
AGCTGTGGCATCGAACAAAAAAATGAACAGCCATCCGTCATATCTCATGACTGACTGAGCAAGAACTAAGTCAAC
AGGAAACCTAAAATAAGCTTTCCATTTCTTTTGCGCTGAAGCCAACCACTCCCCACACAGTTGATGAGTGGACGC
AAAACCAGCTCCTATACCTTGACAGAAGAGTCGCCGGAATCAACCTCAACAATTCAGGATATACGAGAGGAAGAC
CAAGTTGCTCCAGGGCCCCAGCAAGAAGCACCTAAACAGTCACATATCCAAAAATGGTTAAGCGATCATCCTAAA
GTATACGCAGTTTTATCTTGGATATGGAAATTTTGGTTGAAACAGTGGTTTCTCATATGTTTGGGCCCTGCGGTT
GCTCTAGCTCATGCATACCCAAATTTTGCCAGACATGATGGAACCATTAGGTCAGAGTATACTATCAACTACGGA
GCCGTAGCTATCATATTCTTCATCTCTGGTCTTACTATGAAAACAAAGACTTTTTGAAGAACTTTGGACACTGG
AGAGCCCATTTCACAGTGTTAAGCTGCTCGTTTCTACTTACTTCTTCTATCATTTACGGTATAGCGTGCGGTATA
AGAGCTGCTCATGATTCCAATATCGATGACTGGATGTTAGCAGGACTTATTGTTACCGCATGTTGTCCAACCACT
GTGAGCGGTGTTTAAACCCCAGCGCCTGGCGGG

MNN4-3 DELETION MS653 (SEQ ID NO: 58)
GACGGCACGGCCACGCGTTTAAACCGCCGGAGGAGGTGGAACCACCTGTGCAGGCGGTCTGAAAGTGTTCAAGTA
CGGATCTACTACCAAATATACATCTGGTAACCTGAACGGCGTCAGGTTAGTATACTGGAACGAAGGAAAGTTGCA
AAGCTCCAAATTTGTGGTTCGATCCTCTAATTACTCTCAAAAGCTTGGAGGAAACAGCAACGCCGAATCAATTGA
CAACAATGGTGTGGGTTTTGCCTCAGCTGGAGACTCAGGCGCATGGATTCTTTCCAAGCTACAAGATGTTAGGGA
GTACCAGTCATTCACTGAAAAGCTAGGTGAAGCTACGATGAGCATTTTCGATTTCCACGGTCTTAAACAGGAGAC
TTCTACTACAGGGCTTGGGGTAGTTGGTATGATTCATTCTTACGGTGAGTTCAAACAGTTTGGTTTGTTCAC
TCCAATGACATCTATTCTACAAAGACTTCAACGAGTGACCAATGTAGAATGGTGTGTAGCGGGTTGCGAAGATGG
GGATGTGGACACTGAAGGAGAACACGAATTGAGTGATTTGGAACAACTGCATATGCATAGTGATTCCGACTAGTC
AGGCAAGAGAGAGCCCTCAAATTTACCTCTCTGCCCCTCCTCACTCCTTTTGGTACGCATAATTGCAGTATAAAG
AACTTGCTGCCAGCCAGTAATCTTATTTCATACGCAGTTCTATATAGCACATAATCTTGCTTGTATGTATGAAAT
TTACCGCGTTTTAGTTGAAATTGTTTATGTTGTGCCTTGCATGAAATCTCTCGTTAGCCCTATCCTTACATTT
AACTGGTCTCAAAACCTCTACCAATTCCATTGCTGTACAACAATATGAGGCGGCATTACTGTAGGGTTGGAAAAA
AATTGTCATTCCAGCTAGAGATCACACGACTTCATCACGCTTATTGCTCCTCATTGCTAAATCATTTACTCTTGA
CTTCGACCCAGAAAAGTTCGCCCGCTCGTCCAACGCCGGCGGACCCTATAGTTGTTTTTCTATATAAAACGAAAC
GTTATCATCTTTAATAATCATTGAGGTTTACCCTTATAGTTCCGTATTTTCGTTTCCAAACTTAGTAATCTTTTG
GAAATATCATCAAAGCTGGTGCCAATCTTCTTGTTTGAAGTTTCAAACTGCTCCACCAAGCTACTTAGAGACTGT
TCTAGGTCTGAAGCAACTTCGAACACAGAGACAGCTGCCGCCGATTGTTCTTTTTTGTGTTTTTCTTCTGGAAGA
GGGGCATCATCTTGTATGTCCAATGCCCGTATCCTTTCTGAGTTGTCCGACACATTGTCCTTCGAAGAGTTTCCT
GACATTGGGCTTCTTCTATCCGTGTATTAATTTTGGGTTAAGTTCCTCGTTTGCATAGCAGTGGATACCTCGATT
TTTTTGGCTCCTATTTACCTGACATAATATTCTACTATAATCCAACTTGGACGCGTCATCTATGATAACTAGGCT
CTCCTTTGTTCAAAGGGGACGTCTTCATAATCCACTGGCACGAAGTAAGTCTGCAACGAGGCGGCTTTTGCAACA
GAACGATAGTGTCGTTTCGTACTTGGACTATGCTAAACAAAAGGATCTGTCAAACATTTCAACCGTGTTTCAAGG
CACTCTTTACGAATTATCGACCAAGACCTTCCTAGACGAACATTTCAACATATCCAGGCTACTGCTTCAAGGTGG
TGCAAATGATAAAGGTATAGATATTAGATGTGTTTGGGACCTAAAACAGTTCTTGCCTGAAGATTCCCTTGAGCA
ACAGGCTTCAATAGCCAAGTTAGAGAAGCAGTACCAAATCGGTAACAAAAGGGGGAAGCATATAAAACCTTTACT
ATTGCGACAAAATCCATCCTTGAAAGTAAAGCTGTTTGCGGTGTTTAAACCCCAGCGCCTGGCGGG

PRB1 DELETION MS655 (SEQ ID NO: 59)
GACGGCACGGCCACGCGTTTAAACCGCCTGTTCAATTGAACTGGTGTTTGAACAACGCCTACATCAATAATACCA
ATCATCGGACGAAAAATATGGAATTAATACTAAAATATCTTATCCCCTCCAGTCTTATAGTTGGTAAGATACCAA
ATTTGAACATCCTGAACCAGCTGCTGTCATCTCAAGAGGCACACCCTCTGATTGAGCTTTATCGACCACTGATTT
CAACCCTCAAAAAGGGTAATGTTTTCGAATTCCACAAATACCTGTTTGATAATGAGTCATACTTTTTAAAGATGA
ACGTTCTCCTGCCGCTACTTCAACGGTTGCGTATTTTGCTGTTCAGAAATCTGGTCCGAAAGCTGGCCCTTATAG
AGCCACCAGTCAACAACTCTCTGAGATTTTCATCCATCAAAACAGCCCTTTTCGTTTCCATTTCACCCAATCAAA
ACGCATACTTTCAGAACAATTATTCATACCTGATTGTTACCAACGAGTCCCAGATAGACGACTCCTTTGTGGAGA
ACCTCATGATCAGTCTAATCGATCAAAACCTAATTAAGGGTAAACTCGTCAACGATAACCACCGAATAATTGTCT
CCAAGGCCGATACATTCCCGGAGATCCCTACGATTATTCGACTAAGTTTGCCGTAGACTCGTCATTCGATTGGC
TGGACCAATAGACGTCCTTTTTTTTTTTTATCGTGTCTGCCGTTTAATGTCACGCCTCATGTTTCAAGTTACG
ATAACTTATCATGCAGATACTAAATAGTCACATGACGAATGACGATTTTTTGCGGGTTGCTCAGAGGAATATGCC
TCTGATAAGCGAGGTAAATGTCGAGCATAAGCCACTTACTGTATAAATACCCCTTTATCGCCACTTTATCTTTTC
TCCTTGTCCGTTATCTACAACACCCCAGTAAAACATTACAAACACTCTAGTGTTGTTTTACTGTCCCTTTTAACT
CTCTTCAAACAAATCTCCATATTATTTAAACTCGCTCGTCCAACGCCGGCGGACCTATTGGAGAAAAGGAATACA
CAAGGAGTTAAAAAAAGTGTGGTAGAAAGTGCATTTGTCATAATTTTCCATATGTTCCTGTCACTGTAATCTTTT
ATATTTTGTTTTGTTTTATGTAGTATTTCAAAAGGTTCTTATCATCTTACTGGCATAAACTTGATGTACGCAGAG
ATAGCAACCGTTGCTTAGGTAAGCATAGTAAAAATGGCTGGTTTTCTGTCTTATTTAAGGCCACTGTTGGGACA
AAACACAATAACTAGATTTTATCGGATTGAACAGTGTAAAGGCTTCACTGGCTTATATCTTGTATGAGTACGATA
CATTATCCAGTTCCATCAAGGCCTGTGGAAATATTACAGCCAGGACATGAACCTGAAAGGGAGTTTAGTGGGATC
ACTGTAGATAAATAGGAACAGACTTAATGAAGAAAGTATTATCAGACGAAAATAGACGAAGCGTTGAAAAGGGGC
ACAGAAAGACGTTACGTTGATGATCATAGCAGAGGTCATGAGTCTCCAAGTTCAGATTTGGAGGACACTCCGGAT
CAATTCTTGGAATTTCACATTCATGATAACGGAGATAGGAAGATTTCAAGGCCAGACACTGCTTCGTCATTGATT
AGTGAAAACGACATGGACTACGATGATTTGTTTGTTGACAGAAAGCAACCAAAACATGCTACTTCTCATGTAAAG
CAGTTTATTAGGAAGAATGTGTTCAAAAGAAGACTCATCTACCAAACATTGGGGCTAGAGAACTGGAATTACAG
AAACGGCTTGCTTTATTAGAGGGCCCAATAGATGACGATGAGATTATTAGTGCTATGCCCATGGTAGCGTGTCCC
TCTGACTATAACGATCAACCTGCTGATTCAAATTCAACGGTGTTTAAACCCCAGCGCCTGGCGGG

AOX1 DELETION MS530 (SEQ ID NO: 60)
GACGGCACGGCCACGCGTTTAAACCGCCAGATCTAACATCCAAAGACGAAAGGTTGAATGAAACCTTTTTGCCAT
CCGACATCCACAGGTCCATTCTCACACATAAGTGCCAAACGCAACAGGAGGGGATACACTAGCAGCAGACCGTTG
CAAACGCAGGACCTCCACTCCTCTTTCTCCTCAACACCCACTTTTGCCATCGAAAACCAGCCCAGTTATTGGGCT

-continued

```
TGATTGGAGCTCGCTCATTCCAATTCCTTCTATTAGGCTACTAACACCATGACTTTATTAGCCTGTCTATCCTGG
CCCCCCTGGCGAGGTTCATGTTTGTTTATTTCCGAATGCAACAAGCTCCGCATTACACCCGAACATCACTCCAGA
TGAGGGCTTTCTGAGTGTGGGGTCAAATAGTTTCATGTTCCCCAAATGGCCCAAAACTGACAGTCTCAACGCTGT
CTTGGAACCTAATATGACAAAAGCGTGATCTCATCCAAGATGAACTAAGTTTGGTTCGTTGAAATGCTAACGGCC
AGTTGGTCAAAAAGAAACTTCCAAAAGTCGGCATACCGTTTGCTGTTTGGTATTGATTGACGAATGCTCAAAA
ATAATCTCATTAATGCTTAGCGCAGTCTCTCTATCGCTTCTGAACCCCGGTGCACCTGTGCCGAAACGCAAATGG
GGAAACACCCGCTTTTTGGATGATTATGCATTGTCTCCACATTGTATGCTTCCAAGATTCTGGTGGGAATACTGC
TGATAGCCTAACGTTCATGATCAAAATTTAACTGTTCTAACCCCTACTTGACAGCAATATATAAACAGAAGGAAG
CTGCCCTGTCTTAAACCTTTTTTTATCATCATTATTAGCTTACTTTCATAATTGCGACTGGTTCCAATTGACAA
GCTTTTGATTTTAACGACTTTTAACGACAACTTGAGAAGATCAAAAAACAACTAATTATTCGAAACGCGCTCGTC
CAACGCCGGCGGACCTTCAAGAGGATGTCAGAATGCCATTTGCCTGAGAGATGCAGGCTTCATTTTTGATACTTT
TTTATTTGTAACCTATATAGTATAGGATTTTTTTTGTCATTTTGTTTCTTCTCGTACGAGCTTGCTCCTGATCAG
CCTATCTCGCAGCTGATGAATATCTTGTGGTAGGGGTTTGGGAAAATCATTCGAGTTTGATGTTTTTCTTGGTAT
TTCCCACTCCTCTTCAGAGTACAGAAGATTAAGTGAGACGTTCGTTTGTGCAAGCTTCAACGATGCCAAAAGGGT
ATAATAAGCGTCATTTGCAGCATTGTGAAGAAAACTATGTGGCAAGCCAAGCCTGCGAAGATGTATTTTAAGTT
TGACTTTGATGTATTCACTTGATTAAGCCATAATTCTCGAGTATCTATGATTGGAAGTATGGGAATGGTGATACC
CGCATTCTTCAGTGTCTTGAGGTCTCCTATCAGATTATGCCCAACTAAAGCAACCGGAGGAGGAGATTTCATGGT
AAATTTCTCTGACTTTTGGTCATCAGTAGACTCGAACTGTGAGACTATCTCGGTTATGACAGCAGAAATGTCCTT
CTTGGAGACAGTAAATGAAGTCCCACCAATAAAGAAATCCTTGTTATCAGGAACAAACTTCTTGTTTCGAACTTT
TTCGGTGCCTTGAACTATAAAATGTAGAGTGGATATGTCGGGTAGGAATGGAGCGGGCAAATGCTTACCTTCTGG
ACCTTCAAGAGGTATGTAGGGTTTGTAGATACTGATGCCAACTTCAGTGACAACGTTGCTATTTCGTTCAAACCA
TTCCGAATCCAGAGAAATCAAAGTTGTTTGTCTACTATTGATCCAACGCAGTGCGGTCTTGAAACTGACAATAGT
GTGCTCGTGTTTTGAGGTCATCTTTGTATGAATAAATCTAGTCTTTGATCTAAATAATCTTGACGAGCCAGACGA
TAATACCAATCTAAACTCTTTAAACGCGGTGTTTAAACCCCAGCGCCTGGCGGG

DNL4 DELETION MS743 (SEQ ID NO: 61)
GACGGCACGGCCACGCGTTTAAACCGCCCTCCACCGTCTTGATACTTTCTGAGGTGCACAGACCAGAGGATTGTG
CGAACCCTAAATAGTTGTATGAACTCAAATTCAAGCGCTCTGTGACGGTGCCGGAATAATTATAGGTATTGTTGT
AATCGTCACTGGTTCTGTCGTAACATTTGATGTACCTACCGGGAACTCCACATATGGGCCTTGCAAAACAGTCAT
CTAATCTTGTTTTCAAACGACGCGTGTAGAAACTTTCAAAATTGGCATACCATGGAGCAATACCATCTTTCACCA
TCACATCTCTGAATAGTTCAGGGTGAAACAACTTCCCAAAGAAGTCTCTAATATGGCCTATTATGATCAAAATAA
GGTAATTAAGGTATGTTGCAATCAGGATGAAATATGGAGGTTCGTCCTCGATGGGAACTGGAAGCGGCTCGCCAG
GGTTATGCTTAGAGACAAAGAGCCATTCTTTACTGGTCAAGGACCCAAATTCTTTCTCGGCCTTCTCTTGTGGTG
AATCATTGTCTATGAGAGCATCTGGGATAGTTTTTGACATGATCTTTTTCGACACGGCTATATAGCAAAAAGCAA
AAAAAAAAGACCGAATGGAATTATATGGTCTAAAAAAACAAACTGGTGGTAAAATAAAAAAAAAAACGACTGGTGGG
CGGTTTCAAAGGAGACTAATGATCTTCTATGCCCGCGGAAATAAATAGTACTCCAACGACTGAACTCAGCGGTAT
TAAAGTTTGTGAATAAAATTACAAGGCTTAGAAAGCTTGGTTGGTCTTTCGGTATCTGTAGATGGTAGAGTTTTG
AGAACATTTCATTTCCACAGTAACCAACGAACACGACCCGTGACTTCCGGGGGTTGGCAGATGTTAACGCGCGCG
TGGTAGAAGTTTATCTTGGGAGGTGCTAGAGGGTGCTCTTGGCCTTGTTCGTCGGGGGGAAGTGTTTGTAGTTAA
CGTACAACTCCTCATGACTGGGGATCAGAATTTCAACTTGATTTGCCGCTAATCGCTCGTCAACGCCGGCGGAC
CTTAAAAATAATGATTTACATTTAAGAAGTAACAGCACATATATACTGTAAGATTAACTTTGCGTACCCTAAATT
TTACTAATAAACTTAACGGGTTGCCATAGCCTTGGTAACCACACGTTTCAATGCCAATTCAGCTTTTCTGAAGTC
ATCACCGGAAGCATCTTCTAGCTCCAAAGCAGCCAAAGCGTCAGACAAAGCAGACTCGATCTTGTCCTTAGCACT
TCTCTTTAGCTTGGAAGACAAAATTGGGTCAGTGATGGTAGACTCAATGGAGGAAACGTAAGCCTCCAACTTCTG
TTTGGATTCGTGACGGTTAGCGAAGTCCTCGTCAGCCTTCTTGAACTTGTCAGCATCGTTGATCATCTTTTCGAT
CTCGGAAGAAGACAATCTACCAATAGAGTTAGAAATAGTGATGTTGGCAGATCTTCCGGTAGACTTCTCGACAGC
GGTAACCTTCAAGATACCGTTGGCATCAATCTCAAAGATAGCCTCCAACACTGGCTCACCAGCAGATAGGAGG
AATGTTCTTCAAGTCGAACTCACCCAACAAGGTGTTCTCAGAACAGTTGACACGCTCACCCTGGTAAACTGGGAA
TTGAACAGTGGTTTGGTGGTCGTCAACAGTGGTGAAAGTTCTTCTCTTGATAGTTGGGACAGTGGTGTTTCTTGG
AACAACTGGGGCAAAGACGTTACCTTGCATGGCAACACCCAAAGAAAGAGGGATAACATCCAACAACAACAAGTC
CTTGGTCTCTTCAGAGGTAGATTGACCGGTCAAAATAGCACCTTGAACGGCGACCACCGTAAGCGACAGCCTCATC
AGGGTTGATGGATTCTCCAATTGCTTACCATCGAAGAAGTCAGACAACAGCTTTTGGACCTTTGGAATTCTGGT
GGAACCACCAACCAAGACGACGTCATCGACCTTGGATTTCTCGATCTTTGAGTCCTTCAAAACTTGTTCAACAGG
CTCCAAAGTAGACTTGAACAAATCAGCGTTGCGGTGTTTAAACCCCAGCGCCTGGCGGG

PEP4 DELETION MS654 (SEQ ID NO: 62)
GACGGCACGGCCACGCGTTTAAACCGCCCGTATCTAATCTTTCTCGCTCCCCGTACGTTAAGAATGAAATTTCTA
CTTCCATTATAGAAAATAGTGTATCACTGCCAGCATCTTTTACTCACAAGCAATTAAACAAAGTAACAATGGTCT
CTAAGCAATTGGAATCACCACAGGGGACCTTTATCACGTTGAATCTAGTTGAAAATTCAGTGTCCAAGTTCGGTG
CAGTACACATACCACAAGGGAAAAACCCCATTTGTTGTTGGTAGAGATTCATCTTGTGACTGGTTGATCAAAGAAG
AAAGAATTTCCAAAATACACTGCATGATTGCCAAAAAAGGCATCCTACTGCTAATCCTTCCATATTTGAGTCAC
CTGCTTTAGGGCTGGAAGATATTTGGTTACTAGATTTTAGTACAAACTCTTGCTTTGTCAATGACATTAAAATAG
GCAAGAATCGCAAAACTCAAATATTTCATGAGATGAGATATGCTTGTTCAAAGATGCCCAGAAAAAAGAGCAAC
TCGTTTATAGGGTTCATATTGATGATGGAACAGGCCTTTTCCAGGGAGGTGAAAGAACCCAAGCCAATTCTGATG
ACATTCTGGATATTGATGAGGTTGATGAAAAGTTAAGAGAACTATTGACAAGAGCCTCAAGGAAACGGCATATCA
CCCCTGCATTGGAAACTCCTGATAAACGTGTAAAAAGAGCTTATTTGAACAGTATTACTGATAACTCTTGATGGA
CCTTAAAGATGTATAATAGTAGACAGAATTCATAATGGTGAGATTAGGTAATCGTCCGGAATAGGAATAGTGGTT
TGGGGCGATTAATCGCACCTGCCTTATATGGTAAGTACCTTGACCGATAAGGTGGCAACTATTTAGAACAAAGCA
AGCCACCTTTCTTTATCTGTAACTCTGTCGAAGCAAGCATCTTTACTAGAGAACATCTAAACCATTTTACATTCT
AGAGTTCCATTTCTCAATTACTGATAATCAATTTAAAGCGCTCGTCAACGCCGGCGGACCTGCAAGAATAAAAG
TTGCTCAGCTGAACTTATTTGGTTACTTATCAGGTAGTGAAGATGTAGAGAATATATGTTTAGGTATTTTTTTTT
AGTTTTTCTCCTATAACTCATCTTCAGTACGTGATTGCTTGTCAGCTACCTTGACAGGGGCGCATAAGTGATATC
GTGTACTGCTCAATCAAGATTTGCCTGCTCCATTGATAAGGGTATAAGAACACCACCTGCTCCTCTTTAAAATTC
TCTCTTAACTGTTGTGAAAATCATCTTCGAAGCAAATTCGAGTTTAAATCTATGCGGTTGGTAACTAAAGGTATG
TCATGGTGGTATATAGTTTTTCATTTTACCTTTTACTAATCAGTTTTACAGAAGAGGAACGTCTTTCTCAAGATC
GAAATAGGACTAAATACTGGAGACGATGGGGTCCTTATTGGGTGAAAGGCAGTGGGCTACAGTAAGGGAAGACT
ATTCCGATGATGGAGATGCTTGGTCTGCTTTTCCTTTTGAGCAATCTCATTTGAGAACTTATCGCTGGGAGAGG
ATGGACTAGCTGGAGTCTCAGACAATCATCAACTAATTTGTTTCTCAATGGCACTGTGGAATGAGAATGATGATA
TTTTGAAGGAGCGATTATTTGGGGTCACTGGAGAGGCTGCAAATCATGGAGAGGATGTTAAGGAGCTTTATTATT
```

ATCTTGATAATACACCTTCTCACTCTTATATGAAATACCTTTACAAATATCCACAATCGAAATTTCCTTACGAAG
AATTGATTTCAGAGAACCGTAAACGTTCCAGATTAGAAAGAGAGTACGAGATTACTGACTCTGAAGTACTGAAGG
ATAACAGATATTTTGATGTGATCTTTGAAATGGCCGGTGTTTAAACCCCAGCGCCTGCGGG

PEP4 DELETION WITH HERCEPTIN INTEGRATION MS841 (SEQ ID NO: 63)
GACGGCACGGCCACGCGTTTAAACCGCCCGTATCTAATCTTTCTCGCTCCCCGTACGTTAAGAATGAAATTTCTA
CTTCCATTATAGAAAATAGTGTATCACTGCCAGCATCTTTTACTCACAAGCAATTAAACAAAGTAACAATGGTCT
CTAAGCAATTGGAATCACCACAGGGGACCTTTATCACGTTGAATCTAGTTGAAAATTCAGTGTCCAAGTTCGGTG
CAGTACACATACCACAAGGAAAAACCCCATTTGTTGTTGGTAGAGATTCATCTTGTGACTGGTTGATCAAAGAAG
AAAGAATTTCCAAAATACACTGCATGATTGCCAAAAAAAGGCATCCTACTGCTAATCCTTCCATATTTGAGTCAC
CTGCTTTAGGGCTGGAAGATATTTGGTTACTAGATTTTAGTACAAACTCTTGCTTTGTCAATGACATTAAAATAG
GCAAGAATCGCAAAACTCAAATATTTCATGGAGATGAGATATGCTTGTTCAAAGATGCCCAGAAAAAGAGCAAC
TCGTTTATAGGGTTCATATTGATGATGGAACAGGCCTTTTCCAGGGAGGTGAAAGAACCCAAGCCAATTCTGATG
ACATTCTGGATATTGATGAGGTTGATGAAAAGTTAAGAGAACTATTGACAAGAGCCTCAAGGAAACGGCATATCA
CCCCTGCATTGGAAACTCCTGATAAACGTGTAAAAGAGCTTATTTGAACAGTATTACTGATAACTCTTGATGGA
CCTTAAAGATGTATAATAGTAGACAGAATTCATAATGGTGAGATTAGGTAATCGTCCGGAATAGGAATAGTGGTT
TGGGGCGATTAATCGCACCTGCCTTATATGGTAAGTACCTTGACCGATAAGGTGGCAACTATTTAGAACAAAGCA
AGCCACCTTTCTTTATCTGTAACTCTGTCGAAGCAAGCATCTTTACTAGAGAACATCTAAACCATTTTACATTCT
AGAGTTCCATTTCTCAATTACTGATAATCAATTTAAAGCGCTCGTCAACGCCGGCGGACCTAACAGGAGGGGAT
ACACTAGCAGCAGACCGTTGCAAACGCAGGACCTCCACTCCTCTTCCTCAACACCCACTTTTGCCATCGAAAA
ACCAGCCCAGTTATTGGGCTTGATTGGAGCTCGCTCATTCCAATTCCTTCTATTAGGCTACTAACACCATGACTT
TATTAGCCTGTCTATCCTGGCCCCCCTGGCGAGGTTCATGTTTGTTTATTTCCGAATGCAACAAGCTCCGCATTA
CACCCGAACATCACTCCAGATGAGGGCTTTCTGAGTGTGGGGTCAAATAGTTTCATGTTCCCCAAATGGCCCAAA
ACTGACAGTTTAAACGCTGTCTTGGAACCTAATATGACAAAAGCGTGATCTCATCCAAGATGAACTAAGTTTGGT
TCGTTGAAATGCTAACGGCCAGTTGGTCAAAAAGAAACTTCCAAAAGTCGGCATACCGTTTGTCTTGTTTGGTAT
TGATTGACGAATGCTCAAAAATAATCTCATTAATGCTTAGCGCAGTCTCTCTATCGCTTCTGAACCCCGGTGCAC
CTGTGCCGAAACGCAAATGGGGAAACACCCGCTTTTTGGATGATTATGCATTGTCTCCACATTGTATGCTTCCAA
GATTCTGGTGGGAATACTGCTGATAGCCTAACGTTCATGATCAAAATTTAACTGTTCTAACCCCTACTTGACAGC
AATATATAAACAGAAGGAAGCTGCCCTGTCTTAAACCTTTTTTTTATCATCATTATTAGCTTACTTTCATAATTG
CGACTGGTTCCAATTGACAAGCTTTTGATTTTAACGACTTTTAACGACAACTTGAAGAATCAAAAACAACTAA
TTATTCGAAACGATGAGATTCCCATCCATCTTCACTGCTGTTTTGTTCGCTGCTTCTTCTGCTTTGGCTGAGGTT
CAGTTGGTTGAATCGGAGGAGGATTGGTTCAACCTGGTGGTTCTTTGAGATTGTCCTGTGCTGCTTCCGGTTTC
AACATCAAGGACACTTACATCCACTGGGTTAGACAAGCTCCAGGAAAGGGATTGGAGTGGGTTGCTAGAATCTAC
CCAACTAACGGTTACACAAGATACGCTGACTCCGTTAAGGGAAGATTCACTATCTCTGCTGACACTTCCAAGAAC
ACTGCTTACTTGCAGATGAACTCCTTGAGAGCTGAGGATACTGCTGTTTACTACTGTTCCAGATGGGGTGGTGAT
GGTTTCTACGCTATGGACTACTGGGGTCAAGGAACTTTGGTTACTGTTTCCTCCGCTTCTACTAAGGGACCATCT
GTTTTTCCCATTGGCTCCATCTTCTAAGTCTACTTCCGGTGGTACTGCTGCTTTGGGATGTTTGGTTAAAGACTAC
TTCCCAGAGCCAGTTACTGTTTCTTGGAACTCCGGTGCTTTGACTTCTGGTGTTCACACTTTCCCAGCTGTTTTG
CAATCTTCCGGTTTGTACTCTTTGTCCTCCGTTGTTACTGTTCCATCCTCTCTTCCTTGGGTACTCAGACTTACATC
TGTAACGTTAACCACAAGCCATCCAACACTAAGGTTGACAAGAAGGTTGAGCCAAAGTCCTGTGACAAGACTCAT
ACTTGTCCACCATGTCCAGCTCCAGAATTGTTGGGTGGTCCTTCCGTTTTTTGTTCCCACCAAAGCCAAAGGAC
ACTTTGATGATCTCCAGAACTCCAGAGGTTACATGTGTTGTTGTTGACGTTTCTCACGAGGACCCAGAGGTTAAG
TTCAACTGGTACGTTGACGGTGTTGAAGTTCACAACGCTAAGACTAAGCCAAGAGAGGAGCAGTACAACTCCACT
TACAGAGTTGTTTCCGTTTTGACTGTTTTGCACCAGGATTGGTTGAACGGAAAGGAGTACAAGTGTAAGGTTTCC
AACAAGGCTTTGCCAGCTCCAATCGAAAAGACTATCTCCAAGGCTAAGGGTCAACCAAGAGAGCCACAGGTTTAC
ACTTTGCCACCATCCAGAGATGAGTTGACTAAGAACCAGGTTTCCTTGACTTGTTTGGTTAAGGGATTCTACCCA
TCCGACATTGCTGTTGAATGGGAGTCTAACGGTCAACCAGAGAACAACTACAAGACTACTCCACCTGTTTTGGAC
TCTGACGGTTCCTTTTTCTTGTACTCCAAGTTGACTGTTGACAAGTCCAGATGGCAACAGGGTAACGTTTTCTCC
TGTTCCGTTATGCATGAGGCTTTGCACAACCACTACACTCAAAAGTCCTTGTCTTTGTCCCCTGGTAAGTAGACG
CACGCACACTCCCGACAGACAACTAGCTTGATAACAGGCCCCTTTTCCTTTGTCGATATCATGTAATTAGTTATG
TCACGCTTACATTCACGCCCTCCCCCCACATCCGCTCTAACCGAAAAGGAAGGAGTTAGACAACCTGAAGTCTAG
GTCCCTATTTATTTTTTTATAGTTATGTTAGTATTAAGAACGTTATTTATATTTCAAATTTTTCTTTTTTTCTG
TACAAACGCGTGTACGCATGTAACATTATACTGAAAACTGCTTGCCGGCCGTAAGATTATTACTTGCTATAAGTGCGTGCCTGAT
GAACAGGATATTGCGGTCAATAATGCTGATGGTTCATTAGACTTCAGCAAAGCCGATGCCAAAATAAGCCAATAC
GATCTCAACGCTATTGAAGCGGCTTGCCAGCTAAAGCAACAGGCAGCGAGGCGCAGGTGACAGCCTTAAGTGTG
GGCGGTAAAGCCCTGACCAACGCCAAAGGGCGTAAAGATGTGCTATCGCGCGGCCCGGATGAACTGATTGTGGTG
ATTGATGACCAGTTCGAGCAGGCACTGCCGCAACAAACGGCGAGCGCACTGGCTGCAGCCGCCCAGAAAGCAGGC
TTTGATCTGATCCTCTGTGGCGATGGTTCTTCCGACCTTTATGCCCAGCAGGTTGGTCTGCTGGTGGGCGAAATC
CTCAATATTCCGGCAGTTAACGGCGTCAGCAAAATTATCTCCGACGGATACCTCACCGTTGAGCGCGAA
CTGGAAGATGAAACCGAAACCTTAAGCATTCCGCTGCCTGCGGTTGTTGCTGTTTCCACTGATATCAACTCCCCA
CAAATTCCTTCGATGAAAGCCATTCTCGGCGCGGCGAAAAGCCCGTCCAGGTATGGTCGGCGGCGGATATTGGT
TTTAACGCAGAGGCAGCCTGGTCAGAACAACAGGTTGCCGCGCCGAAACAGCGCGAACGTCAGCGCAACGGCCGG
CCAAGCACGCGGGGATTGCGTACACGCGTTTGTACAGAAAAAAAGAAAATTTGAAATATAAATAACGTTCTTA
ATACTAACATAACTATAAAAAAATAAATAGGGACCTAGACTTCAGGTTGTCTAACTCCTTCCTTTTCGGTTAGAG
CGGATGTGGGGGGAGGGCGTGAATGTAAGCGTGACATAACTAATTACATGATATCGACAAAGGAAAGGGGCCTG
TTATCAAGCTAGTTGTCTGTCGGGAGTGTGCGTCGTCTAACACTCTCCTCTGTTGAAGGACTTAGTAACTGGGG
AGGACAAACCCTGATGTGTAACCTCACAAGCGTAAACCTTGTGCTTCTCGTAATCAGCCTTGGACAAAGTCAAAG
TGGAGGACAAGGAGTAAGTGGAGTCCTTAGAGTCTTGCTCAGTAACGGATTCTTGGGAGTTACCGGATTGCAAAG
CGTTGTCAACCTTCCACTGAACCTTAGCCTCTCTTGGGTAGAAGTTGTTCAACAAACAAACAACGGAAGCTGTAC
CAGACTTCAACTGTTCGTCGGATGGTGGGAAAATGAAAACGGATGGAGCAGCAACAGTTCTCTTGATCTCAACCT
TAGTACCCTGTCCGAAAGTTGGTGGAGTAGTGTAGTGCTGCTGACAGTAGTAAGTAGCGAAATCTTCTGGTTGCA
AGGAGGAGATAGTCAAAGTGAAGTCAGTACCGGATCTGGAACCAGAGAATCTGGATGGAACACCAGAGTACAAGA
AGGAAGCGGATAGATCAACACTTTGGAGCCTTTCCTGGCTTCTGTTGATACCAAGCAACAGCAGTATTAACGT
CCTGGGAAGCTCTACAAGTGATAGTAACTCTGTCACCAACGGAAGCAGACAAAGAAGATGGGGATTGAGTCATTT
GGATGTCAGCCAAAGCAGAAGAAGCAGCGAACAAAACAGCAGTGAAGATGGATGGGAATCTCATCGTTTCGAATA
ATTAGTTGTTTTTTGATCTTCTCAAGTTGTCGTTAAAAGTCGTTAAAATCAAAAGCTTGTCAATTGGAACCAGTC
GCAATTATGAAAGTAAGCTAATAATGATGATAAAAAAAAGGGTTTAAGACAGGGCAGCTTCCTTCTGTTTATATAT
TGCTGTCAAGTAGGGGTTAGAACAGTTAAATTTTGATCATGAACGTTAGGCTATCAGCAGTATTCCCACCAGAAT
CTTGGAAGCATACAATGTGGAGACAATGCATAATCATCCAAAAAGCGGGTGTTTCCCCATTTGCGTTTCGGCACA

```
GGTGCACCGGGGTTCAGAAGCGATAGAGAGACTGCGCTAAGCATTAATGAGATTATTTTTGAGCATTCGTCAATC
AATACCAAACAAGACAAACGGTATGCCGACTTTTGGAAGTTTCTTTTTGACCAACTGGCCGTTAGCATTTCAACG
AACCAAACTTAGTTCATCTTGGATGAGATCACGCTTTTGTCATATTAGGTTCCAAGACAGCGTTTAAACTGTCAG
TTTTTGGGCCATTTGGGGAACATGAAACTATTTGACCCCACACTCAGAAAGCCCTCATCTGGAGTGATGTTCGGGT
GTAATGCGGAGCTTGTTGCATTCGGAAATAAACAAACATGAACCTCGCCAGGGGGGCCAGGATAGACAGGCTAAT
AAAGTCATGGTGTTAGTAGCCTAATAGAAGGAATTGGAATGAGCGAGCTCCAATCAAGCCCAATAACTGGGCTGG
TTTTTCGATGGCAAAGTGGGGTGTTGAGGAGAAGAGGAGTGGAGGTCCTGCGTTTGCAACGGTCTGCTGCTAGTG
TATCCCCTCCTGTTAGGTCCGCCGGCGTTGGACGAGCGGCAAGAATAAAAGTTGCTCAGCTGAACTTATTTGGTT
ACTTATCAGGTAGTGAAGATGTAGAGAATATATGTTTAGGTATTTTTTTTAGTTTTTCTCCTATAACTCATCTT
CAGTACGTGATTGCTTGTCAGCTACCTTGACAGGGGCGCATAAGTGATATCGTGTACTGCTCAATCAAGATTTGC
CTGCTCCATTGATAAGGGTATAAGAGACCCACCTGCTCCTCTTTAAAATTCTCTCTTAACTGTTGTGAAATCAT
CTTCGAAGCAAATTCGAGTTTAAATCTATGCGGTTGGTAACTAAAGGTATGTCATGGTGGTATATAGTTTTTCAT
TTTACCTTTTACTAATCAGTTTTACAGAAGAGGAACGTCTTTCTCAAGATCGAAATAGGACTAAATACTGGAGAC
GATGGGGTCCTTATTTGGGTGAAAGGCAGTGGGCTACAGTAAGGGAAGACTATTCCGATGATGGAGATGCTTGGT
CTGCTTTTCCTTTTGAGCAATCTCATTTGAGAACTTATCGCTGGGGAGAGGATGGACTAGCTGGAGTCTCAGACA
ATCATCAACTAATTTGTTTCTCAATGGCACTGTGGAATGAGAATGATGATATTTTGAAGGAGCGATTATTTGGGG
TCACTGGAGAGGCTGCAAATCATGGAGGATGTTAAGGAGCTTTATTATTATCTTGATAATACACCTTCTCACT
CTTATATGAAATACCTTTACAAATATCCACAATCGAAATTTCCTTACGAAGAATTGATTTCAGAGAACCGTAAAC
GTTCCAGATTAGAAAGAGAGTACGAGATTACTGACTCTGAAGTACTGAAGGATAACAGATATTTTGATGTGATCT
TTGAAATGGCGGCGGTTTAAACGCGTGGCCGTGCCGTC pTDH3 > VTH1 MS637 (SEQ ID NO: 64)
GACGGCACGGCCACGCGTTTAAACCGCCACCGTCAATATGAAGAATAACACTAACCAGTA
TTTTGAAAAGAAGAAAGCCATTAATGAAATCGTCAAATCAATTCATTCCAATTTGGAAGC
TTCTTTATTTAGTTCACTAAAACGCTCAGATATGGCATCTCAAACTCTCCCCTATGTTTA
TCATATCATACTGCCTAACTTCAAAAACATGGCCAGATTAATCAGCCTGAAACCTGAAGA
AAAGATCAAACTTACGGAAGCTGCAAAAGTTCTTAAAGAGTTTGGCTTCACGATTGAGCA
AGCAAAAGATGAAACTTTCACTTACATTCAAAACTAGTTCCGCCAATTGATACCGTAGT
CAATTGTCAGAACGAATTATCGCATCAAAAGTCACTTTGCGCACGAGCTAATCAGATTCT
CCCATACATTGAGATTGAGTTGAAAAGGTTGAACATCACCAAGAGACACCTAACCGATTC
TGAGCAAGACTTCAAGAAACTACAAGGTACTTCAAAGAGAAGAATCACAGGGTTGACCTC
CCCTAGTAATCGACAGTCGCGTGCCGCATCTCTTCAGGAGGGGGGCAGACTCAAAATCA
GCTGGGTACCTCTATAGATTTTTTCGCCAAATCGCTTTCCCGAGATGGAAGCTCAGGCAG
AACGACACCTGCACCTCAGACGAACTCTCAGAGAGGCACCACCGGACGTATTTGGGTCCG
TTATAACGAAGGGTTCTCAAATGCAGTTCGTAGAAACATCACATGGGAAGAGCTGTGGAA
TTTTTAAATGTCCTCCATAATTTCATGCGGACCTTGCATAGTTTATATAATCATACTGTA
CCAACCAACATCCACACAAGGAGTTTTCGGCCTCAACATATTATCGAAACCATCTCCCTG
TCCCTTACTCAGATCCTATTTTTTCTTACTCAATTGAACGCTCGTCCAACGCCGGCGGAC
CTCCTTAACTACGTTAGGTCAGTGATGACAATGGACCAAATTGTTGCAAGGTTTTTCTTT
TTCTTTCATCGGCACATTTCAGCCTCACATGCGACTATTATCGATCAATGAAATCCATCA
AGATTGAAATCTTAAAATTGCCCCTTTCACTTGACAGGATCCTTTTTTGTAGAAATGTCT
TGGTGTCCTCGTCCAATCAGGTAGCCATCTCTGAAATATCTGGCTCCGTTGCAACTCCGA
ACGACCTGCTGGCAACGTAAAATTCTCCGGGGTAAAACTTAAATGTGGAGTAATGGAACC
AGAAACGTCTCTTCCCTTCTCTCTCCTTCCACCGCCCGTTACCGTCCCTAGGAAATTTTA
CTCTGCTGGAGAGCTTCTTCTACGGCCCCCTTGCAGCAATGCTCTTCCCAGCATTACGTT
GCGGGTAAAACGGAGGTCGTGTACCCGACCTAGCAGCCCAGGGATGGAAAAGTCCCGGCC
GTCGCTGGCAATAATAGCGGGCGGACGCATGTCATGAGATTATTGGAAACCACCAGAATC
GAATATAAAAGGCGAACACCTTTCCCAATTTTGGTTTCTCCTGACCCAAAGACTTTAAAT
TTAATTTATTTGTCCCTATTTCAATACCTCCCGCGACCTCCAAAATGAACTACCTTCAC
AATGAGGACATTGACATTGTTGGTCTACTTCGTAGTGGCTGCCTTAGCTTTCACCCCGCA
GACCAACTCCAGAATTTTTAAAGGTTACCCAAAGAAAGTGGTTTATTTTGACGACACTGC
CAGCGTTGTCTACCATGATGGCTCTGACAATGAGATCTATTATTCCAAAGATGATGGTGT
CACTTGGACTCAACTAGATCTTGGTGGGGCGTCCGCTCATCAAGTAATTGTTCACCCTTT
TGACCCTTCTACTGCCTATATTTTGACCACTAGTGAAACTCACTTCGTCACCACAGATAG
CGGATTTACTTGGAATAAGGTTTCCTCTCCAGAGCCTCCAGTAACCAACGAGTTTCCAAC
GTTGAGCCAAGAGTCCTCCTCATTGACCCTGAATTCCAAGAACTTTGAGTATGTTCTGTT
TGCAGGCCAATGTACAGACGGATCAGAAATTTGCAACAGAAAGTACTACTATTCCTTGGA
TAACATGAGAACTTTCAACGAGCTCATTGAAGCTCACAGCTGTTTGTTTGTCGATACTGC
CGATGCCATTGCGGGTGATCATTCCCCAAACGCTGTTATCTGTGCCATCACCAACCCTGA
CGGAAAACTGTCTTTGGTGAAAACCGCCAACTTCTTCAAAGACGGCATAGACTATGTCTC
TAGTGGTGGTGGTCTTATTGAGAATCCTGAACTGCTGGGCGCCTCACACAACTACATCTT
GGCTGTTGGTTCTCATCTTTTGCACAACAAAGACAAGTTTGTATACATCTCATTTGATGG
TTCGAACTTCAACAAAGTGACGGTGTTTAAACCCCAGCGCCTGGCGGG pTDH3 > CNE1, MS628 (SEQ ID NO: 65)
GACGGCACGGCCACGCGTTTAAACCGCCTCTCTGCTCTTCAAGAAGTAAACGCTGGGCG
GCAAAGAAGGAAAAGTCCAATAAAAGTATCTGTAAGAGGTGGAAGTGCTCAGATAGTGCG
AAGAGAGGAATAAATGAATGCAAGAGCGCGATGGAGTGTAGCGTGATTACATCATCAGAT
GCTACATTGATTCTCTGATATGAATGGTGATGGAACTTTCTAGAGGTTCCTTGAAGAAAT
AAATACATTTACAAGCAGAACTCCACTTTTTCACGGAGAATCATCTAAGTTAGGCATACG
AAGGATCTCGCCTTCGTTGTTTGCACTCATCTCCTGTAGTTTAGCGAGAATCTTGGAGTC
CTTCCACTTTTCAGGCAATGGGGTAACCTCGTAGTTTTTCACGGCCCAGTAATAAATATC
CCAATCCAACTCGTTTAATAAGTCATCATACTCTTCCATCTCTTCCACTCATTGTCGG
TAGATAGCGTTTTGCGAAACGAGACAGAAGAAGGTCTGTTTCCAAGATTCCTCTCTTTCT
TGACTGATAAACCAGACGGCGTCTCTTGACATCTTCCGACTCGTTATCACGTTTCAGAGG
TTCAACTTTCAGTATCAGCTCCTGCCTCAAGAAGGGGAGAGAATGAAAAGATTTCGAAAA
CACCCTTGGACAAGTCTTGCTACCTTGAAACTGAGTTCTTTGGAAAAGCCGGAGCATAAT
GGGTGAATTAAGCAGAAAGAAGGTAACTGATTTGCTGAGACCCAAATCATCTACAGTTTC
GCGAAGCATAAAGTTCCACACTGATTTTCTGGGGAAGAACTGGTAAACCACATGTTGTCTC
```

```
CATTCCACGATAAACCGTTCAAGCAAGGCCGTCTTAGAATGCACAAGACAATTTAGGTAA
ACTACCTTTCCTGGAAGCGAAAGCAGACGTTACAATCTGTTTCATCCCCAACTGCACTC
CTCTCTCCTCTGCTAGCCAAGACGATCTTTCATAGAATTTGATGGAATTTACGCGAAATC
GCCACGTAATCATATTTCGAACAGCGCTCGTCCAACGCCGGCGGACCTCCTTAACTACGT
TAGGTCAGTGATGACAATGGACCAAATTGTTGCAAGGTTTTTCTTTTTCTTTCATCGGCA
CATTTCAGCCTCACATGCGACTATTATCGATCAATGAAATCCATCAAGATTGAAATCTTA
AAATTGCCCCTTTCACTTGACAGGATCCTTTTTTGTAGAAATGTCTTGGTGTCCTCGTCC
AATCAGGTAGCCATCTCTGAAATATCTGGCTCCGTTGCAACTCCGAACGACCTGCTGGCA
ACGTAAAATTCTCCGGGGTAAAACTTAAATGTGGAGTAATGGAACCAGAAACGTCTCTTC
CCTTCTCTCTCCTTCCACCGCCCGTTACCGTCCCTAGGAAATTTTACTCTGCTGGAGAGC
TTCTTCTACGGCCCCCTTGCAGCAATGCTCTTCCCAGCATTACGTTGCGGGTAAAACGGA
GGTCGTGTACCCGACCTAGCAGCCCAGGGATGGAAAAGTCCCGGCCGTCGCTGGCAATAA
TAGCGGGCGGACGCATGTCATGAGATTATTGGAAACCACCAGAATCGAATATAAAAGGCG
AACACCTTTCCCAATTTTGGTTTCTCCTGACCCAAAGACTTTAAATTTAATTTATTTGTC
CCTATTTCAATACCTCCCGCGACCTCCAAAATCGAACTACCTTCACAATGAAGATCTCTA
CCATTGCAAGTTCTACGTTGTTCGCTGTTGGTGCTTTAGCCGAATCCGAACCCGCTGAGT
TCAGACCCTTGGAAGCTCAGTTGGACAAGTCATCTTTCTTTGAACAATTCGACAAGGAAC
CGAAACTCGGCGACACCTGGAAGATCTCCCATGCCGTTAAGAATGAAGAATTCACTTATG
TTGGAGAATGGGCCATTGAGGAACCTGTTGTCTATCCTGGATTCAAGAAGGACAGGGGTC
TGGTTGTGAAATCTGAGGCAGCTCACCACGCAATATCTGCCCAATTACCACAGGTATTTG
ACAACACTGACAATACGTTGGTCTTGCAATACGAAGTCAAGCTTCAACAAGGATTGAACT
GTGGAGGTGCTTATGTTAAATTATTGAGTGCTGAGGGTCTGAACAAGAATGAGTTCTCTA
ACGAGACCCCTTATCAAGTCATGTTTGGTCCTGATAAATGTGGAACCACGAATAAAGTGC
ACTTGATTATTAAGAGGAAGAACCCAGCCACCGGCGAATATGAGGAACATCAATTGGCTA
CTCCTCCAATGGGTAGAATCGTCAAGACTACTTCTCTATACACCCTGATTATCAAGCCCA
ATAATGACTTTGAAATCAGAATCAACGGTGAGGTTGCTAAAGCTGGTAACTTGTTGAACG
AGAAGTTGATAAAGCCACCATTTGGCGCTCCGAAGGAGATTGACGATCCGGAAGACCAAA
AACCCGAAGATTGGGTTGATGAAGACATGATCCCAGATCCAGATGCTGTCAAGCCTGAAG
ATTGGGACGAGTCCGAGCCATTGCGAATCGTCGATCCGGAAGCTGTGAAACCAGAAAACT
GGAACGAAGATGCTGAATTGTACATCCCTGATCCAGAGGCCAACCAAGCCCGAAGACTGGG
ACGATGAAGAGGATGGCGAATGGGTTGCTCCTGTTATTCCAAATCCAGAATGCGCAGATA
TTGGATGTGGCCCTTGCGGTGTTTAAACCCCAGCGCCTGGCGGG pTDH3 > ECM10, MS766 (SEQ ID NO: 66)
GACGGCACGGCCACGCGTTTAAACCGCCGATTGTCTTCAAACATTTACACTGAGTGTTGG
AACCATTAAGTTGCCATATTTGAGCCGTCGAATCTTTGGCGACGGTGACAAATATCAGTT
CATCAACTGTATCCCAAGCAATGCAATAGACTGGCTTGTTAGAGGTTGTATTGATCTGCA
ATAAAGAGTCCCATACATTTTCCTTGAACCTTTTCCATATGCGAGGGTTTTATCAGATC
TTGAATACGCCAATCTATTTCCCTTGTTGAATTCTAAAGTGATGATATCAGTGCTAGTTC
GGTGATTTTCTAAAGAGCCATCATTCAACTCCGTTGATTTCAGATCAGTAAAAAGCTGCT
TGTCCCTAGCTAGTGAAGGGTTGGTCATTATAGAGGCCTTCAAACAATACTTTTCAAAAT
AGACACGCCGCGCGAATCCTCACGATAGCGAAATACCAACTCCACACGATGTTACCACGTA
ACATTTCTCCTCTGATCAAATGGCTCCTCAAACACCAAGGCAACGTATCGCAAACGAAAA
ATTCGTAAAGAGAGCTGAAGCTCAGCAGGGTAAGGTGAAGAAGGCTAGATCCAAGCGTGA
ATTTCCAGTTTCGACTAAGTGGGTTATCATATTGCTCTTCTTGCTGATTGGGGGAGGGGT
CCTGGAGATTTTGAGATTGTTTTTTTGAATGATCTTTTCAAAGGTCTAGGTCTTTTTGGA
AGGAAATGGTTATACTTTGGCCTTTCATTATTTGAGAGGATAGTCGTATTTTTCTACCGG
GAGAAGGTAGGCATAACGTTAATTGCGAATTTTCACTTACTTTAGATGGGTACTGATCTT
CAACTCACGATAATTTCATTGCACCATGTATCTCTAAACTGGCGTGTCGGAACTCACACA
CCATTGGAACTTATTGATTAACAATACATAGATTAATTGACTCGCCTGATAATACTAAT
CACCGTTCACTACTTCTCTTAGTATCTTCTCCTACTGGAGTCGTTCTACGCTCGTCCAAC
GCCGGCGGACCTCCTTAACTACGTTAGGTCAGTGATGACAATGGACCAAATTGTTGCAAG
GTTTTTCTTTTTCTTTCATCGGCACATTTCAGCCTCACATGCGACTATTATCGATCAATG
AAATCCATCAAGATTGAAATCTTAAAATTGCCCCTTTCACTTGACAGGATCCTTTTTTGT
AGAAATGTCTTGGTGTCCTCGTCCAATCAGGTAGCCATCTCTGAAATATCTGGCTCCGTT
GCAACTCCGAACGACCTGCTGGCAACGTAAAATTCTCCGGGGTAAAACTTAAATGTGGAG
TAATGGAACCAGAAACGTCTCTTCCCTTCTCTCTCCTTCCACCGCCCGTTACCGTCCCTA
GGAAATTTTACTCTGCTGGAGAGCTTCTTCTACGGCCCCCTTGCAGCAATGCTCTTCCCA
GCATTACGTTGCGGGTAAAACGGAGGTCGTGTACCCGACCTAGCAGCCCAGGGATGGAAA
AGTCCCGGCCGTCGCTGGCAATAATAGCGGGCGGACGCATGTCATGAGATTATTGGAAAC
CACCAGAATCGAATATAAAGGCGAACACCTTTCCCAATTTTGGTTTCTCCTGACCCAAA
GACTTTAAATTTAATTTATTTGTCCCTATTTCAATACCTCCCGCGACCTCCAAAATCGAA
CTACCTTCACAATGTTGTCATCAAGATGGTGTTCATGTAAAAAGCAGAGTCCAAGTCGAC
AAGTAGGTCAGTTACTGCGCTACATGTCTAGCAAGGTAATTGGAATTGATTTAGGAACTA
CGAACTCTGCTGTTGCCGTTTTTGAAGGAAAAGAACCAAAAATCCTGGAGAACGAAGAGG
GAAAGAGAACGACACCTTCTATTGTTGCATTTACCCCAGAAACTGTGCTAGTAGGAGAAC
CAGCAAAGAGACAATCTATTCTGAACTATCAGAACACTTTTTATGCTACAAAAAGGCTCA
TTGGTCGCAAGTATTCGGATCCTGAAGTTCAACGGGATATTTCCAACGTTCCTTACAGTA
TAATTGAACATGAAAATGGGGATGCGTGGCTTCAAAACATGCACTCAGGTCAAAAATACT
CCCCCTCTCAAATTGGTAGTTTGATATTGGGAAAGATGAAAGAGATTGCAGAGCTAAATC
TTTCCCAGTCTATTAGCCAGGCTGTGGTCACTGTGCCTGCCTACTTCAACGATTCGCAAA
GACAAGCAACTAAGATTGCTGGTGATTTAGTGGGTCTTAAAGTTTTAAGAGTTATCAATG
AGCCCACCGCTGCTCTTTGGCTTACGGATTGAATAGAAAAATGCGGGATAATTGCCG
TTTACGACCTTGGTGGTGGAACTTTTGATATCTCCATATTGGATATCGAAGCCGGCGTCT
TTGAAGTTATTGCGACGAATGGTGACACACATCTTGGAGGGGAAGATTTTGACCATTTGC
TGGTGGACTACATATTGCAACAGTTTCAATCGCAGACAGGACAAGATCTATCTACTGACC
GTTTGGCCCTGCAAAGAATTCGTCAGGCTGCTGAAAACGGTGTTTAAACCCCAGCGCCTG
GCGGG
``` pTDH3 > ERO1, MS632 (SEQ ID NO: 67)
GACGGCACGGCCACGCGTTTAAACCGCCAGAATCACAAAATTCTTTTCATCTTCAGACAT
GTATATCTGGCTCAGAGATTTGAAGGGAATCTGAAACCTGGTTTTAGACGGAAGGTCAAC
TATGAGGTACAGGCTGTTAGGCCATATGCTTAAAAAAGGAACAGGTAAGGATATGTTTTT
ATTGATGATGGAGATGTGGTGCAAGTGAATCCTGAGAACCTCTTTTTTCTTTTCAAACGC
ATTTTTGTCTTCAATTCCATTCTTCGATCTTTTAACGATGGGAGCGCTTATTTTGTCTAT
GATGTGGCTTTGAAGATCAGCTGTTGTATTCAAACTATCACTTTGAGTCAACGAGTTCTT
AGGTAGTCTTTGAAACCGTGAAAGGGAACCCATTTTCTTCGAACCCAGGGATTTCACTGA
TCCTCTGGCCATTGACGCCGATCGTGAGTTCTGTAGAGTTCCCTTCGTCTTAAGAGAGAG
GGGGAATAATTAAAGATCAAGTAATGTTCTACCTACAAAAGATAAAGATGACCTTAATGT
TTTTAGCGAGGTATAGCTGGGAGTCCCAAAGAAGTAGCTAGGGCGGTGAGAGGATTTTTT
TCTCGTGCGCATATAATCGCTAGCCTAGTTAAAGCATCTTGACGACGTACTAATATCTGG
AAGACTTCAGAGCACAGAAACTATGCCTGGTGAGTTCATGGTGACCGTATTGAGCACATC
CAAAAAGATCTTATTCTCTCCAGTACAATCAGCAGAAGGCCTTATCCATCTTGCTGTTCC
ACTACCTCATTCCAGTATACTTCTAATCATCGCCTCTAGATAAGCCAGACGATCTCAAGA
ACCACCCTCATCTTGAAACGTGGACTCGAGTCGCAATGTCCTGTATCATTCCTACGTCAC
AAGCCATCACTGGGTTCTCTCGCCCCCCTACGAAACGCTAGTCTATTGCTATATGGAACAA
TCTAGACCGTAAGTTAGGGCCACTCTGTTCATTTCTCGTCTTAGTCAGCTGATCCTCGAA
ACGATCTACGCTCGTCAACGCCGGCGGACCTCCTTAACTACGTTAGGTCAGTGATGACA
ATGGACCAAATTGTTGCAAGGTTTTTCTTTTTCTTTCATCGGCACATTTCAGCCTCACAT
GCGACTATTATCGATCAATGAAATCCATCAAGATTGAAATCTTAAAATTGCCCCTTTCAC
TTGACAGGATCCTTTTTTGTAGAAATGTCTTGGTGTCCTCCAATCAGGTAGCCATCT
CTGAAATATCTGGCTCCGTTGCAACTCCGAACGACCTGCTGGCAACGTAAAATTCTCCGG
GGTAAAACTTAAATGTGGAGTAATGGAACCAGAAACGTCTCTTCCCTTCTCTCTCCTTCC
ACCGCCCGTTACCGTCCCTAGGAAATTTTACTCTGCTGGAGAGCTTCTTCTACGGCCCCC
TTGCAGCAATGCTCTTCCCAGCATTACGTTGCGGGTAAAACGGAGGTCGTGTACCCGACC
TAGCAGCCCAGGGATGGAAAAGTCCCGGCCGTCGCTGGCAATAATAGCGGGCGGACGCAT
GTCATGAGATTATTGGAAACCACCAGAATCGAATATAAAAGGCGAACACCTTTCCCAATT
TTGGTTTCTCCTGACCCAAAGACTTTAAATTTAATTTATTTGTCCCTATTTCAATACCTC
CCGCGACCTCCAAAATCGAACTACCTTCACAATGAGGATAGTAAGGAGCGTAGCTATCGC
AATAGCCTGTCATTGTATAACAGCGTTAGCAAACCCTCAAATCCCTTTTGACGGCAACTA
CACCGAGATCATCGTGCCAGATACCGAAGTTAACATCGGACAGATTGTAGATATTAACCA
CGAAATAAAACCCAAACTGGTGGAACTGGTCAACACAGACTTCTTCAAATATTACAAATT
AAACCTATGGAAACCATGTCCGTTTTGGAATGGTGATGAGGGATTCTGCAAGTATAAGGA
TTGCTCTGTCGACTTTATCACTGATTGGTCTCAGGTGCCTGATATCTGGCAACCAGACCA
ATTGGGTAAGCTTGGAGATAACACGGTACATAAGGATAAGGGCCAAGATGAAATGAGCT
GTCCTCAAATGATTATTGCGCTTTGGATAAAGACGACGATGAAGATTTAGTATATGTCAA
TTTGATTGATAACCCTGAAAGATTCACCGGTTATGGTGGTCAGCAATCTGAATCTATTTG
GACTGCGGTCTATGATGAGAACTGTTTCCAGCCGAATGAAGGATCACAATTGGGTCAAGT
TGAAGACCTCTGTTTGGAGAAACAGATCTTTTACCGATTGGTTTCTGGTTTGCATTCTAG
TATCTCCACCCACCTCACAAACGAATATCTGAATTTGAAAAATGGAGCATACGAACCAAA
TTTGAAACAGTTCATGATCAAAGTTGGGTATTTTACTGAAAGAATTCAAAACTTACATCT
CAATTATGTCCTTGTATTGAAGTCACTAATAAAGCTACAAGAATACAATGTTATCGACAA
TCTACCTCTCGATGACTCTTTGAAAGCTGGTCTTAGCGGTTTAATATCTCAAGGAGCACA
GGGTATTAACCAGAGCTCTGATGATTATCTATTTAACGAGAAGGTTCTTTTCCAAAATGA
CCAAAATGATGATTTGAAAAATGAATTCCGTGACAAATTCCGCAACGTGACTAGATTAAT
GGATTGTGTCCACGGTGTTTAAACCCCAGCGCCTGGCGGG

What is claimed is:

1. A method of disrupting a target site in a host cell genome, wherein the host cell is Pichia pastoris, the method comprising:
   (a) contacting a host cell, which comprises a nucleic acid that encodes an RNA-guided DNA endonuclease, wherein the nucleic acid is integrated in a YKU70 gene, thereby reducing non-homologous and joining (NHEJ) activity in the host cell as compared to a host cell in which the YKU70 gene is intact, with:
      (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker
      (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site; and
   (b) selecting a transformed host cell expressing the selectable marker, wherein the host cell has reduced NHEJ activity.

2. The method of claim 1, wherein the method further comprises contacting the host cell with a donor DNA molecule capable homologous recombination with the target site, whereby homologous recombination in the host cell results in integration of the donor DNA molecule at the target site.

3. The method of claim 2, wherein the step of contacting includes contacting the cell with two or more donor DNA molecules capable of homologous recombination with different target sites, whereby homologous recombination in the host cell results in integration of the donor DNA molecules at the different target sites.

4. The method of claim 2, wherein the donor DNA molecule comprises a nucleic acid sequence encoding an antibody.

5. The method of claim 1, wherein the step of contacting includes contacting the cell with two or more second linear nucleic acid molecules, wherein each second linear nucleic acid molecule comprises a nucleic acid encoding a different guide RNA, which guides the DNA nuclease to a different target site.

6. The method of claim 1, wherein the nucleic acid encoding the RNA-guided DNA endonuclease is operably linked to a Pichia pPGK1 promoter.

7. The method of claim 1, wherein the RNA-guided DNA endonuclease is Cas9.

8. The method of claim 7, wherein the nucleic acid sequence encoding the Cas9 is codon optimized for expression in Saccharomyces.

* * * * *

SEQUENCE LISTING

<160> NUMBER OF SEQ ID NOS: 67

<210> SEQ ID NO 1
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aaagctagag ttaccgtaa                                                19

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tcaactgcag tcttgataa                                          19

<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gtgtgaacag agccatgta                                          19

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
atttggagat tttgcgcta                                          19

<210> SEQ ID NO 5
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ttctggagag cactatgac                                          19

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aaccctaaga atctggctc                                          19

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tcaacaagta cttatatga                                          19

<210> SEQ ID NO 8
<211> LENGTH: 19
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 8
attttatgtc tcagcaaga                                                  19

<210> SEQ ID NO 9
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gacatggctc ctatggttt                                                  19

<210> SEQ ID NO 10
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tggctgaaat taggtaaag                                                  19

<210> SEQ ID NO 11
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
agaaaataaa gagtttcta                                                  19

<210> SEQ ID NO 12
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tagatgcagt aggatagggg                                                 19

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gtccactaac tacctttcg                                                  19
```

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aaagataggg aaaaggaaa                                                    19

<210> SEQ ID NO 15
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15 tcagat                                                                   6

<210> SEQ ID NO 16
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
cgcgaatgtt cccccagctt atctcgacag gtggcacttt tcggggaaat gtgcg            55

<210> SEQ ID NO 17
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
gaccaaaata agtaaatatt aattgtcgaa tactttctag agaataggaa cttcgg           56

<210> SEQ ID NO 18
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
cgcacatttc cccgaaaagt gccacctgtc gagataagct gggggaacat tcgcg            55

<210> SEQ ID NO 19
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ccgaagttcc tattctctag aaagtattcg acaattaata tttacttatt ttggtc       56

<210> SEQ ID NO 20
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aaaatcataa atcataagaa attcgcgtcc cattcgccat gccgaagcat gttgcc       56

<210> SEQ ID NO 21
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggcaacatgc ttcggcatgg cgaatgggac gcgaatttct tatgatttat gatttt       56

<210> SEQ ID NO 22
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ctagaactag tggatccccc gggcgctgga gttagcatat ctacaattgg gtg          53

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
gggaggactc tcgtttccta tg                                            22

<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
ttttagagct agaaatagca ag                                            22

<210> SEQ ID NO 25
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
cccctcgagg tcgacggtat c                                              21

<210> SEQ ID NO 26
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
tcttgctgag acataaaatc atctgagacg agcttactcg tttcgtcctc ac            52

<210> SEQ ID NO 27
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
attttatgtc tcagcaagag ttttagagct agaaatagca agttaaaata ag            52

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ctagaactag tggatccccc g                                              21

<210> SEQ ID NO 29
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cgctcgtcca acgccggcgg acct                                           24

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
taacagttat tattcgagat cta                                            23
```

```
<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ggtaccatac ttctccaccg                                              20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ttcgaaactg cagctagcaa                                              20

<210> SEQ ID NO 33
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
ccattgttgc cgataactgt tg                                           22

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cggtatcgct gctttcttta                                              20

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
caataatcaa tgcagcccca g                                            21

<210> SEQ ID NO 36
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 36
gaaaagggta gtgaaaggaa ag                                    22

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
gctaattacg taccagaacc                                       20

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ttgacacctt ggataaaagg g                                     21

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
cagaataact tcatgactgc                                       20

<210> SEQ ID NO 40
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
agtgacgcca acaatacccA tga                                   23

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
ttgtcccact ttgaataatc g                                     21

<210> SEQ ID NO 42
<211> LENGTH: 24

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42 ggagttttt gggctagggg tttg                                              24

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
gctgagcact tcagtcttac g                                                21

<210> SEQ ID NO 44
<211> LENGTH: 164
<212> TYPE: DNA
<213> ORGANISM: Komagataella pastoris

<400> SEQUENCE: 44
tcgagataag ctgggggaac attcgcgaaa atgaaacaag tcggctgtta tagtatattt      60
attataatat tgaaagatct caaaagacta cttattttg aatgaaccaa gtatgaaatc      120
aacctatttg gggttgacca aaataagtaa atattaattg tcga                      164

<210> SEQ ID NO 45
<211> LENGTH: 550
<212> TYPE: DNA
<213> ORGANISM: Komagataella pastoris

<400> SEQUENCE: 45
tgttgtagtt ttaatatagt ttgagtatga gatggaactc agaacgaagg aattatcacc      60
agtttatata ttctgaggaa agggtgtgtc ctaaattgga cagtcacgat ggcaataaac     120
gctcagccaa tcagaatgca ggagccataa attgttgtat tattgctgca agatttatgt     180
gggttcacat tccactgaat ggttttcact gtagaattgg tgtcctagtt gttatgtttc     240
gagatgtttt caagaaaaac taaaatgcac aaactgacca ataatgtgcc gtcgcgcttg     300
gtacaaacgt caggattgcc accacttttt tcgcactctg gtacaaaagt tcgcacttcc     360
cactcgtatg taacgaaaaa cagagcagtc tatccagaac gagacaaatt agcgcgtact     420
gtcccattcc ataaggtatc ataggaaacg agagtcctcc ccccatcacg tatatataaa     480
cacactgata tcccacatcc gcttgtcacc aaactaatac atccagttca agttacctaa     540
acaaatcaaa                                                           550

<210> SEQ ID NO 46
<211> LENGTH: 550
<212> TYPE: DNA
<213> ORGANISM: Unknown
<220> FEATURE:
<221> NAME/KEY: source
<223> OTHER INFORMATION: /note="Description of Unknown:
      Hammerhead sequence"

<400> SEQUENCE: 46
```

```
tgttgtagtt ttaatatagt ttgagtatga gatggaactc agaacgaagg aattatcacc      60
agtttatata ttctgaggaa agggtgtgtc ctaaattgga cagtcacgat ggcaataaac     120
gctcagccaa tcagaatgca ggagccataa attgttgtat tattgctgca agatttatgt    180
gggttcacat tccactgaat ggttttcact gtagaattgg tgtcctagtt gttatgtttc    240
gagatgtttt caagaaaaac taaaatgcac aaactgacca ataatgtgcc gtcgcgcttg    300
gtacaaacgt caggattgcc accactttt tcgcactctg gtacaaaagt tcgcacttcc    360
cactcgtatg taacgaaaaa cagagcagtc tatccagaac gagacaaatt agcgcgtact    420
gtcccattcc ataaggtatc ataggaaacg agagtcctcc ccccatcacg tatatataaa    480
cacactgata tcccacatcc gcttgtcacc aaactaatac atccagttca agttacctaa    540
acaaatcaaa                                                           550
```

<210> SEQ ID NO 47
<211> LENGTH: 68
<212> TYPE: DNA
<213> ORGANISM: Hepatitis delta virus

<400> SEQUENCE: 47

```
ggccggcatg gtcccagcct cctcgctggc gccggctggg caacatgctt cggcatggcg     60
aatgggac                                                              68
```

<210> SEQ ID NO 48
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48

```
atctga                                                                 6
```

<210> SEQ ID NO 49
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49

```
ttttagagct agaaatagca agttaaaata aggctagtcc gttatcaact tgaaaaagtg     60
gcaccgagtc ggtggtgc                                                   78
```

<210> SEQ ID NO 50
<211> LENGTH: 253
<212> TYPE: DNA
<213> ORGANISM: Saccharomyces cerevisiae

<400> SEQUENCE: 50

```
gcgaatttct tatgatttat gatttttatt attaaataag ttataaaaaa aataagtgta     60
tacaaatttt aaagtgactc ttaggtttta aaacgaaaat tcttattctt gagtaactct    120
ttcctgtagg tcaggttgct ttctcaggta tagcatgagg tcgctcttat tgaccacacc    180
tctaccggca tgccgagcaa atgcctgcaa atcgctcccc atttcaccca attgtagata    240
tgctaactcc agc                                                       253
```

<210> SEQ ID NO 51
<211> LENGTH: 1019
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

| | | | | | |
|---|---|---|---|---|---|
| tgttgtagtt | ttaatatagt | ttgagtatga | gatggaactc | agaacgaagg | aattatcacc | 60 |
| agtttatata | ttctgaggaa | agggtgtgtc | ctaaattgga | cagtcacgat | ggcaataaac | 120 |
| gctcagccaa | tcagaatgca | ggagccataa | attgttgtat | tattgctgca | agatttatgt | 180 |
| gggttcacat | tccactgaat | ggttttcact | gtagaattgg | tgtcctagtt | gttatgtttc | 240 |
| gagatgtttt | caagaaaaac | taaaatgcac | aaactgacca | ataatgtgcc | gtcgcgcttg | 300 |
| gtacaaacgt | caggattgcc | accacttttt | tcgcactctg | gtacaaaagt | tcgcacttcc | 360 |
| cactcgtatg | taacgaaaaa | cagagcagtc | tatccagaac | gagacaaatt | agcgcgtact | 420 |
| gtcccattcc | ataaggtatc | ataggaaacg | agagtcctcc | ccccatcacg | tatatataaa | 480 |
| cacactgata | tcccacatcc | gcttgtcacc | aaactaatac | atccagttca | agttacctaa | 540 |
| acaaatcaaa | atctgactga | tgagtccgtg | aggacgaaac | gagtaagctc | gtctcagatg | 600 |
| gatttgatca | atgaaagctg | ttttagagct | agaaatagca | agttaaaata | aggctagtcc | 660 |
| gttatcaact | tgaaaaagtg | gcaccgagtc | ggtggtgcgg | ccggcatggt | cccagcctcc | 720 |
| tcgctggcgc | cggctgggca | acatgcttcg | gcatggcgaa | tgggacgcga | atttcttatg | 780 |
| atttatgatt | tttattatta | aataagttat | aaaaaaaata | agtgtataca | aattttaaag | 840 |
| tgactcttag | gttttaaaac | gaaaattctt | attcttgagt | aactctttcc | tgtaggtcag | 900 |
| gttgctttct | caggtatagc | atgaggtcgc | tcttattgac | cacacctcta | ccggcatgcc | 960 |
| gagcaaatgc | ctgcaaatcg | ctccccattt | cacccaattg | tagatatgct | aactccagc | 1019 |

<210> SEQ ID NO 52
<211> LENGTH: 834
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

| | | | | | |
|---|---|---|---|---|---|
| cccctcgagg | tcgacggtat | cgattgttgt | agttttaata | tagtttgagt | atgagatgga | 60 |
| actcagaacg | aaggaattat | caccagttta | tatattctga | ggaaagggtg | tgtcctaaat | 120 |
| tggacagtca | cgatggcaat | aaacgctcag | ccaatcagaa | tgcaggagcc | ataaattgtt | 180 |
| gtattattgc | tgcaagattt | atgtgggttc | acattccact | gaatggtttt | cactgtagaa | 240 |
| ttggtgtcct | agttgttatg | tttcgagatg | ttttcaagaa | aaactaaaat | gcacaaactg | 300 |
| accaataatg | tgccgtcgcg | cttggtacaa | acgtcaggat | tgccaccact | ttttcgcac | 360 |
| tctggtacaa | aagttcgcac | ttcccactcg | tatgtaacga | aaaacagagc | agtctatcca | 420 |
| gaacgagaca | aattagcgcg | tactgtccca | ttccataagg | tatcatagga | aacgagagtc | 480 |
| ctccccccat | cacgtatata | taaacacact | gatatcccac | atccgcttgt | caccaaacta | 540 |
| atacatccag | ttcaagttac | ctaaacaaat | caaaatctga | ctgatgagtc | cgtgaggacg | 600 |

```
aaacgagtaa gctcgtctca gatggatttg atcaatgaaa gctgttttag agctagaaat      660
agcaagttaa aataaggcta gtccgttatc aacttgaaaa agtggcaccg agtcggtggt      720
gcggccggca tggtcccagc ctcctcgctg gcgccggctg ggcaacatgc ttcggcatgg      780
cgaatgggac ttttttgtt ttttatgtct gcccggggga tccactagtt ctag             834
```

<210> SEQ ID NO 53
<211> LENGTH: 1825
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 53

```
gacggcacgg ccacgcgttt aaaccgccaa gatggtgatt ccagcgttc gaaaagcctg        60 tagtacccag aattttgatc aaagtgtcct cttagccgtg gcatccgcgg ctgtcatctt      120
gatccttctt cgcatgagca cttacgtgat gctgataaga tgggcacgcc acaacactag      180
ggccaagacc tcgcctagtg gtggcgacta tctaaagggc tcacctaaca cctctttagc      240
ggggattgaa gacattcata cacgaagtct gctgtatggg tcagacgaga aaatgccgca      300
atctaaagaa gaacaaaggt cccacaatgc gaatcgtgat ggtgataaat cattggctca      360
ggtcagtaga tttgaaatgc atgataaacg catatggtga gagccgttct gcacaactag      420
atgttttcga gcttcgcatt gtttcctgca gctcgactat tgaattaaga tttccggata      480
tctccaatct cacaaaaact tatgttgacc acgtgctttc ctgaggcgag gtgttttata      540
tgcaagctgc caaaaatgga aaacgaatgg ccattttcg cccaggcaaa ttattcgatt      600
actgctgtca taaagacagt gttgcaaggc tcacattttt ttttaggatc cgagataaag      660
tgaatacagg acagcttatc tctatatctt gtaccattcg tgaatcttaa gagttcggtt      720
agggggactc tagttgaggg ttggcactca cgtatggctg ggcgcagaaa taaaattcag      780
gcgcagcagc acttatcgat gcatgcaagg cgagaaaaat aaagaacaaa aacacacctt      840
gctaagacca caacctttca aattttgaga ttgttattct ttcatcctaa aacaccaccg      900
tcctatctct tgggaacgta catatcattg agcttggttc attgatacat cactgtatct      960
aactctcctt tttcgctcgt ccaacgccgg cggacctcaa aaaggatcta aaataagac     1020 agtagtggac ttatattcat accatatgat gggtgtttgc tcactcgtat ggatcaaaat     1080
tccatggttt cttctgtaca acttgtacac ttatttggac ttttctaacg gttttctgg      1140 tgatttgaga agtccttatt ttggtgttcg cagcttatcc gtgattgaac catcagaaat     1200
actgcagctc gttatctagt ttcagaatgt gttgtagaat acaatcaatt ctgagtctag     1260
tttgggtggg tcttggcgac gggaccgtta tatgcatcta tgcagtgtta aggtacatag     1320
aatgaaaatg tagggggttaa tcgaaagcat cgttaatttc agtagaacgt agttctattc     1380
cctacccaaa taatttgcca agaatgcttc gtatccacat acgcagtgga cgtagcaaat     1440
ttcactttgg actgtgacct caagtcgtta tcttctactt ggacattgat ggtcattacg     1500
taatccacaa agaattggat agcctctcgt tttatctagt gcacagccta atagcactta     1560
agtaagagca atggacaaat ttgcatagac attgagctag atacgtaact cagatcttgt     1620
tcactcatgg tgtactcgaa gtactgctgg aaccgttacc tcttatcatt tcgctactgg     1680
ctcgtgaaac tactgatga aaaaaaaaa gagctgaaag cgagatcatc ccattttgtc       1740
atcatacaaa ttcacgcttg cagttttgct tcgttaacaa gacaagatgt ctttatccgg     1800
```

```
tgtttaaacc ccagcgcctg gcggg                                         1825
```

<210> SEQ ID NO 54
<211> LENGTH: 1865
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
gacggcacgg ccacgcgttt aaaccgccgc agggtcccac acagaccaaa tccaagttat     60
tccctaaggg atggttttca gagagagaag aaactataat ggtaaaccgg ttgttgcggg    120
atgacccctc taagagtgat atgcacaata gacagtctgt tacgccaaaa gaactgtgga    180
aagtgttggg agactacgat ctatggccta tatacgcatt ggccatggta ttttccattc    240
cccagatacc gataaagaga taccttactc ttactttgag ggcattagag ttcactacca    300
ctgagatcaa tctcttaaca atccctgctt cgtttctggc gggaatcatg tcaattgcta    360
tttcattagt cagtgagttc ttcaatgaag gtttgattat cggtatattg tgtcaattct    420
ggttgcttat tatggttatc attgaataca cctctgtgga aaagatatct ccctggggac    480
aatatgtgtt gcaactgttc gttgttggtg ccccagtccc ccaaccggta ctaatcggtc    540
tatgttcccg taactcatat tcggttagaa ctagaacaat aagtgcatca ttgttcaaca    600
ttgtggttca attgtcgaac attgctggtg cttatatcta cagggaagac gataagcctt    660
tgtacaagag aggtaacaga cagttaattg gtatttcttt gggagtcgtt gccctctacg    720
ttgtctccaa gacatactac attctgagaa acagatggaa gactcaaaaa tgggagaagc    780
ttagtgaaga agagaaagtt gcctacttgg acagagctga aaggagaac ctgggttcta    840
agaggctgga cttttgttc gagagttaaa ctgcataatt ttttctaagt aaatttcata    900
gttatgaaat ttctgcagct tagtgtttac tgcatcgttt actgcatcac cctgtaaata    960
atgtgagctt ttttccttcc attgcttggt atcttccttg ctgctgtttc gctcgtccaa   1020
cgccggcgga cctgagacgg aaaacggaga aggagaacg gagaacgaag aacgaaggga   1080
gagagaagca aagggaagag caaggtattc tggagagatt aagaaaatag tagaatagat   1140
ttaacgaaac tgaaactgaa agaccgaaaa agaatgcag aaattaaaca ccatagggca   1200
gattgattcc gtaatcggtt tcttgctact atatctttct aggctgtcta taatccttt    1260
ataatttaat ctgctaatat cgctgtcacg attattgaca tcgactgtat ttcaacacac   1320
aggtcttaca gatagcatgg ggtttccagt atttgattga catttccgtt tttgcatagt   1380
ccataatata aggatcaaaa acatgagatg tcgcaaggcc tcttaaacat gaaatctccg   1440
tttaccttcc gccatacaac cttacgcata cagcagctcg gtttctacat agagtctttt   1500
caagaaccgg ggtaaaaacc gttttacata gaaagaggta aaacgttgtg atcatgtgac   1560
cgctgaacat ctccggaacc aacacttcgc gatctttttt cgtctgtcac atactcaagg   1620
taaactaagt ttcacaacac gaaggctccg tatcataaat cctcagagtt gaagcactgg   1680
cccccatcta ataaatactc cgaaatgagt caaatccagt caagccaagt gggggcgaaa   1740
aatatgcaaa ccgcacagcc tcaggctcaa caaagaccaa tcaatgggtc tgtgaccctg   1800
agcaatggcc agaggataaa ccctcagaac ttgactccgg tgtttaaacc ccagcgcctg   1860
gcggg                                                              1865
```

<210> SEQ ID NO 55
<211> LENGTH: 1928
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
gacggcacgg ccacgcgttt aaaccgcccg ttctgatggc ttgatgaccg ttgtattgcc      60
tgtcactata gccaggggta gggtccataa aggaatcata gcagggaaat taaaagggca     120
tattgatgca atcactccca atggctctct tgccattgaa gtctccatat cagcactaac     180
ttccaagaag gacccttca agtctgacgt gatagagcac gcttgctctg ccacctgtag      240
tcctctcaaa acgtcacctt gtgcatcagc aaagacttta ccttgctcca atactatgac    300
ggaggcaatt ctgtcaaaat tctctctcag caattcaacc aacttgaaag caaattgctg    360
tctcttgatg atggagactt ttttccaaga ttgaaatgca atgtgggacg actcaattgc    420
ttcttccagc tcctcttcgg ttgattgagg aacttttgaa accacaaaat tggtcgttgg    480
gtcatgtaca tcaaaccatt ctgtagattt agattcgacg aaagcgttgt tgatgaagga    540
aaaggttgga tacggtttgt cggtctcttt ggtatggccg gtggggtatg caattgcagt    600
agaagataat tggacagcca ttgttgaagg tagagaaaag gtcagggaac ttgggggtta    660
tttataccat tttaccccac aaataacaac tgaaaagtac ccattccata gtgagaggta    720
accgacggaa aaagacgggc ccatgttctg ggaccaatag aactgtgtaa tccattggga    780
ctaatcaaca gacgattggc aatataatga atagttcgt tgaaaagcca cgtcagctgt     840
cttttcatta actttggtcg gacacaacat tttctactgt tgtatctgtc ctactttgct    900
tatcatctgc acagggcaa gtggatttcc ttctcgcgcg gctgggtgaa aacggttaac     960
gtgaacgctc gtccaacgcc ggcggacctg ccttggggga cttcaagtct ttgctagaaa   1020
ctagatgagg tcaggccctc ttatggttgt gtcccaattg ggcaatttca ctcacctaaa   1080
aagcatgaca attatttagc gaaataggta gtatattttc cctcatctcc caagcagttt   1140
cgtttttgca tccatatctc tcaaatgagc agctacgact cattagaacc agagtcaagt   1200
aggggtgagc tcagtcatca gccttcgttt ctaaaacgat tgagttcttt tgttgctaca   1260
ggaagcgccc tagggaactt tcgcactttg gaaatagatt ttgatgacca agagcgggag   1320
ttgatattag agaggctgtc caaagtacat gggatcaggc cggccaaatt gattggtgtg   1380
actaaaccat tgtgtacttg gacactctat tacaaaagcg aagatgattt gaagtattac   1440
aagtcccgaa gtgttagagg attctatcga gcccagaatg aaatcatcaa ccgttatcag   1500
cagattgata aactcttgga aagcggtatc ccatttcat tattgaagaa ctacgataat   1560
gaagatgtga gagacggcga ccctctgaac gtagacgaag aaacaaatct acttttgggg   1620
tacaatagag aaagtgaatc aagggaggta tttgtggcca taatactcaa ctctatcatt   1680
aatgtggttc ttttggtagc aaaaatcttt gttgtttttgt tcagttcctc actctcattg   1740
atggcttcgt tagttgactc cgtgatggat ttcttatcta ctttgatcat atatgtttct   1800
aactcttttg ctgggaaaag agacaagaat gagtatccag ttggaaggtc aaggttggag   1860
cccttaggag ttcttgtctt ttccgtaatc ataattgtct cggtgtttaa accccagcgc   1920
ctggcggg                                                              1928
```

<210> SEQ ID NO 56
<211> LENGTH: 1963
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56

| | | | | | |
|---|---|---|---|---|---|
| gacggcacgg | ccacgcgttt | aaaccgccaa | ggcatatagg | cgagggagag | ttagctagca | 60 |
| tacaagataa | tgaaggatca | atagcggtag | ttaaagtgca | caagaaaaga | gcacctgttg | 120 |
| aggctgatga | taaagctcca | attacattgc | cacagagaaa | cacagtaaca | gaaataggag | 180 |
| gggatgcacc | acgagaagag | cattcagtga | acaactttgc | caaattcata | accccaagcg | 240 |
| ctaataagcc | aatgtcaaag | tcggctacta | acattaatag | tacaacaact | atcgattttc | 300 |
| aaccagatgt | ttgcaaggac | tacaaacaga | caggttactg | cggatatggt | gacacttgta | 360 |
| agttttttgca | cctgagggat | gatttcaaac | agggatggaa | attagatagg | gagtgggaaa | 420 |
| atgtccaaaa | gaagaagcat | aatactctca | aagggggttaa | ggagatccaa | atgtttaatg | 480 |
| aagatgagct | caaagatatc | ccgtttaaat | gcattatatg | caaaggagat | tacaaatcac | 540 |
| ccgtgaaaac | ttcttgcaat | cattattttt | gcgaacaatg | tttcctgcaa | cggtcaagaa | 600 |
| gaaaaccaaa | ttgtattata | tgtggcagag | acactttagg | agttgcttta | ccagcaaaga | 660 |
| agttgtccca | atttctggct | aagatacata | ataatgaaag | taataaagtt | tagtaattgc | 720 |
| attgcgttga | ctattgattg | cattgatgtc | gtgtgatact | ttcaccgaaa | aaaaacacga | 780 |
| agcgcaatag | gagcggttgc | atattagtcc | ccaaagctat | ttaattgtgc | ctgaaactgt | 840 |
| ttttttaagct | catcaagcat | aattgtatgc | attgcgacgt | aaccaacgtt | taggcgcagt | 900 |
| ttaatcatag | cccactgcta | agccagaatt | ctaatatgta | actacgtacc | tttccttttta | 960 |
| ataaatgatc | tgtattttcc | acctagtagc | agatcaaatt | gttcaacttt | aagtctttgg | 1020 |
| tccctcaagc | gagagaactt | gcgcgctcgt | ccaacgccgg | cggacctcgg | aggaatgcaa | 1080 |
| ataataatct | ccttaattac | ccactgataa | gctcaagaga | cgcggtttga | aaacgatata | 1140 |
| atgaatcatt | tggattttat | aataaaccct | gacagttttt | ccactgtatt | gttttaacac | 1200 |
| tcattggaag | ctgtattgat | tctaagaagc | tagaaatcaa | tacggccata | caaaagatga | 1260 |
| cattgaataa | gcaccggctt | ttttgattag | catatacctt | aaagcatgca | ttcatggcta | 1320 |
| catagttgtt | aaagggcttc | ttccattatc | agtataatga | attacataat | catgcactta | 1380 |
| tatttgccca | tctctgttct | ctcactcttg | cctgggtata | ttctatgaaa | ttgcgtatag | 1440 |
| cgtgtctcca | gttgaacccc | aagcttggcg | agtttgaaga | gaatgctaac | cttgcgtatt | 1500 |
| ccttgcttca | ggaaacattc | aaggagaaac | aggtcaagaa | gccaaacatt | ttgatccttc | 1560 |
| ccgagttagc | attgactggc | tacaattttc | aaagccagca | gcggatagag | ccttttttgg | 1620 |
| aggaaacaac | caagggagct | agtacccaat | gggctcaaaa | agtatccaag | acgtgggatt | 1680 |
| gctttacttt | aataggatac | ccagaaaaaa | gtttagagag | ccctccccgt | atttacaaca | 1740 |
| gtgcggtact | tgtatcgcct | cagggaaaag | taatgaacaa | ctacagaaag | tccttcttgt | 1800 |
| atgaagctga | tgaacattgg | ggatgttcgg | aatcttctga | tgggtttcaa | acagtagatt | 1860 |
| tattaattga | aggaaagact | gtaaagacat | catttggaat | ttgcatggat | ttgaatcctt | 1920 |
| ataaatttga | agctccggtg | tttaaacccc | agcgcctggc | ggg | | 1963 |

<210> SEQ ID NO 57

<211> LENGTH: 1908
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

| | | | | | |
|---|---|---|---|---|---|
| gacggcacgg | ccacgcgttt | aaaccgccct | gtggactcag | gaccagctca | gcttgacaaa | 60 |
| ccaagacttg | cactccaatg | tgcacaaccc | agtgattgag | cagatcgaaa | cctcatcagg | 120 |
| agtcagattg | tagtatggaa | actttgtat | tctctatgta | cttaaacact | ggtttatttt | 180 |
| tttattgatc | gttatattga | acagtttaca | ctggaacatc | ttcagggtcg | atgtccttaa | 240 |
| tccagtgttg | accaaagatt | gggatcttct | cgaagaaagt | cttttggaac | aaaggccagt | 300 |
| tttcagtgaa | agtgaagacg | gcaaacagac | cggcacctcc | ccagaaagcc | aaaattggaa | 360 |
| aagtagtttt | aatttgggtt | ggagtcaatc | cagcaatttt | cttgacggtg | gtatacttgg | 420 |
| gacctttaac | gtactgaaat | gttagaacat | gtttgtaaaa | atcaaatcat | cactgcagaa | 480 |
| acggtttgtg | tgcctgcacc | ggagggttat | cataatgcca | cttacgttga | ccattttgga | 540 |
| ggtgtttgac | taagttcaaa | tatgaatctc | taagaaaact | aataatcaat | atggtgcgag | 600 |
| cattgattgg | ttggacagct | agtttggaga | agtacacgac | ttagatgaat | ctgcaataag | 660 |
| gaatagtcca | atctgattat | gtaagctctc | cttttggtt | ttcatttcca | tcagctcaag | 720 |
| cttatcatag | ctcaggtccc | ctccagctta | tgatggaata | ggccattatt | ttttgcccta | 780 |
| aaaagtggaa | gtccacaaga | agaaatacaa | atactcaaaa | ttcaaaagtc | ttcctttgag | 840 |
| tggatgcaat | tttacgtagt | ttactgtatg | acgtaactaa | tgaacccttc | cgacacaaag | 900 |
| attgaggtgc | ctcacttaac | gtcattcttc | tatacccacg | agtgcaactg | actaggtctt | 960 |
| attttgttaa | ttgcctcagt | ttctccgaac | gctcgtccaa | cgccggcgga | cctttatgca | 1020 |
| tatactgaaa | caacagaagg | aactacagta | aattcataaa | aagcttaatt | cttactttca | 1080 |
| tctcggcact | gtaaattaac | tcaagttggg | gcaacattgt | gtgtatactc | ttactggcat | 1140 |
| cttttcatct | gaagtcatct | tctactactc | ttctcttctg | tatgacgtaa | tcagctcggc | 1200 |
| agctgtggca | tcgaacaaaa | aaatgaacag | ccatccgtca | tatctcatga | ctgactgagc | 1260 |
| aagaactaag | tcaacaggaa | acctaaaata | agctttccat | ttcttttgcg | ctgaagccaa | 1320 |
| ccactcccca | cacagttgat | gagtggacgc | aaaaccagct | cctataccct | gacagaagag | 1380 |
| tcgccggaat | caacctcaac | aattcaggat | atacgagagg | aagaccaagt | tgctccaggg | 1440 |
| ccccagcaag | aagcacctaa | acagtcacat | atccaaaaat | ggttaagcga | tcatcctaaa | 1500 |
| gtatacgcag | ttttatcttg | gatatggaaa | ttttggttga | acagtggtt | tctcatatgt | 1560 |
| ttgggccctg | cggttgctct | agctcatgca | tacccaaatt | ttgccagaca | tgatggaacc | 1620 |
| attaggtcag | agtatactat | caactacgga | gccgtagcta | tcatattctt | catctctggt | 1680 |
| cttactatga | aaaccaaaga | cttttgaag | aactttggac | actggagagc | ccatttcaca | 1740 |
| gtgttaagct | gctcgtttct | acttacttct | tctatcatt | acggtatagc | gtgcggtata | 1800 |
| agagctgctc | atgattccaa | tatcgatgac | tggatgttag | caggacttat | tgttaccgca | 1860 |
| tgttgtccaa | ccactgtgag | cggtgtttaa | accccagcgc | ctggcggg | | 1908 |

<210> SEQ ID NO 58
<211> LENGTH: 1941
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
gacggcacgg ccacgcgttt aaaccgccgg aggaggtgga accacctgtg caggcggtct    60
gaaagtgttc aagtacggat ctactaccaa atatacatct ggtaacctga acggcgtcag   120
gttagtatac tggaacgaag gaaagttgca aagctccaaa tttgtggttc gatcctctaa   180
ttactctcaa aagcttggag gaaacagcaa cgccgaatca attgacaaca atggtgtggg   240
ttttgcctca gctggagact caggcgcatg gattctttcc aagctacaag atgttaggga   300
gtaccagtca ttcactgaaa agctaggtga agctacgatg agcattttcg atttccacgg   360
tcttaaacag gagacttcta ctacagggct tggggtagtt ggtatgattc attcttacga   420
cggtgagttc aaacagtttg gtttgttcac tccaatgaca tctattctac aaagacttca   480
acgagtgacc aatgtagaat ggtgtgtagc gggttgcgaa gatggggatg tggacactga   540
aggagaacac gaattgagtg atttggaaca actgcatatg catagtgatt ccgactagtc   600
aggcaagaga gagccctcaa atttacctct ctgcccctcc tcactccttt tggtacgcat   660
aattgcagta taagaacttt gctgccagcc agtaatctta tttcatacgc agttctatat   720
agcacataat cttgcttgta tgtatgaaat ttaccgcgtt ttagttgaaa ttgtttatgt   780
tgtgtgcctt gcatgaaatc tctcgttagc cctatcctta catttaactg gtctcaaaac   840
ctctaccaat tccattgctg tacaacaata tgaggcggca ttactgtagg gttggaaaaa   900
aattgtcatt ccagctagag atcacacgac ttcatcacgc ttattgctcc tcattgctaa   960
atcatttact cttgacttcg acccagaaaa gttcgcccgc tcgtccaacg ccggcggacc  1020
tatagttgtt ttttctatat aaaacgaaac gttatcatct ttaataatca ttgaggttta  1080
cccttatagt tccgtatttt cgtttccaaa cttagtaatc ttttggaaat atcatcaaag  1140
ctggtgccaa tcttcttgtt tgaagtttca aactgctcca ccaagctact tagagactgt  1200
tctaggtctg aagcaacttc gaacacagag acagctgccg ccgattgttc tttttttgtgt  1260
ttttcttctg gaagaggggc atcatcttgt atgtccaatg cccgtatcct ttctgagttg  1320
tccgacacat tgtccttcga agagtttcct gacattgggc ttcttctatc cgtgtattaa  1380
ttttgggtta agttcctcgt ttgcatagca gtggatacct cgatttttt ggctcctatt   1440
tacctgacat aatattctac tataatccaa cttggacgcg tcatctatga taactaggct  1500
ctcctttgtt caaggggac gtcttcataa tccactggca cgaagtaagt ctgcaacgag   1560
gcggcttttg caacagaacg atagtgtcgt ttcgtacttg gactatgcta aacaaaagga  1620
tctgtcaaac atttcaaccg tgtttcaagg cactctttac gaattatcga ccaagacctt  1680
cctagacgaa catttcaaca tatccaggct actgcttcaa ggtggtgcaa atgataaagg  1740
tatagatatt agatgtgttt gggacctaaa acagttcttg cctgaagatt cccttgagca  1800
acaggcttca atagccaagt tagagaagca gtaccaaatc ggtaacaaaa gggggaagca  1860
tataaaacct ttactattgc gacaaaatcc atccttgaaa gtaaagctgt ttgcggtgtt  1920
taaaccccag cgcctggcgg g                                             1941
```

<210> SEQ ID NO 59
<211> LENGTH: 1940
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 59

| | | | | | |
|---|---|---|---|---|---|
| gacggcacgg | ccacgcgttt | aaaccgcctg | ttcaattgaa | ctggtgtttg | aacaacgcct | 60 |
| acatcaataa | taccaatcat | cggacgaaaa | atatggaatt | aatactaaaa | tatcttatcc | 120 |
| cctccagtct | tatagttggt | aagataccaa | atttgaacat | cctgaaccag | ctgctgtcat | 180 |
| ctcaagaggc | acaccctctg | attgagcttt | atcgaccact | gatttcaacc | ctcaaaaagg | 240 |
| gtaatgtttt | cgaattccac | aaatacctgt | ttgataatga | gtcatacttt | ttaaagatga | 300 |
| acgttctcct | gccgctactt | caacggttgc | gtattttgct | gttcagaaat | ctggtccgaa | 360 |
| agctggccct | tatagagcca | ccagtcaaca | actctctgag | attttcatcc | atcaaaacag | 420 |
| cccttttcgt | ttccatttca | cccaatcaaa | acgcatactt | tcagaacaat | tattcatacc | 480 |
| tgattgttac | caacgagtcc | cagatagacg | actcctttgt | ggagaacctc | atgatcagtc | 540 |
| taatcgatca | aaacctaatt | aagggtaaac | tcgtcaacga | taaccaccga | ataattgtct | 600 |
| ccaaggccga | tacattcccg | gagatcccta | cgatttattc | gactaagttt | gccgtagact | 660 |
| cgtcattcga | ttggctggac | caatagacgt | ccttttttt | tttttatcg | tgtctgccgt | 720 |
| ttaatgtcac | gcctcatgtt | tcaagttacg | ataacttatc | atgcagatac | taaatagtca | 780 |
| catgacgaat | gacgattttt | tgcgggttgc | tcagaggaat | atgcctctga | taagcgaggt | 840 |
| aaatgtcgag | cataagccac | ttactgtata | aatacccctt | tatcgccact | ttatctttc | 900 |
| tccttgtccg | ttatctacaa | caccccagta | aaacattaca | aacactctag | tgttgtttta | 960 |
| ctgtcccttt | taactctctt | caaacaaatc | tccatattat | ttaaactcgc | tcgtccaacg | 1020 |
| ccggcggacc | tattggagaa | aaggaataca | caaggagtta | aaaaaagtgt | ggtagaaagt | 1080 |
| gcatttgtca | taattttcca | tatgttgctg | tcactgtaat | cttttatatt | ttgttttgtt | 1140 |
| ttatgtagta | tttcaaaagg | ttcttatcat | cttactggca | taaacttgat | gtacgcagag | 1200 |
| atagcaaccg | ttgcttaggt | aagcatagta | aaaatggctg | gttttctgtc | ttattttaag | 1260 |
| gccactgttg | ggacaaaaca | caataactag | attttatcgg | attgaacagt | gtaaaggctt | 1320 |
| cactggctta | tatcttgtat | gagtacgata | cattatccag | ttccatcaag | gcctgtggaa | 1380 |
| atattacagc | caggacatga | acctgaaagg | gagtttagtg | ggatcactgt | agataatagg | 1440 |
| aacagactta | atgaagaaaa | gtattatcag | acgaaaatag | acgaagcgtt | gaaaaggggc | 1500 |
| acagaaagac | gttacgttga | tgatcatagc | agaggtcatg | agtctccaag | ttcagatttg | 1560 |
| gaggacactc | cggatcaatt | cttggaattt | cacattcatg | ataacggaga | taggaagatt | 1620 |
| tcaaggccag | acactgcttc | gtcattgatt | agtgaaaacg | acatggacta | cgatgatttg | 1680 |
| tttgttgaca | gaaagcaacc | aaaacatgct | acttctcatg | taaagcagtt | tattaggaag | 1740 |
| aatgtgttcc | aaaagaagac | tcatctacca | aacattgggg | ctagagaact | ggaattacag | 1800 |
| aaacggcttg | ctttattaga | gggcccaata | gatgacgatg | agattattag | tgctatgccc | 1860 |
| atggtagcgt | gtccctctga | ctataacgat | caacctgctg | attcaaattc | aacggtgttt | 1920 |
| aaacccagc | gcctggcggg | | | | | 1940 |

<210> SEQ ID NO 60
<211> LENGTH: 2004
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 60

```
gacggcacgg ccacgcgttt aaaccgccag atctaacatc caaagacgaa aggttgaatg      60
aaacctttt  gccatccgac atccacaggt ccattctcac acataagtgc caaacgcaac     120
aggaggggat acactagcag cagaccgttg caaacgcagg acctccactc ctcttctcct     180
caacacccac ttttgccatc gaaaaaccag cccagttatt gggcttgatt ggagctcgct     240
cattccaatt ccttctatta ggctactaac accatgactt tattagcctg tctatcctgg     300
cccccctggc gaggttcatg tttgtttatt tccgaatgca acaagctccg cattacaccc     360
gaacatcact ccagatgagg gctttctgag tgtggggtca aatagtttca tgttccccaa     420
atggcccaaa actgacagtc tcaacgctgt cttggaacct aatatgacaa agcgtgatc      480
tcatccaaga tgaactaagt ttggttcgtt gaaatgctaa cggccagttg gtcaaaaaga     540
aacttccaaa agtcggcata ccgtttgtct tgtttggtat tgattgacga atgctcaaaa     600
ataatctcat taatgcttag cgcagtctct ctatcgcttc tgaaccccgg tgcacctgtg     660
ccgaaacgca aatggggaaa cacccgcttt ttggatgatt atgcattgtc tccacattgt     720
atgcttccaa gattctggtg ggaatactgc tgatagccta acgttcatga tcaaaattta     780
actgttctaa cccctacttg acagcaatat ataaacagaa ggaagctgcc ctgtcttaaa     840
cctttttttt atcatcatta ttagcttact ttcataattg cgactggttc caattgacaa     900
gcttttgatt ttaacgactt ttaacgacaa cttgagaaga tcaaaaaaca actaattatt     960
cgaaacgcgc tcgtccaacg ccggcggacc ttcaaggaga tgtcagaatg ccatttgcct    1020
gagagatgca ggcttcattt ttgatacttt tttatttgta acctatatag tataggattt    1080
ttttgtcat  tttgtttctt ctcgtacgag cttgctcctg atcagcctat ctcgcagctg    1140
atgaatatct tgtggtaggg gtttgggaaa atcattcgag tttgatgttt ttcttggtat    1200
ttcccactcc tcttcagagt acagaagatt aagtgagacg ttcgtttgtg caagcttcaa    1260
cgatgccaaa agggtataat aagcgtcatt gcagcattg  tgaagaaaac tatgtggcaa    1320
gccaagcctg cgaagaatgt attttaagtt tgactttgat gtattcactt gattaagcca    1380
taattctcga gtatctatga ttggaagtat gggaatggtg atacccgcat tcttcagtgt    1440
cttgaggtct cctatcagat tatgcccaac taaagcaacc ggaggaggag atttcatggt    1500
aaatttctct gacttttggt catcagtaga ctcgaactgt gagactatct cggttatgac    1560
agcagaaatg tccttcttgg agacagtaaa tgaagtccca ccaataaaga aatccttgtt    1620
atcaggaaca aacttcttgt ttcgaacttt ttcggtgcct tgaactataa aatgtagagt    1680
ggatatgtcg ggtaggaatg gagcgggcaa atgcttacct tctggacctt caagaggtat    1740
gtagggtttg tagatactga tgccaacttc agtgacaacg ttgctatttc gttcaaacca    1800
ttccgaatcc agagaaatca aagttgtttg tctactattg atccaagcca gtgcggtctt    1860
gaaactgaca atagtgtgct cgtgttttga ggtcatcttt gtatgaataa atctagtctt    1920
tgatctaaat aatcttgacg agccagacga taataccaat ctaaactctt taaacgcggt    1980
gtttaaaccc cagcgcctgg cggg                                           2004
```

<210> SEQ ID NO 61
<211> LENGTH: 2084
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 61

```
gacggcacgg ccacgcgttt aaaccgccct ccaccgtctt gatactttct gaggtgcaca      60
gaccagagga ttgtgcgaac cctaaatagt tgtatgaact caaattcaag cgctctgtga     120
cggtgccgga ataattatag gtattgttgt aatcgtcact ggttctgtcg taacatttga     180
tgtacctacc gggaactcca catatgggcc ttgcaaaaca gtcatctaat cttgttttca     240
aacgacgcgt gtagaaactt tcaaaattgg cataccatgg agcaatacca tctttcacca     300
tcacatctct gaatagttca gggtgaaaca acttcccaaa gaagtctcta atatggccta     360
ttatgatcaa aataaggtaa ttaaggtatg ttgcaatcag gatgaaatat ggaggttcgt     420
cctcgatggg aactggaagc ggctcgccag ggttatgctt agagacaaag agccattctt     480
tactggtcaa ggacccaaat tctttctcgg ccttctcttg tggtgaatca ttgtctatga     540
gagcatctgg gatagttttt gacatgatct ttttcagcac ggctatatag caaaaagcaa     600
aaaaaaagac cgaatggaat tatatggtct aaaaaaacaa actggtggta aaataaaaaa     660
aaaacgactg gtgggcggtt tcaaaggaga ctaatgatct tctatgcccg cggaaataaa     720
tagtactcca acgactgaac tcagcggtat taagtttgt gaataaaatt acaaggctta     780
gaaagcttgg ttggtctttc ggtatctgta gatggtagag ttttgagaac atttcatttc     840
cacagtaacc aacgaacacg acccgtgact tccgggggtt ggcagatgtt aacgcgcgcg     900
tggtagaagt ttatcttggg aggtgctaga gggtgctctt ggccttgttc gctgggggga     960
agtgtttgta gttaacgtac aactcctcat gactggggat cagaatttca acttgatttg    1020
ccgctaatcg ctcgtccaac gccggcggac cttaaaaata atgatttaca tttaagaagt    1080
aacagcacat atatactgta agattaactt tgcgtaccct aaattttact aataaactta    1140
acgggttgcc atagccttgg taaccacacg tttcaatgcc aattcagctt ttctgaagtc    1200
atcaccggaa gcatcttcta gctccaaagc agccaaagcg tcagacaaag cagactcgat    1260
cttgtcctta gcacttctct ttagcttgga agacaaaatt gggtcagtga tggtagactc    1320
aatggaggaa acgtaagcct ccaacttctg tttggattcg tgacggttag cgaagtcctc    1380
gtcagccttc ttgaacttgt cagcatcgtt gatcatcttt tcgatctcgg aagaagacaa    1440
tctaccaata gagttagaaa tagtgatgtt ggcagatctt ccggtagact ctcgacagc    1500
ggtaaccttc aagataccgt tggcatcaat ctcaaagata gcctccaaca ctggctcacc    1560
agcagacata ggaggaatgt tcttcaagtc gaactcaccc aacaaggtgt tctcagaaca    1620
gttgacacgc tcaccctggt aaactgggaa ttgaacagtg gtttggtggt cgtcaacagt    1680
ggtgaaagtt cttctcttga tagttgggac agtggtgttt cttggaacaa ctggggcaaa    1740
gacgttacct tgcatggcaa cacccaaaga aagaggata acatccaaca acaacaagtc    1800
cttggtctct tcagaggtag attgaccggt caaaatagca ccttgaacgg cggcaccgta    1860
agcgacagcc tcatcagggt tgatggattt ctccaattgc ttaccatcga agaagtcaga    1920
caacagcttt tggaccttg gaattctggt ggaaccacca accaagacga cgtcatcgac    1980
cttggatttc tcgatctttg agtccttcaa aacttgttca acaggctcca agtagactt    2040
gaacaaatca gcgttgcggt gtttaaaccc cagcgcctgg cggg                     2084
```

<210> SEQ ID NO 62
<211> LENGTH: 1937

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
gacggcacgg ccacgcgttt aaaccgcccg tatctaatct ttctcgctcc ccgtacgtta      60
agaatgaaat ttctacttcc attatagaaa atagtgtatc actgccagca tcttttactc     120
acaagcaatt aaacaaagta acaatggtct ctaagcaatt ggaatcacca caggggacct     180
ttatcacgtt gaatctagtt gaaaattcag tgtccaagtt cggtgcagta cataccac      240
aaggaaaaac cccatttgtt gttggtagag attcatcttg tgactggttg atcaaagaag     300
aaagaatttc caaaatacac tgcatgattg ccaaaaaaag gcatcctact gctaatcctt     360
ccatatttga gtcacctgct ttagggctgg aagatatttg gttactagat tttagtacaa     420
actcttgctt tgtcaatgac attaaaatag gcaagaatcg caaaactcaa atatttcatg     480
gagatgagat atgcttgttc aaagatgccc agaaaaaaga gcaactcgtt tatagggttc     540
atattgatga tggaacaggc cttttccagg gaggtgaaag aacccaagcc aattctgatg     600
acattctgga tattgatgag gttgatgaaa agttaagaga actattgaca agagcctcaa     660
ggaaacggca tatcaccccct gcattggaaa ctcctgataa acgtgtaaaa agagcttatt     720
tgaacagtat tactgataac tcttgatgga ccttaaagat gtataatagt agacagaatt     780
cataatggtg agattaggta atcgtccgga ataggaatag tggtttgggg cgattaatcg     840
cacctgcctt atatggtaag taccttgacc gataaggtgg caactattta gaacaaagca     900
agccaccttt ctttatctgt aactctgtcg aagcaagcat ctttactaga gaacatctaa     960
accatttac  attctagagt tccatttctc aattactgat aatcaattta aagcgctcgt    1020
ccaacgccgg cggacctgca agaataaaag ttgctcagct gaacttattt ggttacttat    1080
caggtagtga agatgtagag aatatatgtt taggtatttt tttttagttt ttctcctata    1140
actcatcttc agtacgtgat tgcttgtcag ctaccttgac aggggcgcat aagtgatatc    1200
gtgtactgct caatcaagat ttgcctgctc cattgataag ggtataagag acccacctgc    1260
tcctctttaa aattctctct taactgttgt gaaaatcatc ttcgaagcaa attcgagttt    1320
aaatctatgc ggttggtaac taaaggtatg tcatggtggt atatagtttt tcattttacc    1380
ttttactaat cagttttaca gaagaggaac gtctttctca agatcgaaat aggactaaat    1440
actggagacg atggggtcct tatttgggtg aaaggcagtg ggctacagta agggaagact    1500
attccgatga tggagatgct tggtctgctt ttccttttga gcaatctcat ttgagaactt    1560
atcgctgggg agaggatgga ctagctggag tctcagacaa tcatcaacta atttgtttct    1620
caatggcact gtggaatgag aatgatgata ttttgaagga gcgattattt ggggtcactg    1680
gagaggctgc aaatcatgga gaggatgtta aggagcttta ttattatctt gataatacac    1740
cttctcactc ttatatgaaa tacctttaca aatatccaca atcgaaattt ccttacgaag    1800
aattgatttc agagaaccgt aaacgttcca gattagaaag agagtacgag attactgact    1860
ctgaagtact gaaggataac agatattttg atgtgatctt tgaaatggcc ggtgtttaaa    1920
ccccagcgcc tggcggg                                                   1937
```

<210> SEQ ID NO 63
<211> LENGTH: 7013
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
gacggcacgg ccacgcgttt aaaccgcccg tatctaatct ttctcgctcc ccgtacgtta      60
agaatgaaat ttctacttcc attatagaaa atagtgtatc actgccagca tcttttactc     120
acaagcaatt aaacaaagta acaatggtct ctaagcaatt ggaatcacca caggggacct     180
ttatcacgtt gaatctagtt gaaaattcag tgtccaagtt cggtgcagta cacataccac     240
aaggaaaaac cccatttgtt gttggtagag attcatcttg tgactggttg atcaaagaag     300
aaagaatttc caaaatacac tgcatgattg ccaaaaaaag gcatcctact gctaatcctt     360
ccatatttga gtcacctgct ttagggctgg aagatatttg gttactagat tttagtacaa     420
actcttgctt tgtcaatgac attaaaatag gcaagaatcg caaaactcaa atatttcatg     480
gagatgagat atgcttgttc aaagatgccc agaaaaaaga gcaactcgtt tatagggttc     540
atattgatga tggaacaggc cttttccagg gaggtgaaag aacccaagcc aattctgatg     600
acattctgga tattgatgag gttgatgaaa agttaagaga actattgaca agagcctcaa     660
ggaaacggca tatcaccccct gcattggaaa ctcctgataa acgtgtaaaa agagcttatt     720
tgaacagtat tactgataac tcttgatgga ccttaaagat gtataatagt agacagaatt     780
cataatggtg agattaggta atcgtccgga ataggaatag tggtttgggg cgattaatcg     840
cacctgcctt atatggtaag taccttgacc gataaggtgg caactattta gaacaaagca     900
agccaccttt ctttatctgt aactctgtcg aagcaagcat ctttactaga gaacatctaa     960
accattttac attctagagt tccatttctc aattactgat aatcaattta aagcgctcgt    1020
ccaacgccgg cggacctaac aggagggggat acactagcag cagaccgttg caaacgcagg    1080
acctccactc ctcttctcct caacacccac ttttgccatc gaaaaaccag cccagttatt    1140
gggcttgatt ggagctcgct cattccaatt ccttctatta ggctactaac accatgactt    1200
tattagcctg tctatcctgg ccccccctggc gaggttcatg tttgtttatt tccgaatgca    1260
acaagctccg cattacaccc gaacatcact ccagatgagg gctttctgag tgtgggtca    1320
aatagtttca tgttccccaa atggcccaaa actgacagtt taaacgctgt cttggaacct    1380
aatatgacaa aagcgtgatc tcatccaaga tgaactaagt ttggttcgtt gaaatgctaa    1440
cggccagttg gtcaaaaaga aacttccaaa agtcggcata ccgtttgtct tgtttggtat    1500
tgattgacga atgctcaaaa ataatctcat taatgcttag cgcagtctct ctatcgcttc    1560
tgaaccccgg tgcacctgtg ccgaaacgca aatggggaaa cacccgcttt ttggatgatt    1620
atgcattgtc tccacattgt atgcttccaa gattctggtg ggaatactgc tgatagccta    1680
acgttcatga tcaaaattta actgttctaa cccctacttg acagcaatat ataaacagaa    1740
ggaagctgcc ctgtcttaaa cctttttttt atcatcatta ttagcttact ttcataattg    1800
cgactggttc caattgacaa gcttttgatt ttaacgactt taacgacaa cttgagaaga    1860
tcaaaaaaca actaattatt cgaaacgatg agattcccat ccatcttcac tgctgttttg    1920
ttcgctgctt cttctgcttt ggctgaggtt cagttggttg aatctggagg aggattggtt    1980
caacctggtg gttctttgag attgtcctgt gctgcttccg gtttcaacat caaggacact    2040
tacatccact gggttagaca agctccagga aagggattgg agtgggttgc tagaatctac    2100
ccaactaacg gttacacaag atacgctgac tccgttaagg gaagattcac tatctctgct    2160
```

```
gacacttcca agaacactgc ttacttgcag atgaactcct tgagagctga ggatactgct    2220
gtttactact gttccagatg gggtggtgat ggtttctacg ctatggacta ctggggtcaa    2280
ggaactttgg ttactgtttc ctccgcttct actaagggac catctgtttt cccattggct    2340
ccatcttcta agtctacttc cggtggtact gctgctttgg gatgtttggt taaagactac    2400
ttcccagagc cagttactgt ttcttggaac tccggtgctt tgacttctgg tgttcacact    2460
ttcccagctg ttttgcaatc ttccggtttg tactctttgt cctccgttgt tactgttcca    2520
tcctcttcct tgggtactca gacttacatc tgtaacgtta accacaagcc atccaacact    2580
aaggttgaca agaaggttga gccaaagtcc tgtgacaaga ctcatacttg tccaccatgt    2640
ccagctccag aattgttggg tggtccttcc gttttttttgt tcccaccaaa gccaaaggac    2700
actttgatga tctccagaac tccagaggtt acatgtgttg ttgttgacgt ttctcacgag    2760
gacccagagg ttaagttcaa ctggtacgtt gacggtgttg aagttcacaa cgctaagact    2820
aagccaagag aggagcagta caactccact tacagagttt tttccgtttt gactgttttg    2880
caccaggatt ggttgaacgg aaaggagtac aagtgtaagg tttccaacaa ggctttgcca    2940
gctccaatcg aaaagactat ctccaaggct aagggtcaac caagagagcc acaggtttac    3000
actttgccac catccagaga tgagttgact aagaaccagg tttccttgac ttgtttggtt    3060
aagggattct acccatccga cattgctgtt gaatgggagt ctaacggtca accagagaac    3120
aactacaaga ctactccacc tgttttggac tctgacggtt ccttttttctt gtactccaag    3180 ttgactgttg acaagtccag atggcaacag ggtaacgttt ctcctgttc cgttatgcat    3240 gaggctttgc acaaccacta cactcaaaag tccttgtctt tgtcccctgg taagtagacg    3300
cacgcacact cccgcagaca aactagcttg ataacaggcc ccttttcctt tgtcgatatc    3360
atgtaattag ttatgtcacg cttacattca cgccctcccc ccacatccgc tctaaccgaa    3420
aaggaaggag ttagacaacc tgaagtctag gtccctattt attttttttat agttatgtta    3480 gtattaagaa cgttatttat atttcaaatt tttctttttt ttctgtacaa acgcgtgtac    3540 gcaatcccg cgtgcttggc cggccgtaag attattactt gctataagtg cgtgcctgat    3600
gaacaggata ttgcggtcaa taatgctgat ggttcattag acttcagcaa agccgatgcc    3660
aaaataagcc aatacgatct caacgctatt gaagcggctt gccagctaaa gcaacaggca    3720
gcagaggcgc aggtgacagc cttaagtgtg gcggtaaag ccctgaccaa cgccaaaggg    3780
cgtaaagatg tgctatcgcg cggcccggat gaactgattg tggtgattga tgaccagttc    3840
gagcaggcac tgccgcaaca aacggcgagc gcactggctg cagccgccca gaaagcaggc    3900
tttgatctga tcctctgtgg cgatggttct tccgaccttt atgcccagca ggttggtctg    3960
ctggtgggcg aaatcctcaa tattccggca gttaacggcg tcagcaaaat tatctccctg    4020
acggcagata ccctcaccgt tgagcgcgaa ctggaagatg aaaccgaaac cttaagcatt    4080
ccgctgcctg cggttgttgc tgtttccact gatatcaact ccccacaaat tccttcgatg    4140
aaagccattc tcggcgcggc gaaaaagccc gtccaggtat ggtcggcggc ggatattggt    4200
tttaacgcag aggcagcctg gtcagaacaa caggttgccg cgccgaaaca gcgcgaacgt    4260
cagcgcaacg gccggccaag cacgcgggga ttgcgtacac gcgttgtac agaaaaaaaa    4320 gaaaaatttg aaatataaat aacgttctta atactaacat aactataaaa aaataaatag    4380
ggacctagac ttcaggttgt ctaactcctt ccttttcggt tagagcggat gtgggggag    4440 ggcgtgaatg taagcgtgac ataactaatt acatgatatc gacaaaggaa aaggggcctg    4500
```

```
ttatcaagct agttgtctgt cgggagtgtg cgtgcgtcta acactctcct ctgttgaagg    4560
acttagtaac tggggaggac aaaccctgat gtgtaacctc acaagcgtaa accttgtgct    4620
tctcgtaatc agccttggac aaagtcaaag tggaggacaa ggagtaagtg gagtccttag    4680
agtcttgctc agtaacggat tcttgggagt taccggattg caaagcgttg tcaaccttcc    4740
actgaacctt agcctctctt gggtagaagt tgttcaacaa acaaacaacg gaagctgtac    4800
cagacttcaa ctgttcgtcg gatggtggga aaatgaaaac ggatggagca gcaacagttc    4860
tcttgatctc aaccttagta ccctgtccga agttggtgg agtagtgtag tgctgctgac     4920
agtagtaagt agcgaaatct tctggttgca aggaggagat agtcaaagtg aagtcagtac    4980
cggatctgga accagagaat ctggatggaa caccagagta caagaaggaa gcggagtaga    5040
tcaacaactt tggagccttt cctggcttct gttgatacca agcaacagca gtattaacgt    5100
cctgggaagc tctacaagtg atagtaactc tgtcaccaac ggaagcagac aaagaagatg    5160
gggattgagt catttggatg tcagccaaag cagaagaagc agcgaacaaa acagcagtga    5220
agatggatgg gaatctcatc gtttcgaata attagttgtt ttttgatctt ctcaagttgt    5280
cgttaaaagt cgttaaaatc aaaagcttgt caattggaac cagtcgcaat tatgaaagta    5340
agctaataat gatgataaaa aaaggttta agacagggca gcttccttct gtttatatat      5400
tgctgtcaag taggggttag aacagttaaa ttttgatcat gaacgttagg ctatcagcag    5460
tattcccacc agaatcttgg aagcatacaa tgtggagaca atgcataatc atccaaaaag    5520
cgggtgtttc cccatttgcg tttcggcaca ggtgcaccgg ggttcagaag cgatagagag    5580
actgcgctaa gcattaatga gattattttt gagcattcgt caatcaatac caaacaagac    5640
aaacggtatg ccgacttttg gaagtttctt tttgaccaac tggccgttag catttcaacg    5700
aaccaaactt agttcatctt ggatgagatc acgcttttgt catattaggt tccaagacag    5760
cgtttaaact gtcagttttg ggccatttgg ggaacatgaa actatttgac cccacactca    5820
gaaagccctc atctggagtg atgttcgggt gtaatgcgga gcttgttgca ttcggaaata    5880
aacaaacatg aacctcgcca ggggggccag gatagacagg ctaataaagt catggtgtta    5940
gtagcctaat agaaggaatt ggaatgagcg agctccaatc aagcccaata actgggctgg    6000
tttttcgatg gcaaaagtgg gtgttgagga aagaggagt ggaggtcctg cgtttgcaac     6060
ggtctgctgc tagtgtatcc cctcctgtta ggtccgccgg cgttggacga gcggcaagaa    6120
taaaagttgc tcagctgaac ttatttggtt acttatcagg tagtgaagat gtagagaata    6180
tatgtttagg tatttttttt tagttttttct cctataactc atcttcagta cgtgattgct    6240
tgtcagctac cttgacaggg gcgcataagt gatatcgtgt actgctcaat caagatttgc    6300
ctgctccatt gataagggta taagagaccc acctgctcct cttaaaatt ctctcttaac     6360 tgttgtgaaa atcatcttcg aagcaaattc gagtttaaat ctatgcggtt ggtaactaaa    6420
ggtatgtcat ggtggtatat agtttttcat tttaccttt actaatcagt ttacagaag      6480 aggaacgtct ttctcaagat cgaaatagga ctaaatactg gagacgatgg ggtccttatt    6540
tgggtgaaag gcagtgggct acagtaaggg aagactattc cgatgatgga gatgcttggt    6600
ctgcttttcc ttttgagcaa tctcatttga gaacttatcg ctggggagag gatggactag    6660
ctggagtctc agacaatcat caactaattt gtttctcaat ggcactgtgg aatgagaatg    6720
atgatatttt gaaggagcga ttatttgggg tcactggaga ggctgcaaat catggagagg    6780
atgttaagga gctttattat tatccttgata atacaccttc tcactcttat atgaaatacc    6840
tttacaaata tccacaatcg aaatttcctt acgaagaatt gatttcagag aaccgtaaac    6900
```

```
gttccagatt agaaagagag tacgagatta ctgactctga agtactgaag gataacagat      6960
attttgatgt gatctttgaa atggcggcgg tttaaacgcg tggccgtgcc gtc             7013
```

<210> SEQ ID NO 64
<211> LENGTH: 2448
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64

```
gacggcacgg ccacgcgttt aaaccgccac cgtcaatatg aagaataaca ctaaccagta        60
ttttgaaaag aagaaagcca ttaatgaaat cgtcaaatca attcattcca atttggaagc       120
ttctttattt agttcactaa aacgctcaga tatggcatct caaactctcc cctatgttta       180
tcatatcata ctgcctaact tcaaaaacat ggccagatta atcagcctga acctgaaga        240 aaagatcaaa cttacggaag ctgcaaaagt tcttaaagag tttggcttca cgattgagca       300
agcaaaagat gaaactttca cttacattca aaaactagtt ccgccaattg ataccgtagt       360
caattgtcag aacgaattat cgcatcaaaa gtcactttgc gcacgagcta atcagattct       420
cccatacatt gagattgagt tgaaaaggtt gaacatcacc aagagacacc taaccgattc       480
tgagcaagac ttcaagaaac tacaaggtac ttcaaagaga agaatcacag ggttgacctc       540
ccctagtaat cgacagtcgc gtgccgcatc tcttcaggag gggggcaga ctcaaaatca        600 gctgggtacc tctatagatt ttttcgccaa atcgctttcc cgagatggaa gctcaggcag       660
aacgacacct gcacctcaga cgaactctca gagaggcacc accggacgta tttgggtccg       720
ttataacgaa gggttctcaa atgcagttcg tagaaacatc acatgggaag agctgtggaa       780
tttttaaatg tcctccataa tttcatgcgg accttgcata gtttatataa tcatactgta       840
ccaaccaaca tccacacaag gagttttcgg cctcaacata ttatcgaaac catctccctg       900
tcccttactc agatcctatt ttttcttact caattgaacg ctcgtccaac gccggcggac       960
ctccttaact acgttaggtc agtgatgaca atggaccaaa ttgttgcaag gttttcttt      1020 ttctttcatc ggcacatttc agcctcacat gcgactatta tcgatcaatg aaatccatca      1080
agattgaaat cttaaaattg ccccttcac ttgacaggat cctttttgt agaaatgtct        1140 tggtgtcctc gtccaatcag gtagccatct ctgaaatatc tggctccgtt gcaactccga      1200
acgacctgct ggcaacgtaa aattctccgg ggtaaaactt aaatgtggag taatggaacc      1260
agaaacgtct cttcccttct ctctccttcc accgcccgtt accgtccta ggaaatttta       1320 ctctgctgga gagcttcttc tacgccccc ttgcagcaat gctcttccca gcattacgtt       1380
gcgggtaaaa cggaggtcgt gtacccgacc tagcagccca gggatggaaa agtcccggcc      1440
gtcgctggca ataatagcgg gcggacgcat gtcatgagat tattgaaaac caccagaatc      1500
gaatataaaa ggcgaacacc tttcccaatt ttggtttctc ctgacccaaa gactttaaat      1560
ttaatttatt tgtccctatt tcaataccte ccgcgacctc caaaatcgaa ctaccttcac      1620
aatgaggaca ttgacattgt tggtctactt cgtagtggct gccttagctt tcaccccgca      1680
gaccaactcc agaattttta aaggttaccc aaagaaagtg gtttattttg acgacactgc      1740
cagcgttgtc taccatgatg gctctgacaa tgagatctat tattccaaag atgatggtgt      1800
cacttggact caactagatc ttggtggggc gtccgctcat caagtaattg ttcaccctt       1860
```

```
tgacccttct actgcctata ttttgaccac tagtgaaact cacttcgtca ccacagatag      1920
cggatttact tggaataagg tttcctctcc agagcctcca gtaaccaacg agtttccaac      1980
gttgagccaa gagtcctcct cattgaccct gaattccaag aactttgagt atgttctgtt      2040
tgcaggccaa tgtacagacg gatcagaaat ttgcaacaga aagtactact attccttgga      2100
taacatgaga actttcaacg agctcattga agctcacagc tgtttgtttg tcgatactgc      2160
cgatgccatt gcgggtgatc attccccaaa cgctgttatc tgtgccatca ccaaccctga      2220
cggaaaactg tctttggtga aaaccgccaa cttcttcaaa gacggcatag actatgtctc      2280
tagtggtggt ggtcttattg agaatcctga actgctgggc gcctcacaca actacatctt      2340
ggctgttggt tctcatcttt tgcacaacaa agacaagttt gtatacatct catttgatgg      2400
ttcgaacttc aacaaagtga cggtgtttaa accccagcgc ctggcggg                  2448

<210> SEQ ID NO 65
<211> LENGTH: 2744
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
gacggcacgg ccacgcgttt aaaccgcctc tctgctcttc aagaagtaaa acgctgggcg        60
gcaaagaagg aaaagtccaa taaaagtatc tgtaagaggt ggaagtgctc agatagtgcg       120
aagagaggaa taaatgaatg caagagcgcg atggagtgta gcgtgattac atcatcagat       180
gctacattga ttctctgata tgaatggtga tggaactttc tagaggttcc ttgaagaaat       240
aaatacattt acaagcagaa ctccactttt tcacggagaa tcatctaagt taggcatacg       300
aaggatctcg ccttcgttgt ttgcactcat ctcctgtagt ttagcgagaa tcttggagtc       360
cttccacttt tcaggcaatg gggtaacctc gtagttttc acggcccagt aataaatatc       420
ccaatccaac tcgtttaata agtcatcata ctcttccatc tcttccacac tcattgtcgg       480
tagatagcgt tttgcgaaac gagacagaag aaggtctgtt tccaagattc ctctctttct       540
tgactgataa accagacggc gtctcttgac atcttccgac tcgttatcac gtttcagagg       600
ttcaactttc agtatcagct cctgcctcaa gaaggggaga gaatgaaaag atttcgaaaa       660
cacccttgga caagtcttgc taccttgaaa ctgagttctt tggaaaagcc ggagcataat       720
gggtgaatta agcagaaaga aggtaactga tttgctgaga cccaaatcat ctacagtttc       780
gcgaagcata aagttcacac tgattttctg gggaagaact ggtaaaccac atgttgtctc       840
cattccacga taaaccgttc aagcaaggcc gtcttagaat gcacaagaca atttaggtaa       900
actacctttc ctggaagcga aagcagacgt tacaatctgt ttcatccccc aactgcactc       960
ctctctcctc tgctagccaa gacgatcttt catagaattt gatggaattt acgcgaaatc      1020
gccacgtaat catatttcga acagcgctcg tccaacgccg gcggacctcc ttaactacgt      1080
taggtcagtg atgacaatgg accaaattgt tgcaaggttt ttctttttct ttcatcggca      1140
catttcagcc tcacatgcga ctattatcga tcaatgaaat ccatcaagat tgaaatctta      1200
aaattgcccc tttcacttga caggatcctt ttttgtagaa atgtcttggt gtcctcgtcc      1260
aatcaggtag ccatctctga aatatctggc tccgttgcaa ctccgaacga cctgctggca      1320
acgtaaaatt ctccggggta aaacttaaat gtggagtaat ggaaccagaa acgtctcttc      1380
ccttctctct ccttccaccg cccgttaccg tccctaggaa attttactct gctggagagc      1440
```

```
ttcttctacg gccccttgc agcaatgctc ttcccagcat tacgttgcgg gtaaaacgga    1500
ggtcgtgtac ccgacctagc agcccaggga tggaaaagtc ccggccgtcg ctggcaataa    1560
tagcgggcgg acgcatgtca tgagattatt ggaaaccacc agaatcgaat ataaaaggcg    1620
aacacctttc ccaattttgg tttctcctga cccaaagact ttaaatttaa tttatttgtc    1680
cctatttcaa tacctcccgc gacctccaaa atcgaactac cttcacaatg aagatctcta    1740
ccattgcaag ttctacgttg ttcgctgttg gtgctttagc cgaatccgaa cccgctgagt    1800
tcagacccct ggaagctcag ttggacaagt catctttctt tgaacaattc gacaaggaac    1860
cgaaactcgg cgacacctgg aagatctccc atgccgttaa gatgaagaa ttcacttatg    1920 ttggagaatg ggccattgag gaacctgttg tctatcctgg attcaagaag gacaggggtc    1980
tggttgtgaa atctgaggca gctcaccacg caatatctgc ccaattacca caggtatttg    2040
acaacactga caatacgttg gtcttgcaat acgaagtcaa gcttcaacaa ggattgaact    2100
gtggaggtgc ttatgttaaa ttattgagtg ctgagggtct gaacaagaat gagttctcta    2160
acgagacccc ttatcaagtc atgtttggtc ctgataaatg tggaaccacg aataaagtgc    2220
acttgattat taagaggaag aacccagcca ccggcgaata tgaggaacat caattggcta    2280
ctcctccaat gggtagaatc gtcaagacta cttctctata caccctgatt atcaagccca    2340
ataatgactt tgaaatcaga atcaacggtg aggttgctaa agctggtaac ttgttgaacg    2400
agaagttgat aaagccacca tttggcgctc cgaaggagat tgacgatccg gaagaccaaa    2460
aacccgaaga ttgggttgat gaagacatga tcccagatcc agatgctgtc aagcctgaag    2520
attgggacga gtccgagcca ttgcgaatcg tcgatccgga agctgtgaaa ccagaaaact    2580
ggaacgaaga tgctgaattg tacatccctg atccagaggc caccaagccc gaagactggg    2640
acgatgaaga ggatggcgaa tgggttgctc ctgttattcc aaatccagaa tgcgcagata    2700
ttggatgtgg cccttgcggt gtttaaaccc cagcgcctgg cggg              2744
```

<210> SEQ ID NO 66
<211> LENGTH: 2585
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

```
gacggcacgg ccacgcgttt aaaccgccga ttgtcttcaa acatttacac tgagtgttgg      60
aaccattaag ttgccatatt tgagccgtcg aatctttggc gacggtgaca aatatcagtt     120
catcaactgt atcccaagca atgcaataga ctggcttgtt agaggttgta ttgatctgca     180
ataaagagtc ccatacattt tccttgaacc ttttccatat gcagagggtt ttatcagatc     240
ttgaatacgc caatctattt cccttgttga attctaaagt gatgatatca gtgctagttc     300
ggtgattttc taaagagcca tcattcaact ccgttgattt cagatcagta aaaagctgct     360
tgtccctagc tagtgaaggg ttggtcatta tagaggcctt caaacaatac ttttcaaaat     420
agacacgccg cgcgaatcct cacgatagcg aaataccaac tccacagatg ttaccacgta     480
acatttctcc tctgatcaaa tggctcctca acaccaagg caacgtatcg caaacgaaaa     540
attcgtaaag agagctgaag ctcagcaggg taaggtgaag aaggctagat ccaagcgtga     600
atttccagtt tcgactaagt gggttatcat attgctcttc ttgctgattg ggggagggt      660
```

```
cctggagatt tgagattgt tttttgaat gatctttca aaggtctagg tctttttgga    720
aggaaatggt tatactttgg cctttcatta tttgagagga tagtcgtatt tttctaccgg  780
gagaaggtag gcataacgtt aattgcgaat tttcacttac tttagatggg tactgatctt  840
caactcacga taatttcatt gcaccatgta tctctaaact ggcgtgtcgg aactcacaca  900
ccattggaac ttattgatta accaatacat agattaattg actcgcctga taatactaat  960
caccgttcac tacttctctt agtatcttct cctactggag tcgttctacg ctcgtccaac 1020
gccggcggac ctccttaact acgttaggtc agtgatgaca atggaccaaa ttgttgcaag 1080
gttttctttt ttctttcatc ggcacatttc agcctcacat gcgactatta tcgatcaatg 1140
aaatccatca agattgaaat cttaaaattg cccctttcac ttgacaggat cctttttttgt 1200
agaaatgtct tggtgtcctc gtccaatcag gtagccatct ctgaaatatc tggctccgtt 1260
gcaactccga acgacctgct ggcaacgtaa aattctccgg ggtaaaactt aaatgtggag 1320
taatggaacc agaaacgtct cttcccttct ctctccttcc accgcccgtt accgtcccta 1380
ggaaatttta ctctgctgga gagcttcttc tacggccccc ttgcagcaat gctcttccca 1440
gcattacgtt gcgggtaaaa cggaggtcgt gtacccgacc tagcagccca gggatggaaa 1500
agtcccggcc gtcgctggca ataatagcgg gcggacgcat gtcatgagat tattggaaac 1560
caccagaatc gaatataaaa ggcgaacacc tttcccaatt tggtttctc ctgacccaaa 1620
gactttaaat ttaatttatt tgtccctatt tcaataccct ccgcgacctc caaaatcgaa 1680
ctaccttcac aatgttgtca tcaagatggt gttcatgtaa aaagcagagt ccaagtcgac 1740
aagtaggtca gttactgcgc tacatgtcta gcaaggtaat tggaattgat ttaggaacta 1800
cgaactctgc tgttgccgtt tttgaaggaa agaaccaaa aatcctggag aacgaagagg 1860
gaaagagaac gacaccttct attgttgcat ttaccccaga aactgtgcta gtaggagaac 1920
cagcaaagag acaatctatt ctgaactatc agaacacttt ttatgctaca aaaaggctca 1980
ttggtcgcaa gtattcggat cctgaagttc aacgggatat ttccaacgtt ccttacagta 2040
taattgaaca tgaaaatggg gatgcgtggc ttcaaaacat gcactcaggt caaaaatact 2100
ccccctctca aattggtagt ttgatattgg gaaagatgaa agagattgca gagctaaatc 2160
tttcccagtc tattagccag gctgtggtca ctgtgcctgc ctacttcaac gattcgcaaa 2220
gacaagcaac taagattgct ggtgatttag tgggtcttaa agttttaaga gttatcaatg 2280
agcccaccgc tgcttctttg gcttacggat tgaatagaaa aaatgacggg ataattgccg 2340
tttacgacct tggtggtgga acttttgata tctccatatt ggatatcgaa gccggcgtct 2400
ttgaagttat tgcgacgaat ggtgacacac atcttggagg ggaagatttt gaccatttgc 2460
tggtggacta catattgcaa cagtttcaat cgcagacagg acaagatcta tctactgacc 2520
gtttggccct gcaaagaatt cgtcaggctg ctgaaaacgg tgtttaaacc ccagcgcctg 2580
gcggg                                                            2585
```

<210> SEQ ID NO 67
<211> LENGTH: 2740
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 67

```
gacggcacgg ccacgcgttt aaaccgccag aatcacaaaa ttctttcat cttcagacat     60
```

```
gtatatctgg ctcagagatt tgaagggaat ctgaaacctg gttttagacg gaaggtcaac      120
tatgaggtac aggctgttag gccatatgct taaaaaagga acaggtaagg atatgttttt      180
attgatgatg gagatgtggt gcaagtgaat cctgagaacc tcttttttct tttcaaacgc      240 attttttgtct tcaattccat tcttcgatct tttaacgatg ggagcgctta ttttgtctat     300
gatgtggctt tgaagatcag ctgttgtatt caaactatca ctttgagtca acgagttctt      360
aggtagtctt tgaaaccgtg aaagggaacc cattttcttc gaacccaggg atttcactga      420
tcctctggcc attgacgccg atcgtgagtt ctgtagagtt cccttcgtct aagagagag       480 ggggaataat taaagatcaa gtaatgttct acctacaaaa gataaagatg accttaatgt      540
ttttagcgag gtatagctgg gagtcccaaa gaagtagcta gggcggtgag aggattttt      600 tctcgtgcgc atataatcgc tagcctagtt aaagcatctt gacgacgtac taatatctgg     660
aagacttcag agcacagaaa ctatgcctgg tgagttcatg gtgaccgtat tgagcacatc     720
caaaaagatc ttattctctc cagtacaatc agcagaaggc cttatccatc ttgctgttcc     780
actacctcat tccagtatac ttctaatcat cgcctctaga taagccagac gatctcaaga    840 accacccctca tcttgaaacg tggactcgag tcgcaatgtc ctgtatcatt cctacgtcac     900
aagccatcac tgggttctct cgccccccta cgaaacgcta gctattgcta tatggaacaa     960
tctagaccgt aagttagggc cactctgttc atttctcgtc ttagtcagct gatcctcgaa    1020
acgatctacg ctcgtccaac gccggcggac ctccttaact acgttaggtc agtgatgaca    1080
atggaccaaa ttgttgcaag gttttctctt ttctttcatc ggcacatttc agcctcacat    1140
gcgactatta tcgatcaatg aaatccatca agattgaaat cttaaaattg ccccttcac    1200 ttgacaggat cctttttttgt agaaatgtct tggtgtcctc gtccaatcag gtagccatct    1260
ctgaaatatc tggctccgtt gcaactccga acgacctgct ggcaacgtaa aattctccgg    1320
ggtaaaactt aaatgtggag taatggaacc agaaacgtct cttcccttct ctctccttcc    1380
accgcccgtt accgtcccta ggaaatttta ctctgctgga gagcttcttc tacggccccc    1440
ttgcagcaat gctcttccca gcattacgtt gcgggtaaaa cggaggtcgt gtacccgacc    1500
tagcagccca gggatggaaa agtcccggcc gtcgctggca ataatagcgg gcggacgcat    1560
gtcatgagat tattggaaac caccagaatc gaatataaaa ggcgaacacc tttcccaatt    1620
ttggtttctc ctgacccaaa gactttaaat ttaatttatt tgtccctatt tcaataccttc   1680 ccgcgacctc caaaatcgaa ctaccttcac aatgaggata gtaaggagcg tagctatcgc    1740
aatagcctgt cattgtataa cagcgttagc aaaccctcaa atccctttg acggcaacta    1800 caccgagatc atcgtgccag ataccgaagt taacatcgga cagattgtag atattaacca    1860
cgaaataaaa cccaaactgg tggaactggt caacacagac ttcttcaaat attacaaatt    1920
aaacctatgg aaaccatgtc cgttttggaa tggtgatgag ggattctgca agtataagga    1980
ttgctctgtc gactttatca ctgattggtc tcaggtgcct gatatctggc aaccagacca    2040
attgggtaag cttggagata acacggtaca taaggataag ggccaagatg aaaatgagct    2100
gtcctcaaat gattattgcg ctttggataa agacgacgat gaagatttag tatatgtcaa    2160
tttgattgat aaccctgaaa gattcaccgg ttatggtggt cagcaatctg aatctatttg    2220
gactgcggtc tatgatgaga actgtttcca gccgaatgaa ggatcacaat gggtcaagt    2280 tgaagacctc tgtttggaga aacagatctt ttaccgattg gtttctggtt tgcattctag    2340
tatctccacc cacctcacaa acgaatatct gaatttgaaa aatggagcat acgaaccaaa    2400
```

```
tttgaaacag ttcatgatca aagttgggta ttttactgaa agaattcaaa acttacatct    2460
caattatgtc cttgtattga agtcactaat aaagctacaa gaatacaatg ttatcgacaa    2520
tctacctctc gatgactctt tgaaagctgg tcttagcggt ttaatatctc aaggagcaca    2580
gggtattaac cagagctctg atgattatct atttaacgag aaggttcttt tccaaaatga    2640
ccaaaatgat gatttgaaaa atgaattccg tgacaaattc cgcaacgtga ctagattaat    2700
ggattgtgtc cacggtgttt aaacccagc gcctggcggg                          2740
```